(12) United States Patent
Catanese, III et al.

(10) Patent No.: US 7,951,158 B2
(45) Date of Patent: May 31, 2011

(54) DEVICES, SYSTEMS AND METHODS FOR RETRACTING, LIFTING, COMPRESSING, SUPPORTING OR REPOSITIONING TISSUES OR ANATOMICAL STRUCTURES

(75) Inventors: Joseph Catanese, III, San Leandro, CA (US); Theodore Charles Lamson, Pleasanton, CA (US); Joshua Makower, Los Altos, CA (US); Amik Nagpurkar, San Francisco, CA (US); Amrish Jayprakash Walke, Santa Clara, CA (US); Claude Vidal, Santa Barbara, CA (US); Russell J. Redmond, Goleta, CA (US); Michael Collinson, Goleta, CA (US); Jacqueline Nerney Welch, Pacifica, CA (US)

(73) Assignee: Neotract, Inc., Pleasanton, CA (US)

( * ) Notice: Subject to any disclaimer, the term of this patent is extended or adjusted under 35 U.S.C. 154(b) by 0 days.

(21) Appl. No.: 11/833,710

(22) Filed: Aug. 3, 2007

(65) Prior Publication Data

US 2008/0033232 A1 Feb. 7, 2008

Related U.S. Application Data

(60) Division of application No. 11/318,246, filed on Dec. 22, 2005, now Pat. No. 7,645,286, and a continuation-in-part of application No. 11/134,870, filed on May 20, 2005, now Pat. No. 7,758,594.

(51) Int. Cl.
*A61B 17/08* (2006.01)
(52) U.S. Cl. ..................................................... 606/151
(58) Field of Classification Search .................. 606/151, 606/153, 72, 99, 139, 213, 232; 604/27; 623/17.16
See application file for complete search history.

(56) References Cited

U.S. PATENT DOCUMENTS

| 659,422 A | 10/1900 | Shidler |
| 780,392 A | 1/1905 | Wanamaker et al. |
| 789,467 A | 5/1905 | West |
| 2,579,192 A | 12/1951 | Kohl |
| 2,646,298 A | 7/1953 | Leary |
| 2,697,624 A | 12/1954 | Thomas et al. |
| 2,734,299 A | 2/1956 | Masson |
| 2,825,592 A | 3/1958 | Semple |
| 3,326,586 A | 6/1967 | Frost et al. |
| 3,470,834 A | 10/1969 | Bone |
| 3,521,918 A | 7/1970 | Hammond |
| 3,713,680 A | 1/1973 | Pagano |

(Continued)

FOREIGN PATENT DOCUMENTS

DE 10159470 6/2003

(Continued)

OTHER PUBLICATIONS

Sharp, Howard T., M.D., et al., "Instruments and Methods—The 4-S Modification of the Roeder Knot: How to Tie It", Obstetrics & Gynecology, p. 1004-1006, vol. 90, No. 6, Dec. 1997.

(Continued)

*Primary Examiner* — Darwin P Erezo
*Assistant Examiner* — Gregory Anderson
(74) *Attorney, Agent, or Firm* — Steptoe & Johnson LLP

(57) ABSTRACT

Devices, systems and methods for retracting, lifting, compressing, supporting or repositioning tissues, organs, anatomical structures, grafts or other structures within the body of human or animal subjects for the purpose of treating a diseases or disorders and/or for cosmetic or reconstructive purposes and/or for research and development purposes or other purposes.

17 Claims, 47 Drawing Sheets

U.S. PATENT DOCUMENTS

| | | |
|---|---|---|
| 3,716,058 A | 2/1973 | Tanner, Jr. |
| 3,756,638 A | 9/1973 | Stockberger |
| 3,873,140 A | 3/1975 | Bloch |
| 3,875,648 A | 4/1975 | Bone |
| 3,931,667 A | 1/1976 | Merser et al. |
| 3,976,079 A | 8/1976 | Samuels et al. |
| 4,006,747 A | 2/1977 | Kronenthal et al. |
| 4,210,148 A | 7/1980 | Stivala |
| 4,235,238 A | 11/1980 | Ogiu et al. |
| 4,291,698 A | 9/1981 | Fuchs et al. |
| 4,409,974 A | 10/1983 | Freedland |
| 4,493,323 A | 1/1985 | Albright et al. |
| 4,513,746 A | 4/1985 | Aranyi |
| 4,621,640 A | 11/1986 | Mulhollan et al. |
| 4,657,461 A | 4/1987 | Smith |
| 4,669,473 A | 6/1987 | Richards et al. |
| 4,705,040 A | 11/1987 | Mueller et al. |
| 4,714,281 A | 12/1987 | Peck |
| 4,738,255 A | 4/1988 | Goble et al. |
| 4,741,330 A | 5/1988 | Hayhurst |
| 4,744,364 A | 5/1988 | Kensey |
| 4,750,492 A | 6/1988 | Jacobs |
| 4,762,128 A | 8/1988 | Rosenbluth |
| 4,823,794 A | 4/1989 | Pierce |
| 4,899,743 A | 2/1990 | Nicholson et al. |
| 4,926,860 A | 5/1990 | Stice et al. |
| 4,946,468 A | 8/1990 | Li |
| 4,955,913 A | 9/1990 | Robinson |
| 4,968,315 A | 11/1990 | Gatturna et al. |
| 5,002,550 A | 3/1991 | Li |
| 5,041,129 A | 8/1991 | Hayhurst et al. |
| 5,046,513 A | 9/1991 | Gatturna et al. |
| 5,053,046 A | 10/1991 | Janese |
| 5,100,421 A | 3/1992 | Christoudias |
| 5,123,914 A | 6/1992 | Cope |
| 5,129,912 A | 7/1992 | Noda et al. |
| 5,192,303 A | 3/1993 | Gatturna et al. |
| 5,203,787 A | 4/1993 | Noblitt et al. |
| 5,217,470 A | 6/1993 | Weston |
| 5,217,486 A | 6/1993 | Rice et al. |
| 5,234,454 A | 8/1993 | Bangs |
| 5,236,445 A | 8/1993 | Hayhurst et al. |
| 5,258,015 A | 11/1993 | Li et al. |
| 5,269,809 A | 12/1993 | Hayhurst et al. |
| 5,330,488 A | 7/1994 | Goldrath |
| 5,334,200 A | 8/1994 | Johnson |
| 5,336,240 A | 8/1994 | Metzler et al. |
| 5,354,271 A | 10/1994 | Voda |
| 5,358,511 A | 10/1994 | Gatturna et al. |
| 5,364,408 A | 11/1994 | Gordon |
| 5,366,490 A | 11/1994 | Edwards et al. |
| 5,368,599 A | 11/1994 | Hirsch et al. |
| 5,370,646 A | 12/1994 | Reese et al. |
| 5,380,334 A | 1/1995 | Torrie et al. |
| 5,391,182 A | 2/1995 | Chin |
| 5,403,348 A | 4/1995 | Bonutti |
| 5,405,352 A | 4/1995 | Weston |
| 5,411,520 A | 5/1995 | Nash et al. |
| 5,417,691 A | 5/1995 | Hayhurst |
| 5,435,805 A | 7/1995 | Edwards et al. |
| 5,470,337 A | 11/1995 | Moss |
| 5,472,446 A | 12/1995 | de la Torre |
| 5,480,406 A | 1/1996 | Nolan et al. |
| 5,501,690 A | 3/1996 | Measamer et al. |
| 5,507,754 A | 4/1996 | Green et al. |
| 5,522,846 A | 6/1996 | Bonutti |
| 5,531,763 A | 7/1996 | Mastri et al. |
| 5,536,240 A | 7/1996 | Edwards et al. |
| 5,540,704 A | 7/1996 | Gordon et al. |
| 5,545,171 A | 8/1996 | Sharkey et al. |
| 5,545,178 A | 8/1996 | Kensey et al. |
| 5,550,172 A | 8/1996 | Regula et al. |
| 5,554,162 A | 9/1996 | DeLange |
| 5,554,171 A | 9/1996 | Gatturna et al. |
| 5,562,689 A | 10/1996 | Green et al. |
| 5,569,305 A | 10/1996 | Bonutti |
| 5,571,104 A | 11/1996 | Li |
| 5,573,540 A | 11/1996 | Yoon |
| 5,578,044 A | 11/1996 | Gordon et al. |
| 5,591,177 A | 1/1997 | Lehrer |
| 5,593,421 A | 1/1997 | Bauer |
| 5,611,515 A | 3/1997 | Benderev et al. |
| 5,626,614 A | 5/1997 | Hart |
| 5,630,824 A | 5/1997 | Hart |
| 5,647,836 A | 7/1997 | Blake, III et al. |
| 5,665,109 A | 9/1997 | Yoon |
| 5,667,486 A | 9/1997 | Mikulich et al. |
| 5,669,917 A | 9/1997 | Sauer et al. |
| 5,690,649 A | 11/1997 | Li |
| 5,690,677 A | 11/1997 | Schmiedling et al. |
| 5,697,950 A | 12/1997 | Fucci et al. |
| 5,707,394 A | 1/1998 | Miller et al. |
| 5,716,368 A | 2/1998 | de la Torre et al. |
| 5,718,717 A | 2/1998 | Bonutti |
| 5,725,556 A | 3/1998 | Moser et al. |
| 5,725,557 A | 3/1998 | Gatturna et al. |
| 5,733,306 A | 3/1998 | Bonutti |
| 5,741,276 A | 4/1998 | Poloyko et al. |
| 5,746,753 A | 5/1998 | Sullivan et al. |
| 5,749,846 A | 5/1998 | Edwards et al. |
| 5,752,963 A | 5/1998 | Allard et al. |
| 5,782,862 A | 7/1998 | Bonutti |
| 5,782,864 A | 7/1998 | Lizardi |
| 5,800,445 A | 9/1998 | Ratcliff et al. |
| 5,807,403 A | 9/1998 | Beyar et al. |
| 5,810,848 A | 9/1998 | Hayhurst |
| 5,814,072 A | 9/1998 | Bonutti |
| 5,830,221 A | 11/1998 | Stein |
| 5,845,645 A | 12/1998 | Bonutti |
| 5,846,254 A | 12/1998 | Schulze et al. |
| 5,861,002 A | 1/1999 | Desai |
| 5,868,762 A | 2/1999 | Cragg et al. |
| 5,873,891 A | 2/1999 | Sohn |
| 5,897,574 A | 4/1999 | Bonutti |
| 5,899,911 A | 5/1999 | Carter |
| 5,899,921 A | 5/1999 | Caspari et al. |
| 5,904,696 A | 5/1999 | Rosenman |
| 5,908,428 A | 6/1999 | Scirica et al. |
| 5,919,198 A | 7/1999 | Graves, Jr. et al. |
| 5,919,202 A | 7/1999 | Yoon |
| 5,921,986 A | 7/1999 | Bonutti |
| 5,928,252 A | 7/1999 | Steadman et al. |
| 5,931,844 A | 8/1999 | Thompson et al. |
| 5,944,739 A | 8/1999 | Zlock et al. |
| 5,948,001 A | 9/1999 | Larsen |
| 5,948,002 A | 9/1999 | Bonutti |
| 5,954,057 A | 9/1999 | Li |
| 5,954,747 A | 9/1999 | Clark |
| 5,964,732 A | 10/1999 | Wilard |
| 5,971,447 A | 10/1999 | Steck, III |
| 6,010,514 A | 1/2000 | Burney et al. |
| 6,011,525 A | 1/2000 | Piole |
| 6,030,393 A | 2/2000 | Corlew |
| 6,033,430 A | 3/2000 | Bonutti |
| 6,036,701 A | 3/2000 | Rosenman |
| 6,048,351 A | 4/2000 | Gordon et al. |
| 6,053,908 A | 4/2000 | Crainich et al. |
| 6,056,722 A | 5/2000 | Jayaraman |
| 6,056,772 A | 5/2000 | Bonutti |
| 6,068,648 A | 5/2000 | Cole et al. |
| 6,080,167 A | 6/2000 | Lyell |
| 6,086,608 A | 7/2000 | Ek et al. |
| 6,110,183 A | 8/2000 | Cope |
| 6,117,160 A | 9/2000 | Bonutti |
| 6,117,161 A | 9/2000 | Li et al. |
| 6,120,539 A | 9/2000 | Eldridge et al. |
| 6,139,555 A | 10/2000 | Hart et al. |
| RE36,974 E | 11/2000 | Bonutti |
| 6,143,006 A | 11/2000 | Chan |
| 6,152,935 A * | 11/2000 | Kammerer et al. ............ 606/144 |
| 6,159,234 A | 12/2000 | Bonutti et al. |
| 6,200,329 B1 | 3/2001 | Fung et al. |
| 6,206,895 B1 | 3/2001 | Levinson |
| 6,228,096 B1 | 5/2001 | Marchand |
| 6,258,124 B1 | 7/2001 | Darois et al. |
| 6,261,302 B1 | 7/2001 | Voegele et al. |
| 6,270,530 B1 | 8/2001 | Eldridge et al. |

| | | |
|---|---|---|
| 6,280,460 B1 | 8/2001 | Bolduc et al. |
| 6,290,711 B1 | 9/2001 | Caspari et al. |
| 6,312,448 B1 | 11/2001 | Bonutti |
| 6,319,263 B1 | 11/2001 | Levinson |
| 6,322,112 B1 | 11/2001 | Duncan |
| 6,332,889 B1 | 12/2001 | Sancoff et al. |
| 6,398,795 B1 | 6/2002 | McAlister et al. |
| 6,425,900 B1 | 7/2002 | Knodel et al. |
| 6,428,562 B2 | 8/2002 | Bonutti |
| 6,436,107 B1 | 8/2002 | Wang et al. |
| 6,461,355 B2 | 10/2002 | Svejkovsky et al. |
| 6,482,235 B1 | 11/2002 | Lambrecht et al. |
| 6,488,691 B1 | 12/2002 | Carroll et al. |
| 6,491,707 B2 | 12/2002 | Makower et al. |
| 6,494,888 B1 | 12/2002 | Laufer et al. |
| 6,500,195 B2 | 12/2002 | Bonutti |
| 6,506,190 B1 | 1/2003 | Walshe |
| 6,506,196 B1 | 1/2003 | Laufer |
| 6,517,569 B2 | 2/2003 | Mikus et al. |
| 6,527,702 B2 | 3/2003 | Whalen et al. |
| 6,527,794 B1 | 3/2003 | McDevitt et al. |
| 6,530,932 B1 | 3/2003 | Swayze et al. |
| 6,533,796 B1 | 3/2003 | Sauer et al. |
| 6,547,725 B1 | 4/2003 | Paolitto et al. |
| 6,551,328 B2 | 4/2003 | Kortenbach |
| 6,551,333 B2 | 4/2003 | Kuhns et al. |
| 6,565,578 B1 | 5/2003 | Peifer et al. |
| 6,569,187 B1 | 5/2003 | Bonutti et al. |
| 6,572,626 B1 | 6/2003 | Knodel et al. |
| 6,572,635 B1 | 6/2003 | Bonutti |
| 6,572,653 B1 | 6/2003 | Simonson |
| 6,592,609 B1 | 7/2003 | Bonutti |
| 6,596,013 B2 | 7/2003 | Yang et al. |
| 6,626,913 B1 | 9/2003 | McKinnon et al. |
| 6,626,916 B1 | 9/2003 | Yeung et al. |
| 6,626,919 B1 | 9/2003 | Swanstrom |
| 6,629,534 B1 | 10/2003 | St. Goar et al. |
| 6,641,592 B1 | 11/2003 | Sauer et al. |
| 6,656,182 B1 | 12/2003 | Hayhurst |
| 6,660,023 B2 | 12/2003 | McDevitt et al. |
| 6,663,589 B1 | 12/2003 | Halevy |
| 6,663,639 B1 | 12/2003 | Laufer et al. |
| 6,699,263 B2 | 3/2004 | Cope |
| 6,706,047 B2 | 3/2004 | Trout et al. |
| 6,709,493 B2 | 3/2004 | DeGuiseppi et al. |
| 6,715,804 B2 | 4/2004 | Beers |
| 6,719,709 B2 | 4/2004 | Whalen et al. |
| 6,730,112 B2 | 5/2004 | Levinson |
| 6,736,823 B2 | 5/2004 | Darois et al. |
| 6,736,854 B2 | 5/2004 | Vadurro et al. |
| 6,740,098 B2 | 5/2004 | Abrams et al. |
| 6,767,037 B2 | 7/2004 | Wenstrom, Jr. |
| 6,770,076 B2 | 8/2004 | Foerster |
| 6,773,438 B1 | 8/2004 | Knodel et al. |
| 6,773,441 B1 | 8/2004 | Laufer et al. |
| 6,790,213 B2 | 9/2004 | Cherok et al. |
| 6,802,846 B2 | 10/2004 | Hauschild et al. |
| 6,821,282 B2 | 11/2004 | Perry et al. |
| 6,821,285 B2 | 11/2004 | Laufer et al. |
| 6,821,291 B2 | 11/2004 | Boleg et al. |
| 6,835,200 B2 | 12/2004 | Laufer et al. |
| 6,905,475 B2 | 6/2005 | Hauschild et al. |
| 6,908,473 B2 | 6/2005 | Skiba et al. |
| 6,926,732 B2 | 8/2005 | Derus et al. |
| 6,951,565 B2 | 10/2005 | Keane et al. |
| 6,986,775 B2 | 1/2006 | Morales et al. |
| 6,991,596 B2 | 1/2006 | Whalen et al. |
| 6,991,647 B2 | 1/2006 | Jadhav |
| 6,997,940 B2 | 2/2006 | Bonutti |
| 7,001,327 B2 | 2/2006 | Whalen et al. |
| 7,011,688 B2 | 3/2006 | Gryska et al. |
| 7,015,253 B2 | 3/2006 | Escandon et al. |
| 7,048,698 B2 | 5/2006 | Whalen et al. |
| 7,048,747 B2 | 5/2006 | Arcia et al. |
| 7,060,077 B2 | 6/2006 | Gordon et al. |
| 7,081,126 B2 | 7/2006 | McDevitt et al. |
| 7,083,638 B2 | 8/2006 | Foerster |
| 7,087,073 B2 | 8/2006 | Bonutti |
| 7,089,064 B2 | 8/2006 | Manker et al. |
| 7,090,690 B2 | 8/2006 | Foerster et al. |
| 7,093,601 B2 | 8/2006 | Manker et al. |
| 7,105,004 B2 | 9/2006 | Dicesare et al. |
| 7,108,655 B2 | 9/2006 | Whalen et al. |
| 7,141,038 B2 | 11/2006 | Whalen et al. |
| 7,153,314 B2 | 12/2006 | Laufer et al. |
| 7,179,225 B2 | 2/2007 | Shluzas et al. |
| 7,226,558 B2 | 6/2007 | Nieman et al. |
| 7,232,448 B2 | 6/2007 | Battles et al. |
| 7,288,063 B2 | 10/2007 | Petros et al. |
| 7,303,108 B2 | 12/2007 | Shelton, IV |
| 7,320,701 B2 | 1/2008 | Haut et al. |
| 7,322,974 B2 | 1/2008 | Swoyer et al. |
| 7,334,822 B1 | 2/2008 | Hines, Jr. |
| 7,340,300 B2 | 3/2008 | Christopherson et al. |
| 7,399,304 B2 | 7/2008 | Gambale et al. |
| 7,402,166 B2 | 7/2008 | Feigl |
| 7,416,554 B2 | 8/2008 | Lam et al. |
| 7,553,317 B2 | 6/2009 | Weisenburgh, II et al. |
| 7,608,108 B2 | 10/2009 | Bhatnagar et al. |
| 7,658,311 B2 | 2/2010 | Boudreaux |
| 7,674,275 B2 | 3/2010 | Martin et al. |
| 7,727,248 B2 | 6/2010 | Smith et al. |
| 2001/0044639 A1 | 11/2001 | Levinson |
| 2002/0128684 A1 | 9/2002 | Foerster |
| 2002/0161382 A1 | 10/2002 | Neisz et al. |
| 2002/0193809 A1 | 12/2002 | Meade et al. |
| 2003/0109769 A1 | 6/2003 | Lowery et al. |
| 2003/0191497 A1 | 10/2003 | Cope |
| 2003/0204195 A1 | 10/2003 | Keane et al. |
| 2004/0030217 A1 | 2/2004 | Yeung et al. |
| 2004/0043052 A1 | 3/2004 | Hunter et al. |
| 2004/0078046 A1 | 4/2004 | Barzell et al. |
| 2004/0193191 A1 | 9/2004 | Starksen et al. |
| 2004/0193194 A1 | 9/2004 | Laufer et al. |
| 2004/0194790 A1 | 10/2004 | Laufer et al. |
| 2004/0243178 A1 | 12/2004 | Haut et al. |
| 2004/0243179 A1 | 12/2004 | Foerster |
| 2004/0243180 A1 | 12/2004 | Donnelly |
| 2004/0243227 A1 | 12/2004 | Starksen et al. |
| 2004/0260345 A1 | 12/2004 | Foerster |
| 2005/0055087 A1 | 3/2005 | Starksen |
| 2005/0065550 A1 | 3/2005 | Starksen et al. |
| 2005/0107811 A1 | 5/2005 | Starksen et al. |
| 2005/0107812 A1 | 5/2005 | Starksen et al. |
| 2005/0154401 A1 | 7/2005 | Weldon et al. |
| 2005/0165272 A1* | 7/2005 | Okada et al. .................. 600/114 |
| 2005/0177181 A1 | 8/2005 | Kagan et al. |
| 2005/0203344 A1 | 9/2005 | Orban, III et al. |
| 2005/0216078 A1 | 9/2005 | Starksen et al. |
| 2005/0267405 A1 | 12/2005 | Shah |
| 2005/0273138 A1 | 12/2005 | To et al. |
| 2006/0025750 A1 | 2/2006 | Starksen et al. |
| 2006/0025784 A1 | 2/2006 | Starksen et al. |
| 2006/0025789 A1 | 2/2006 | Laufer et al. |
| 2006/0025819 A1 | 2/2006 | Nobis et al. |
| 2006/0030884 A1 | 2/2006 | Yeung et al. |
| 2006/0058817 A1 | 3/2006 | Starksen et al. |
| 2006/0089646 A1 | 4/2006 | Bonutti |
| 2006/0167477 A1 | 7/2006 | Arcia et al. |
| 2006/0265042 A1 | 11/2006 | Catanese, III et al. |
| 2006/0282081 A1 | 12/2006 | Fanton et al. |
| 2007/0049929 A1 | 3/2007 | Catanese, III |
| 2007/0049970 A1 | 3/2007 | Belef et al. |
| 2007/0060931 A1 | 3/2007 | Hamilton et al. |
| 2007/0088362 A1 | 4/2007 | Bonutti |
| 2007/0112385 A1 | 5/2007 | Conlon |
| 2007/0142846 A1 | 6/2007 | Catanese, III et al. |
| 2007/0173888 A1 | 7/2007 | Gertner et al. |
| 2007/0260259 A1 | 11/2007 | Fanton et al. |
| 2008/0009888 A1 | 1/2008 | Ewers et al. |
| 2008/0021445 A1 | 1/2008 | Elmouelhi et al. |
| 2008/0033488 A1 | 2/2008 | Catanese, III et al. |
| 2008/0039894 A1 | 2/2008 | Catanese, III et al. |
| 2008/0045978 A1 | 2/2008 | Kuhns et al. |
| 2008/0058710 A1 | 3/2008 | Wilk |
| 2008/0065120 A1 | 3/2008 | Zannis et al. |
| 2008/0082113 A1 | 4/2008 | Bishop et al. |
| 2008/0086172 A1 | 4/2008 | Martin et al. |

| | | |
|---|---|---|
| 2008/0091220 A1 | 4/2008 | Chu |
| 2008/0091237 A1 | 4/2008 | Schwartz et al. |
| 2008/0119874 A1 | 5/2008 | Merves |
| 2008/0154378 A1 | 6/2008 | Pelo |
| 2008/0195145 A1 | 8/2008 | Bonutti et al. |
| 2008/0208220 A1 | 8/2008 | Shiono et al. |
| 2010/0010631 A1 | 1/2010 | Otte et al. |
| 2010/0114162 A1 | 5/2010 | Bojarski et al. |
| 2010/0286106 A1 | 11/2010 | Gat et al. |
| 2010/0286679 A1 | 11/2010 | Hoey et al. |

FOREIGN PATENT DOCUMENTS

| | | |
|---|---|---|
| EP | 0246836 | 12/1991 |
| EP | 0464480 | 1/1992 |
| EP | 0632999 | 1/1995 |
| EP | 1016377 | 7/2000 |
| EP | 1082941 | 3/2005 |
| EP | 1006909 | 1/2007 |
| EP | 1852071 | 11/2007 |
| EP | 1670361 | 4/2008 |
| EP | 1884198 | 6/2008 |
| EP | 1884199 | 6/2008 |
| EP | 1331886 | 12/2008 |
| FR | 2750031 | 6/1996 |
| JP | 58036559 | 3/1983 |
| JP | 9122134 | 5/1997 |
| JP | 2004344427 | 12/2004 |
| RU | 2062121 | 6/1996 |
| RU | 2112571 | 6/1998 |
| RU | 2128012 | 3/1999 |
| RU | 2221501 | 1/2004 |
| SU | 0825094 | 4/1981 |
| WO | WO 93/04727 | 3/1993 |
| WO | WO 93/15664 | 8/1993 |
| WO | WO 92/10142 | 6/1996 |
| WO | WO0230335 | 4/2002 |
| WO | WO03/039334 | 5/2003 |
| WO | WO 03/077772 | 9/2003 |
| WO | WO2004/019787 | 3/2004 |
| WO | WO2004017845 | 4/2004 |
| WO | WO2004030569 | 4/2004 |
| WO | WO 2004103189 | 12/2004 |
| WO | WO2007064906 | 6/2007 |
| WO | WO2007053516 | 10/2007 |
| WO | WO2008006084 | 1/2008 |
| WO | WO2008043044 | 4/2008 |
| WO | WO2008043917 | 4/2008 |
| WO | WO2009009617 | 1/2009 |
| WO | WO2010011832 | 1/2010 |

OTHER PUBLICATIONS

P. Schauer et al., "New applications for endoscopy: the emerging field of endoluminal and transgastric bariatric surgery," Surgical Endoscopy, Received Apr. 24, 2006/Accepted Jun. 7, 2006.

Richard Berges et al., "Alternative Minimalinvasive Therapien Beim Benignen Prostatasyndrom", Medizin, Jg. 104, Heft 37, Sep. 14, 2007.

Rudolf Hartung, et al., "Instrumentelle Therapie der benignen Prostatahyperplasie", Medizin, Deutsches Ärzteblatt 97, Heft 15, Apr. 14, 2000.

Klaus Hofner, et al., "Operative Therapie des benignen Prostatasyndroms", Medizin, Dtsch Arztebl 2007; 104(36):A 2424-9.

R. Hubmann, "Geschichte der transurethralen Prostataeingriffe", Geschichte der Medizin, Urologe [B] 2000 40:152-160.

U. Jonas, et al., "Benigne Prostatahyperplasie", Der Urologe 2006 [Sonderheft] 45:134-144.

O.A. Bacharova, et al., "The Effect of Rhodiolae Rosea Extract on Incidence Rate of Superficial Bladder Carcinoma Relapses", Kozin 1995.

S. Kruck, et al., "Aktuelle Therapiemöglichkeiten des Benignen Prostata-Syndroms", J Urol Urogynäkol 2009; 16 (1): 19-22.

Osamu Miyake, "Medical Examination and Treatment For BPH", Pharma Med vol. 22, No. 3, 2004, p. 97-103.

Ohashi Teruhisa, "Urinary Dysfunction by Lower Urinary Tract Obstruction in Male", Pharma Medica vol. 8, No. 8, p. 35-39.

O. Reich, et al., "Benignes Prostatasyndrom (BPS)", Der Urologe A Issue vol. 45, No. 6, Jun. 2006, p. 769-782.

Daito Takashi, "Low-Invasive Treatment of BPH", Medico vol. 34, No. 10, p. 366-369.

Trapeznikov et al., "New Technologies in the Treatment of Benign Prostatic Hyperplasia", Urologia Nefrol (Mosk) Jul.-Aug. 1996 (4):41-47.

Koyanagi Tomohiko, et al., "Surgery View of 21st Century", Urological Surgery, vol. 84, No.1, p. 47-53.

Borzhievski, et al., "Tactics of the Surgical Treatment of Patients With Prostatic Adenoma and Acute Urinary Retention", Urologia Nefrol (Mosk), Jan.-Feb. 1987 (1):39-43.

Yeung, Jeff, "Treating Urinary Stress Incontinence Without Incision with Endoscopic Suture Anchor & Approximating Device," Aleeva Medical, Inc., 2007.

\* cited by examiner

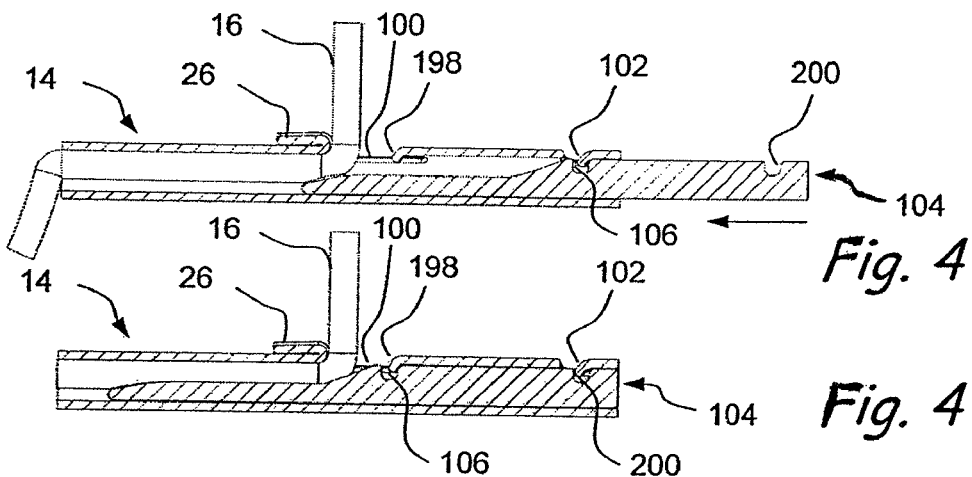
Fig. 4 A
Fig. 4 B
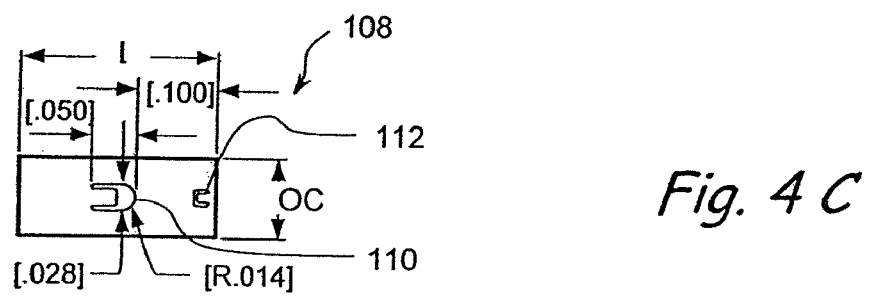
Fig. 4 C
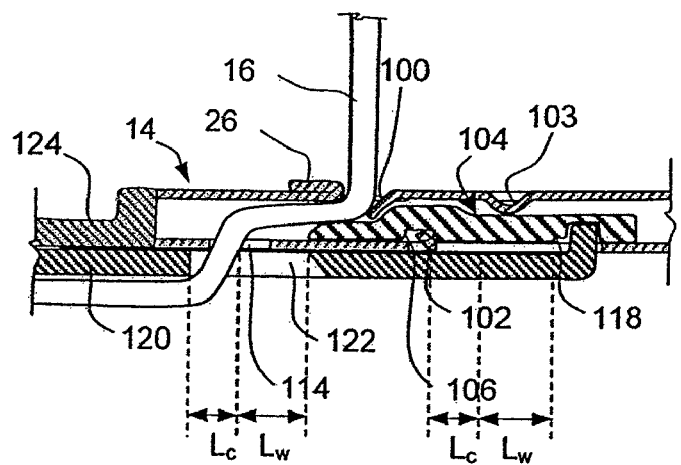
Fig. 4 D
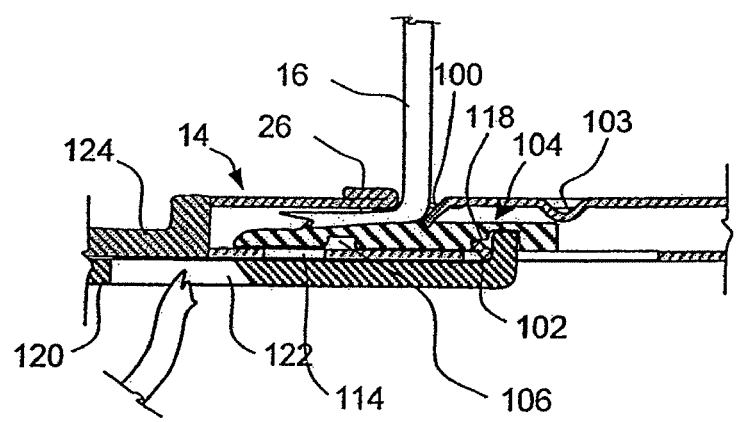
Fig. 4 E

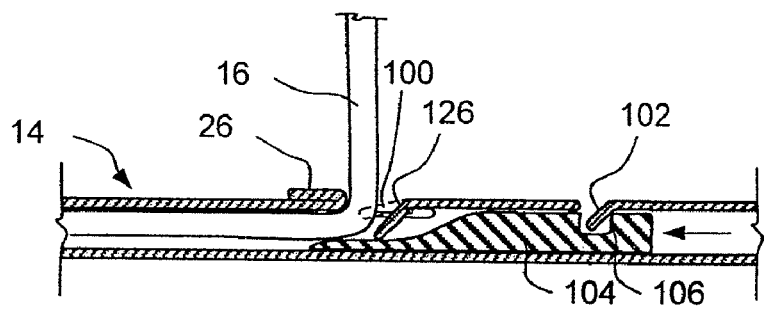
Fig. 4 F
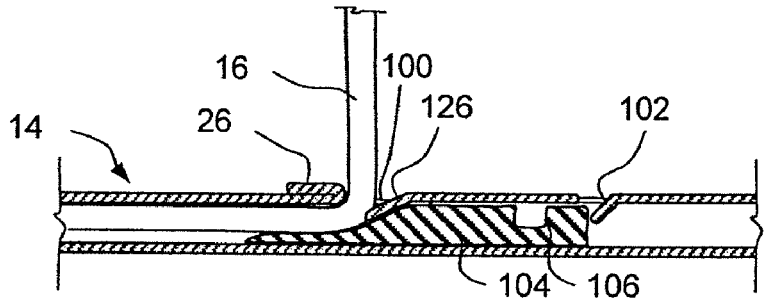
Fig. 4 G
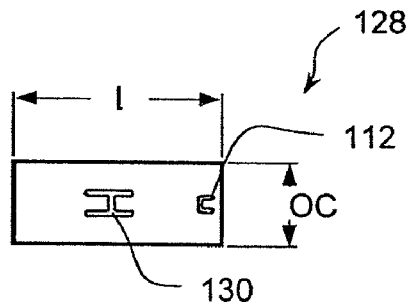
Fig. 4 H
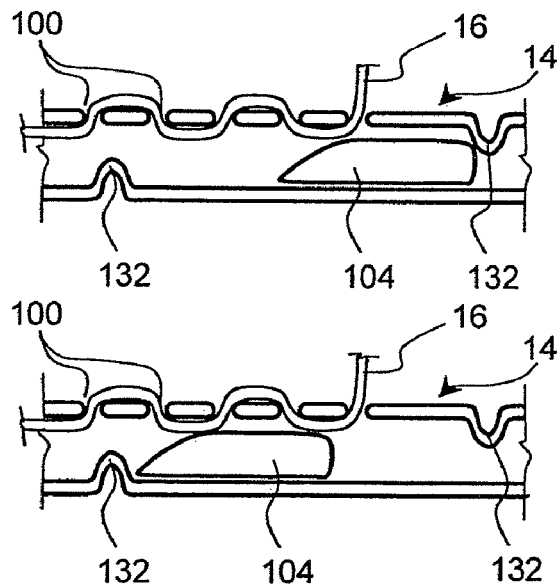
Fig. 4 I
Fig. 4 J

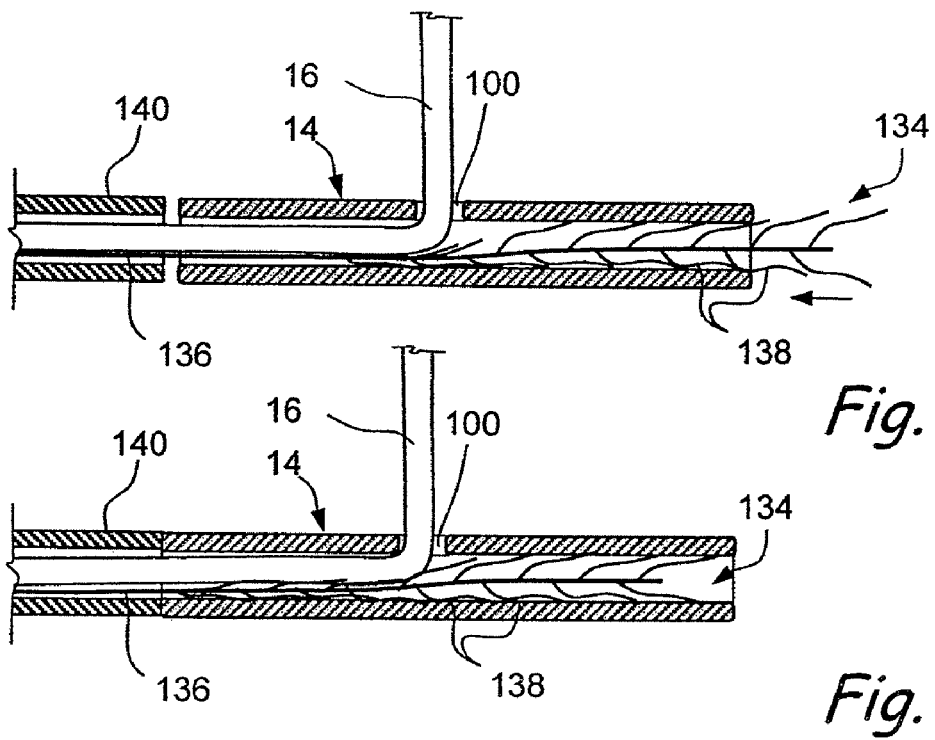
*Fig. 4 K*
*Fig. 4 L*
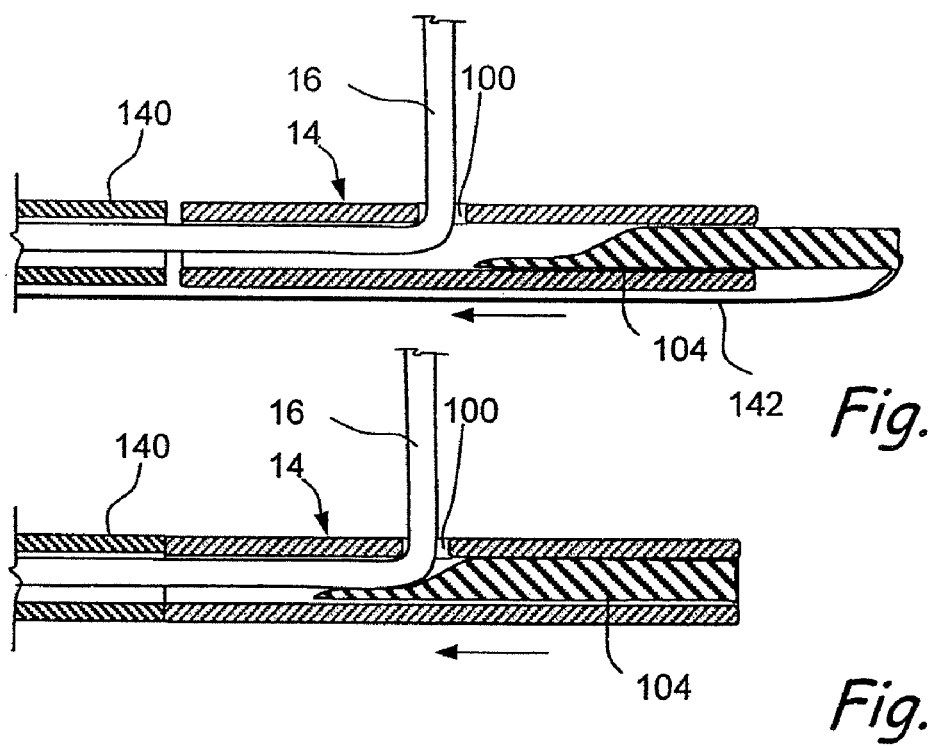
*Fig. 4 M*
*Fig. 4 N*

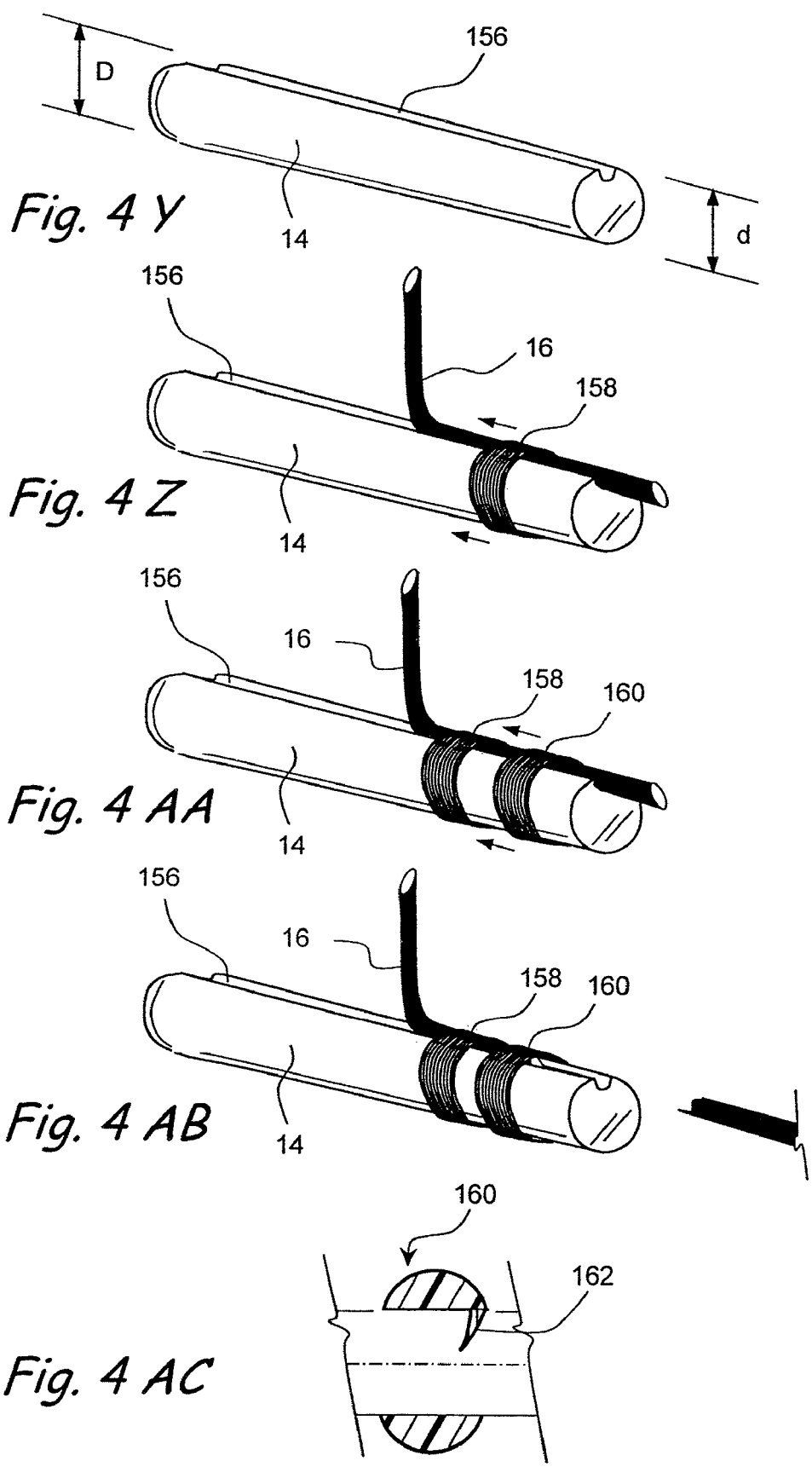

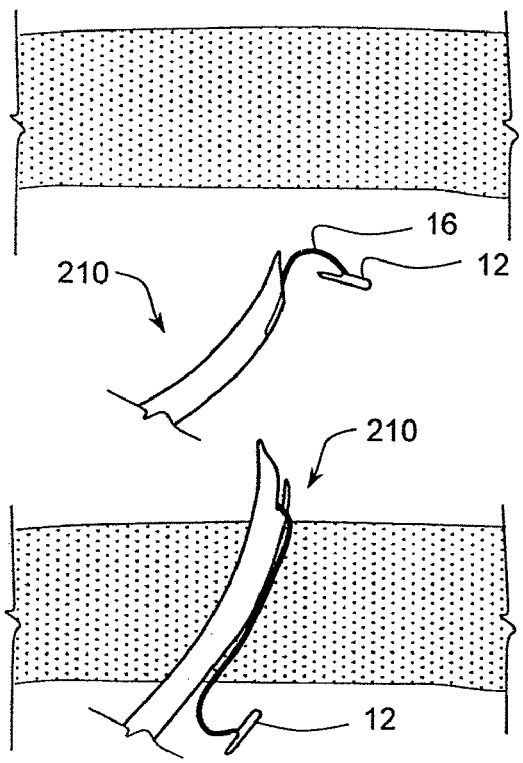
Fig. 6 L
Fig. 6 M
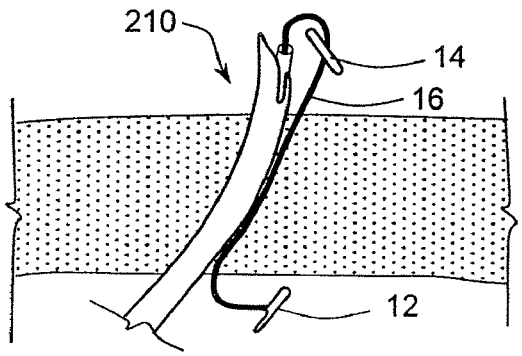
Fig. 6 N
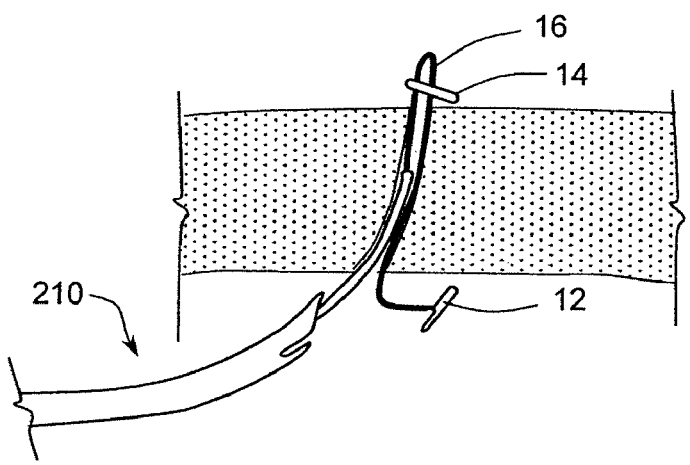
Fig. 6 O

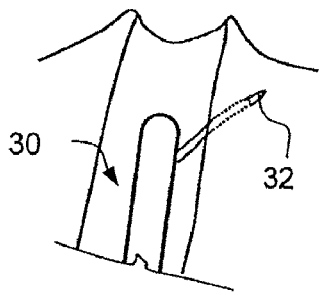 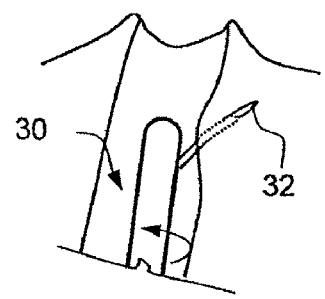 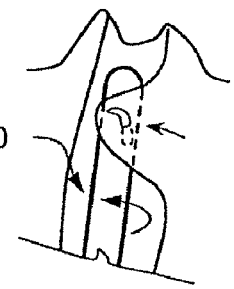
Fig. 7A    Fig. 7B    Fig. 7C
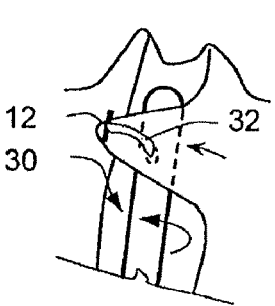 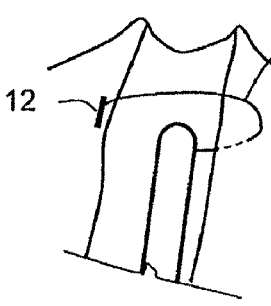 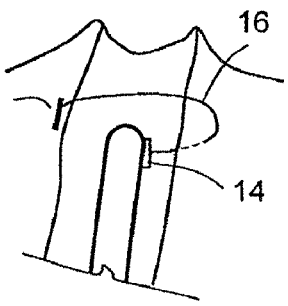
Fig. 7D    Fig. 7E    Fig. 7F
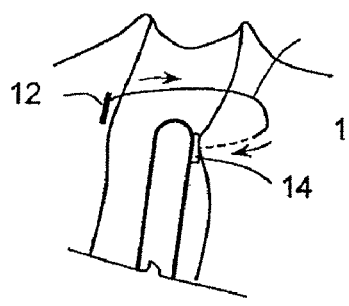 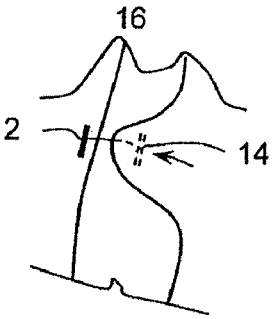 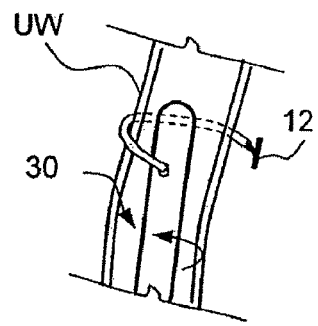
Fig. 7G    Fig. 7H    Fig. 7K
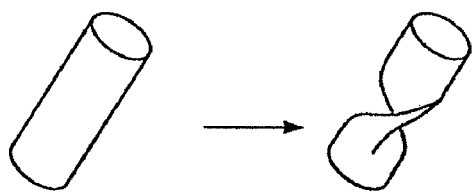
Fig. 7I    Fig. 7J

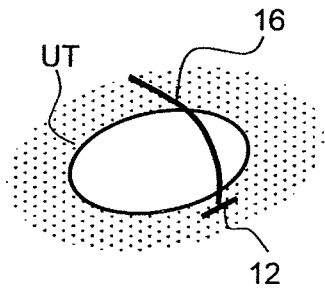
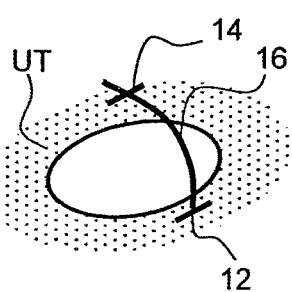
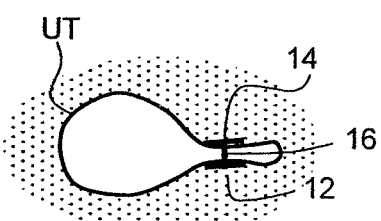
Fig. 7W　　　　Fig. 7X　　　　Fig. 7Y
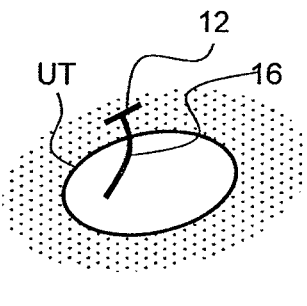
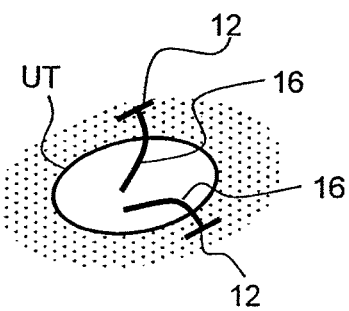
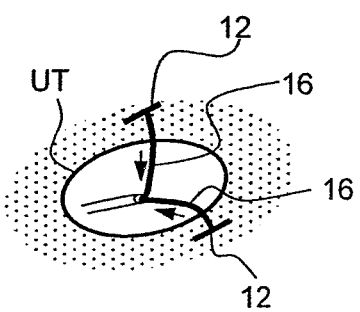
Fig. 7Z　　　　Fig. 7AA　　　　Fig. 7AB
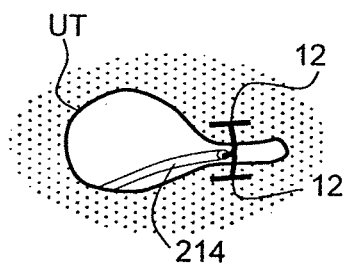
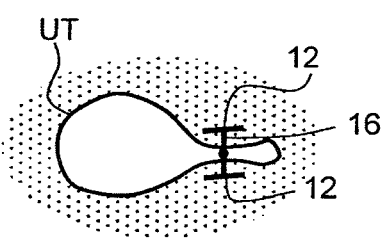
Fig. 7AC　　　　Fig. 7AD
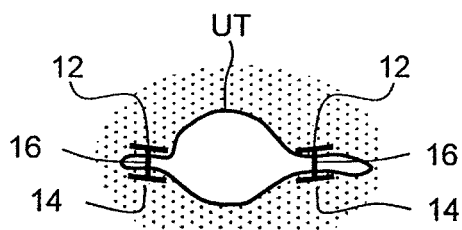
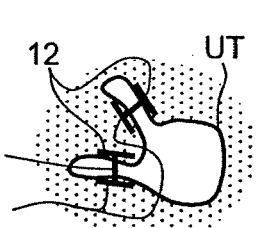
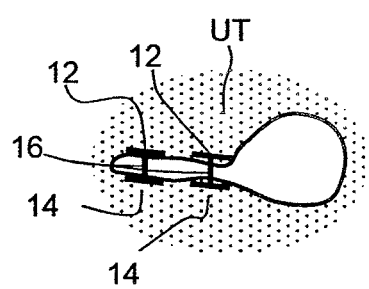
Fig. 7AE　　　　Fig. 7AF　　　　Fig. 7AG

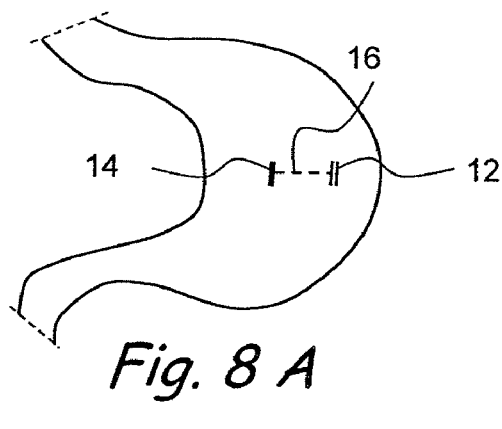
Fig. 8 A
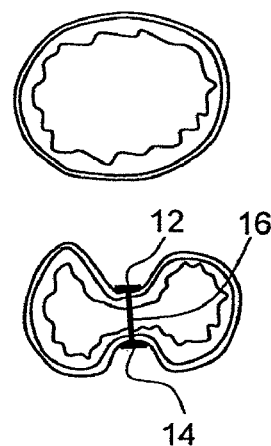
Fig. 8 B
(Prior Art)
Fig. 8 C
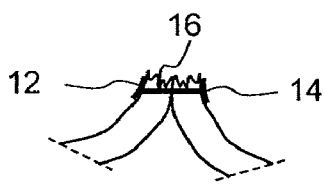
Fig. 8 D
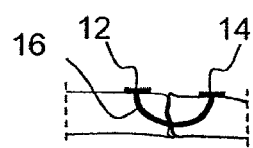
Fig. 8 E
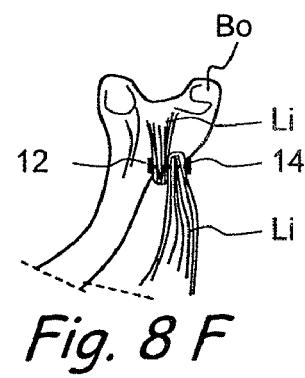
Fig. 8 F

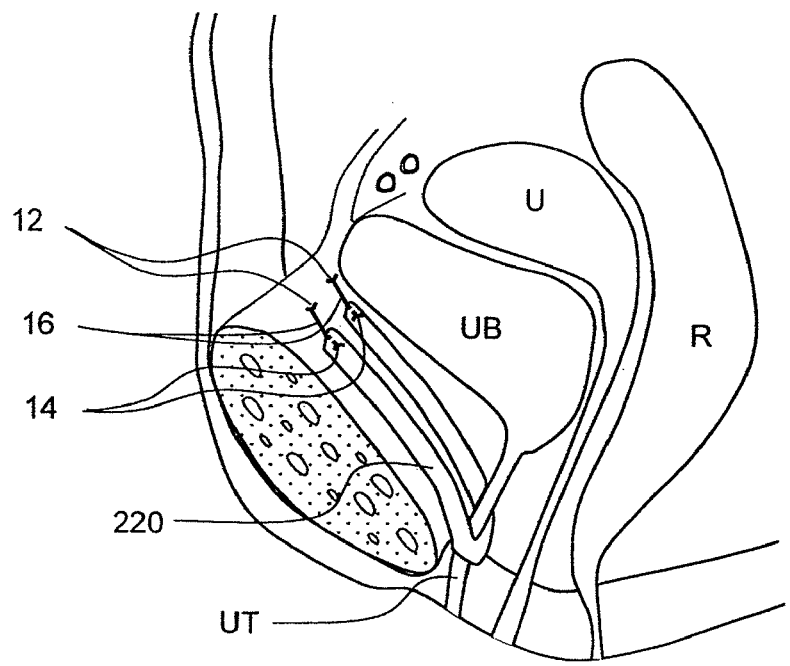
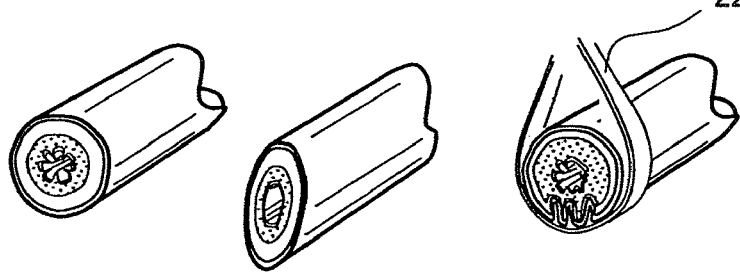
Fig. 8 K
Fig. 8 L
(Prior Art)
Fig. 8 M
(Prior Art)
Fig. 8 N
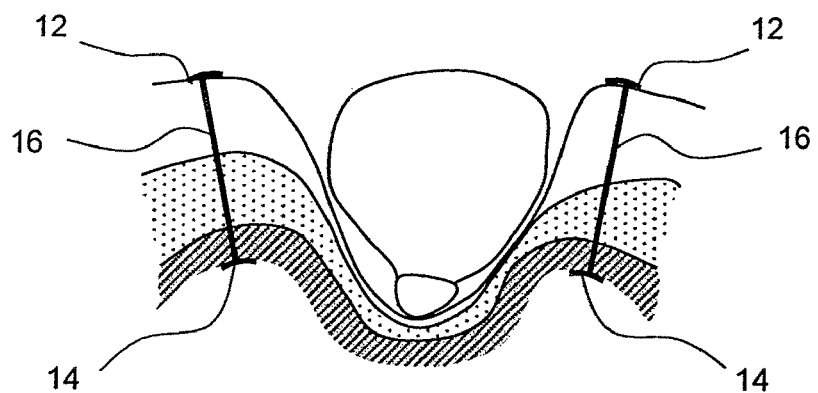
Fig. 8 O

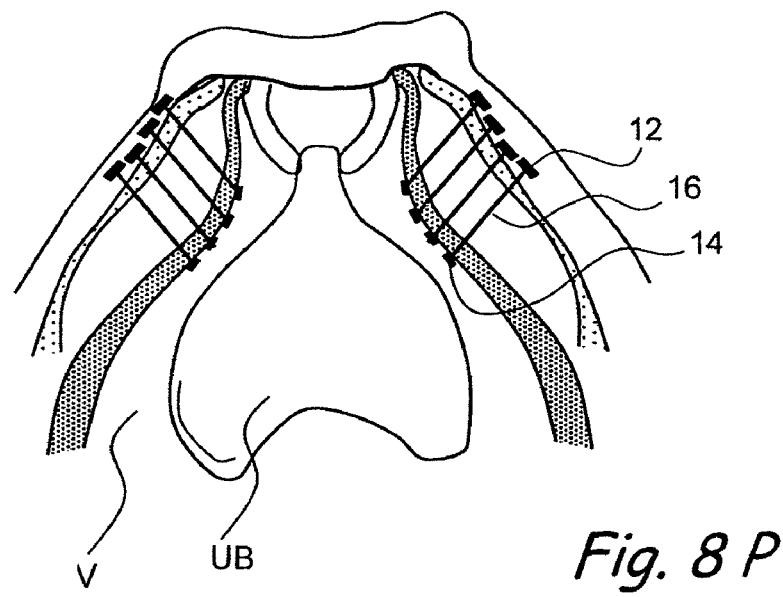
*Fig. 8 P*
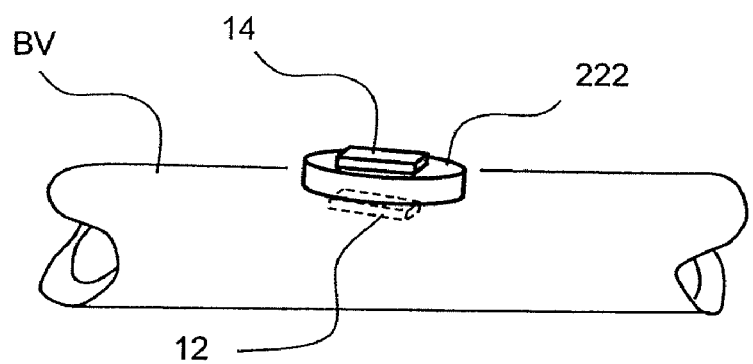
*Fig. 8 Q*
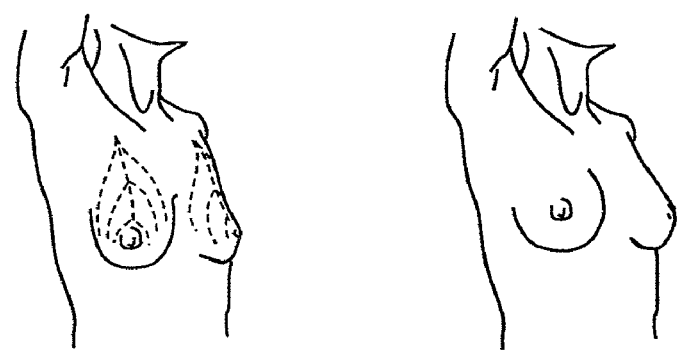
*Fig. 8 R*    *Fig. 8 S*

DEVICES, SYSTEMS AND METHODS FOR RETRACTING, LIFTING, COMPRESSING, SUPPORTING OR REPOSITIONING TISSUES OR ANATOMICAL STRUCTURES

RELATED APPLICATIONS

This application is a divisional of U.S. patent application Ser. No. 11/318,246, now U.S. Pat. No. 7,645,286, filed Dec. 22, 2005, and a continuation-in-part of U.S. patent application Ser. No. 11/134,870, now U.S. Pat. No. 7,758,594, filed on May 20, 2005, the entire disclosures of which are expressly incorporated herein by reference.

FIELD OF THE INVENTION

The present invention relates generally to medical devices and methods, and more particularly to systems and methods for retracting, lifting, compressing, supporting or repositioning tissues, organs, anatomical structures, grafts or other structures within the body of human or animal subjects for the purpose of treating a diseases or disorders and/or for cosmetic or reconstructive purposes and/or for research and development purposes or other purposes.

BACKGROUND OF THE INVENTION

There are a wide variety of situations in which it is desirable to lift, compress or otherwise reposition normal or aberrant tissues or anatomical structures (e.g., organs, ligaments, tendons, muscles, tumors, cysts, fat pads, etc.) within the body of a human or animal subject. Such procedures are often carried out for the purpose of treating or palliating the effects of diseases or disorders (e.g., hyperplasic conditions, hypertrophic conditions, neoplasias, prolapses, herniations, stenoses, constrictions, compressions, transpositions, congenital malformations, etc.) and/or for cosmetic purposes (e.g., face lifts, breast lifts, brow lifts, etc.) and/or for research and development purposes (e.g., to create animal models that mimic various pathological conditions). In many of these procedures, surgical incisions are made in the body and laborious surgical dissection is performed to access and expose the affected tissues or anatomical structures. Thereafter, in some cases, the affected tissues or anatomical structures are removed or excised. In other cases, various natural or man made materials are used to lift, sling, reposition or compress the affected tissues.

Benign Prostatic Hyperplasia (BPH)

One example of a condition where it is desirable to lift, compress or otherwise remove a pathologically enlarged tissue is Benign Prostatic Hyperplasia (BPH). BPH is one of the most common medical conditions that affect men, especially elderly men. It has been reported that, in the United Sates, more than half of all men have histopathologic evidence of BPH by age 60 and, by age 85, approximately 9 out of 10 men suffer from the condition. Moreover, the incidence and prevalence of BPH are expected to increase as the average age of the population in developed countries increases.

The prostate gland enlarges throughout a man's life. In some men, the prostatic capsule around the prostate gland may prevent the prostate gland from enlarging further. This causes the inner region of the prostate gland to squeeze the urethra. This pressure on the urethra increases resistance to urine flow through the region of the urethra enclosed by the prostate. Thus the urinary bladder has to exert more pressure to force urine through the increased resistance of the urethra. Chronic over-exertion causes the muscular walls of the urinary bladder to remodel and become stiffer. This combination of increased urethral resistance to urine flow and stiffness and hypertrophy of urinary bladder walls leads to a variety of lower urinary tract symptoms (LUTS) that may severely reduce the patient's quality of life. These symptoms include weak or intermittent urine flow while urinating, straining when urinating, hesitation before urine flow starts, feeling that the bladder has not emptied completely even after urination, dribbling at the end of urination or leakage afterward, increased frequency of urination particularly at night, urgent need to urinate etc.

In addition to patients with BPH, LUTS may also be present in patients with prostate cancer, prostate infections, and chronic use of certain medications (e.g. ephedrine, pseudoephedrine, phenylpropanolamine, antihistamines such as diphenhydramine, chlorpheniramine etc.) that cause urinary retention especially in men with prostate enlargement.

Although BPH is rarely life threatening, it can lead to numerous clinical conditions including urinary retention, renal insufficiency, recurrent urinary tract infection, incontinence, hematuria, and bladder stones.

In developed countries, a large percentage of the patient population undergoes treatment for BPH symptoms. It has been estimated that by the age of 80 years, approximately 25% of the male population of the United States will have undergone some form of BPH treatment. At present, the available treatment options for BPH include watchful waiting, medications (phytotherapy and prescription medications), surgery and minimally invasive procedures.

For patients who choose the watchful waiting option, no immediate treatment is provided to the patient, but the patient undergoes regular exams to monitor progression of the disease. This is usually done on patients that have minimal symptoms that are not especially bothersome.

Medications for treating BPH symptoms include phytotherapy and prescription medications. In phytotherapy, plant products such as Saw Palmetto, African Pygeum, Serenoa Repens (sago palm) and South African star grass are administered to the patient. Prescription medications are prescribed as first line therapy in patients with symptoms that are interfering with their daily activities. Two main classes of prescription medications are alpha-1a-adrenergic receptors blockers and 5-alpha-reductase inhibitors. Alpha-1a-adrenergic receptors blockers block that activity of alpha-1a-adrenergic receptors that are responsible for causing constriction of smooth muscle cells in the prostate. Thus, blocking the activity of alpha-1a-adrenergic receptors causes prostatic smooth muscle relaxation. This in turn reduces urethral resistance thereby reducing the severity of the symptoms. 5-alpha-reductase inhibitors block the conversion of testosterone to dihydrotestosterone. Dihydrotestosterone causes growth of epithelial cells in the prostate gland. Thus 5-alpha-reductase inhibitors cause regression of epithelial cells in the prostate gland and hence reduce the volume of the prostate gland which in turn reduces the severity of the symptoms.

Surgical procedures for treating BPH symptoms include Transurethal Resection of Prostate (TURP), Transurethral Electrovaporization of Prostate (TVP), Transurethral Incision of the Prostate (TUIP), Laser Prostatectomy and Open Prostatectomy.

Transurethal Resection of Prostate (TURP) is the most commonly practiced surgical procedure implemented for the treatment of BPH. In this procedure, prostatic urethral obstruction is reduced by removing most of the prostatic urethra and a sizeable volume of the surrounding prostate gland. This is carried out under general or spinal anesthesia. In this procedure, a urologist visualizes the urethra by inserting a resectoscope, that houses an optical lens in communication with a video camera, into the urethra such that the distal region of the resectoscope is in the region of the urethra surrounded by the prostate gland. The distal region of the resectoscope consists of an electric cutting loop that can cut prostatic tissue when an electric current is applied to the device. An electric return pad is placed on the patient to close the cutting circuit. The electric cutting loop is used to scrape away tissue from the inside of the prostate gland. The tissue that is scraped away is flushed out of the urinary system using an irrigation fluid. Using a coagulation energy setting, the loop is also used to cauterize transected vessels during the operation.

Another example of a surgical procedure for treating BPH symptoms is Transurethral Electrovaporization of the Prostate (TVP). In this procedure, a part of prostatic tissue squeezing the urethra is desiccated or vaporized. This is carried out under general or spinal anesthesia. In this procedure, a resectoscope is inserted transurethrally such that the distal region of the resectoscope is in the region of the urethra surrounded by the prostate gland. The distal region of the resectoscope consists of a rollerball or a grooved roller electrode. A controlled amount of electric current is passed through the electrode. The surrounding tissue is rapidly heated up and vaporized to create a vaporized space. Thus the region of urethra that is blocked by the surrounding prostate gland is opened up.

Another example of a surgical procedure for treating BPH symptoms is Transurethral Incision of the Prostate (TUIP). In this procedure, the resistance to urine flow is reduced by making one or more incisions in the prostate gland in the region where the urethra meets the urinary bladder. This procedure is performed under general or spinal anesthesia. In this procedure, one or more incisions are made in the muscle of the bladder neck, which is the region where the urethra meets the urinary bladder. The incisions are in most cases are deep enough to cut the surrounding prostate gland tissue including the prostatic capsule. This releases any compression on the bladder neck and causes the bladder neck to spring apart. The incisions can be made using a resectoscope, laser beam etc.

Another example of a surgical procedure for treating BPH symptoms is Laser Prostatectomy. Two common techniques used for Laser Prostatectomy are Visual Laser Ablation of the Prostate (VLAP) and the Holmium Laser Resection/Enucleation of the Prostate (HoLEP). In VLAP, a neodymium:yttrium-aluminum-garnet (Nd:YAG) laser is used to ablate tissue by causing coagulation necrosis. The procedure is performed under visual guidance. In HoLEP, a holmium:Yttrium-aluminum-garnet laser is used for direct contact ablation of tissue. Both these techniques are used to remove tissue obstructing the urethral passage to reduce the severity of BPH symptoms.

Another example of a surgical procedure for treating BPH symptoms is Photoselective Vaporization of the Prostate (PVP). In this procedure, laser energy is used to vaporize prostatic tissue to relieve obstruction to urine flow in the urethra. The type of laser used is the Potassium-Titanyl-Phosphate (KTP) laser. The wavelength of this laser is highly absorbed by oxyhemoglobin. This laser vaporizes cellular water and hence is used to remove tissue that is obstructing the urethra.

Another example of a surgical procedure for treating BPH symptoms is Open Prostatectomy. In this procedure, the prostate gland is surgically removed by an open surgery. This is done under general anesthesia. The prostate gland is removed through an incision in the lower abdomen or the perineum. The procedure is used mostly in patients that have a large (greater than approximately 100 grams) prostate gland.

Minimally invasive procedures for treating BPH symptoms include Transurethral Microwave Thermotherapy (TUMT), Transurethral Needle Ablation (TUNA), Interstitial Laser Coagulation (ILC), and Prostatic Stents.

In Transurethral Microwave Thermotherapy (TUMT), microwave energy is used to generate heat that destroys hyperplastic prostate tissue. This procedure is performed under local anesthesia. In this procedure, a microwave antenna is inserted in the urethra. A rectal thermosensing unit is inserted into the rectum to measure rectal temperature. Rectal temperature measurements are used to prevent overheating of the anatomical region. The microwave antenna is then used to deliver microwaves to lateral lobes of the prostate gland. The microwaves are absorbed as they pass through prostate tissue. This generates heat which in turn destroys the prostate tissue. The destruction of prostate tissue reduces the degree of squeezing of the urethra by the prostate gland thus reducing the severity of BPH symptoms.

Another example of a minimally invasive procedure for treating BPH symptoms is Transurethral Needle Ablation (TUNA). In this procedure, heat induced coagulation necrosis of prostate tissue regions causes the prostate gland to shrink. It is performed using local anesthetic and intravenous or oral sedation. In this procedure, a delivery catheter is inserted into the urethra. The delivery catheter comprises two radiofrequency needles that emerge at an angle of 90 degrees from the delivery catheter. The two radiofrequency needles are aligned at an angle of 40 degrees to each other so that they penetrate the lateral lobes of the prostate. A radiofrequency current is delivered through the radiofrequency needles to heat the tissue of the lateral lobes to 70-100 degree Celsius at a radiofrequency power of approximately 456 KHz for approximately 4 minutes per lesion. This creates coagulation defects in the lateral lobes. The coagulation defects cause shrinkage of prostatic tissue which in turn reduces the degree of squeezing of the urethra by the prostate gland thus reducing the severity of BPH symptoms.

Another example of a minimally invasive procedure for treating BPH symptoms is Interstitial Laser Coagulation (ILC). In this procedure, laser induced necrosis of prostate tissue regions causes the prostate gland to shrink. It is performed using regional anesthesia, spinal or epidural anesthesia or local anesthesia (periprostatic block). In this procedure, a cystoscope sheath is inserted into the urethra and the region of the urethra surrounded by the prostate gland is inspected. A laser fiber is inserted into the urethra. The laser fiber has a sharp distal tip to facilitate the penetration of the laser scope into prostatic tissue. The distal tip of the laser fiber has a distal-diffusing region that distributes laser energy 360° along the terminal 3 mm of the laser fiber. The distal tip is inserted into the middle lobe of the prostate gland and laser energy is delivered through the distal tip for a desired time. This heats the middle lobe and causes laser induced necrosis of the tissue around the distal tip. Thereafter, the distal tip is withdrawn from the middle lobe. The same procedure of inserting the distal tip into a lobe and delivering laser energy is repeated with the lateral lobes. This causes tissue necrosis in several regions of the prostate gland which in turn causes the prostate gland to shrink. Shrinkage of the prostate gland reduces the degree of squeezing of the urethra by the prostate thus reducing the severity of BPH symptoms.

Another example of a minimally invasive procedure for treating BPH symptoms is implanting Prostatic Stents. In this procedure, the region of urethra surrounded by the prostate is mechanically supported to reduce the constriction caused by an enlarged prostate. Prostatic stents are flexible devices that are expanded after their insertion in the urethra. They mechanically support the urethra by pushing the obstructing prostatic tissue away from the urethra. This reduces the constriction of the urethra and improves urine flow past the prostate gland thereby reducing the severity of BPH symptoms.

Although existing treatments provide some relief to the patient from symptoms of BPH, they have disadvantages. Alpha-1a-adrenergic receptors blockers have side effects such as dizziness, postural hypotension, lightheadedness, asthenia and nasal stuffiness. Retrograde ejaculation can also occur. 5-alpha-reductase inhibitors have minimal side effects, but only a modest effect on BPH symptoms and the flow rate of urine. In addition, anti-androgens, such as 5-alpha-reductase, require months of therapy before LUTS improvements are observed. Surgical treatments of BPH carry a risk of complications including erectile dysfunction; retrograde ejaculation; urinary incontinence; complications related to anesthesia; damage to the penis or urethra, need for a repeat surgery etc. Even TURP, which is the gold standard in treatment of BPH, carries a high risk of complications. Adverse events associated with this procedure are reported to include retrograde ejaculation (65% of patients), post-operative irritation (15%), erectile dysfunction (10%), need for transfusion (8%), bladder neck constriction (7%), infection (6%), significant hematuria (6%), acute urinary retention (5%), need for secondary procedure (5%), and incontinence (3%) Typical recovery from TURP involves several days of inpatient hospital treatment with an indwelling urethral catheter, followed by several weeks in which obstructive symptoms are relieved but there is pain or discomfort during micturition.

The reduction in the symptom score after minimally invasive procedures is not as large as the reduction in symptom score after TURP. Up to 25% of patients who receive these minimally invasive procedures ultimately undergo a TURP within 2 years. The improvement in the symptom score generally does not occur immediately after the procedure. For example, it takes an average of one month for a patient to notice improvement in symptoms after TUMT and 1.5 months to notice improvement after ILC. In fact, symptoms are typically worse for these therapies that heat or cook tissue, because of the swelling and necrosis that occurs in the initial weeks following the procedures. Prostatic stents often offer more immediate relief from obstruction but are now rarely used because of high adverse effect rates. Stents have the risk of migration from the original implant site (up to 12.5% of patients), encrustation (up to 27.5%), incontinence (up to 3%), and recurrent pain and discomfort. In published studies, these adverse effects necessitated 8% to 47% of stents to be explanted. Overgrowth of tissue through the stent and complex stent geometries have made their removal quite difficult and invasive.

Thus the most effective current methods of treating BPH carry a high risk of adverse effects. These methods and devices either require general or spinal anesthesia or have potential adverse effects that dictate that the procedures be performed in a surgical operating room, followed by a hospital stay for the patient. The methods of treating BPH that carry a lower risk of adverse effects are also associated with a lower reduction in the symptom score. While several of these procedures can be conducted with local analgesia in an office setting, the patient does not experience immediate relief and in fact often experiences worse symptoms for weeks after the procedure until the body begins to heal. Additionally all device approaches require a urethral catheter placed in the bladder, in some cases for weeks. In some cases catheterization is indicated because the therapy actually causes obstruction during a period of time post operatively, and in other cases it is indicated because of post-operative bleeding and potentially occlusive clot formation. While drug therapies are easy to administer, the results are suboptimal, take significant time to take effect, and often entail undesired side effects.

Urinary Incontinence (UI)

Many women experience loss of bladder control following childbirth or in old age. This condition is broadly referred to as urinary incontinence (UI). The severity of UI varies and, in severe cases, the disorder can be totally debilitating, keeping the patient largely homebound. It is usually associated with a cystocele, which results from sagging of the neck of the urinary bladder into or even outside the vagina.

The treatments for UI include behavioral therapy, muscle strengthening exercises (e.g., Kegel exercises), drug therapy, electrical stimulation of the pelvic nerves, use of intravaginal devices and surgery.

In severe cases of UI, surgery is generally the best treatment option. In general, the surgical procedures used to treat UI attempt to lift and support the bladder so that the bladder and urethra are returned to their normal positions within the pelvic cavity. The two most common ways of performing these surgeries is through incisions formed in the abdominal wall or though the wall of the vagina.

A number of different surgical procedures have been used to treat UI. The names for these procedures include the Birch Procedure, Marshall-Marchetti Operation, MMK, Pubo-Vaginal Sling, Trans-Vaginal Tape Procedure, Urethral Suspension, Vesicourethral Suspension. These procedures generally fall into two categories, namely a) retropubic suspension procedures and b) sling procedures.

In retropubic suspension procedures, an incision is typically made in the abdominal wall a few inches below the navel and a network of sutures are placed to support the bladder neck. The sutures are anchored to the pubic bone and to other structures within the pelvis, essentially forming a cradle which supports the urinary bladder.

In sling procedures, an incision is typically made in the wall of the vagina and a sling is crafted of either natural tissue or synthetic (man-made) material to support the bladder neck. Both ends of the sling may be attached to the pubic bone or tied in front of the abdomen just above the pubic bone. In some sling procedures a synthetic tape is used to form the sling and the ends of the synthetic tape are not tied but rather pulled up above the pubic bone.

The surgeries used to treat UI are generally associated with significant discomfort as the incisions heal and may require a Foley or supra-pubic urinary catheter to remain in place for at least several days following the surgery. Thus, there exists a need in the art for the development of minimally invasive (e.g., non-incisional) procedures for the treatment of UI with less postoperative discomfort and less requirement for post-surgical urinary catheterization.

Cosmetic or Reconstructive Tissue Lifting and Repositioning

Many cosmetic or reconstructive surgical procedures involve lifting, compressing or repositioning of natural tissue, natural tissue or artificial grafts or aberrant tissue. For example, surgical procedures such as face lifts, brow lifts, neck lifts, tummy tucks, etc. have become commonplace. In many cases, these procedures are performed by creating incisions through the skin, dissecting to a plane beneath muscles and fascia, freeing the muscles, fascia and overlying skin from underlying structures (e.g., bone or other muscles), lifting or repositioning the freed muscles, fascia and overlying skin and then attaching the repositioned tissues to underlying or nearby structures (e.g., bone, periostium, other muscles) to hold the repositioned tissues in their new (e.g., lifted) position. In some cases excess skin may also be removed during the procedure.

There have been attempts to develop minimally invasive devices and methods for cosmetic lifting and repositioning of tissues. For example, suture suspension lifts have been developed where one end of a standard or modified suture thread is attached to muscle and the other end is anchored to bone, periostium or another structure to lift and reposition the tissues as desired. Some of these suture suspension techniques have been performed through cannulas or needles inserted though relatively small incisions of puncture wounds.

For example, barbed threads known as Aptos threads may be inserted through a hollow trocar and used to lift tissues of the face in a procedure that is performed commercially under the name Featherlift™ (KMI, Inc. 2550 West Rowland Anaheim, Calif. 92804).

Another barbed thread that is useable for minimally invasive cosmetic lifting procedures is marketed under the name Contour Threads™ (Surgical Specialties Corporation, 100 Dennis Drive Reading, Pa. 19606).

There remains a need for the development of new devices and methods that may be used for various procedures where it is desired to lift, compress, support or reposition tissues or organs within the body with less intraoperative trauma, less post-operative discomfort and/or shorter recovery times.

SUMMARY OF THE INVENTION

The present invention provides systems and methods for retracting, lifting, compressing, supporting or repositioning an organ or tissue within the body of a human or animal subject. In these systems and methods a first anchoring member (e.g., a distal anchor) is positioned at a first location, a second anchoring member (e.g., a proximal anchor) is positioned at a second location and a connector (e.g., an elongate connector, tensioning member, filament, strand, thread, suture thread, string, wire, semi-rigid member, flexible member, elastic member, non-elastic member, resilient member, plastically deformable member, etc.) extends between the first and second anchoring members with a sufficient distance or tension to bring about the desired retracting, lifting, compressing, supporting or repositioning of the organ or tissue. In some applications of the invention, the invention may be used to facilitate volitional or non-volitional flow of a body fluid through a body lumen, modify the size or shape of a body lumen or cavity, treat prostate enlargement, treat urinary incontinence, support or maintain positioning of a tissue, organ or graft, perform a cosmetic lifting or repositioning procedure, form anastomotic connections, and/or treat various other disorders where a natural or pathologic tissue or organ is pressing on or interfering with an adjacent anatomical structure. Also, the invention has a myriad of other potential surgical, therapeutic, cosmetic or reconstructive applications, such as where a tissue, organ, graft or other material requires retracting, lifting, repositioning, compression or support.

Further in accordance with the invention, in some embodiments, a first (e.g., distal) anchor having the connector attached thereto is implanted at a first location within the subject's body. A second anchor (e.g., proximal) is then advanced over the connector to a second location where it is affixed to the connector such that the connector is under tension and thereby retracts, lifts, compresses, supports or repositions said organ or tissue. Any excess or residual portion of the connector may then be cut and removed. This embodiment of the invention may be used, for example, to treat enlargement of the prostate gland. When used to treat enlargement of the prostate gland, a first introducer may be inserted into the subject's urethra and a penetrator (e.g., a needle) may be advanced from the first introducer, through the wall of the urethra and into or through the prostate (e.g., at an extracapsular location outside of the prostate's connective tissue capsule, at an intracapsular location within the prostate capsule or at a sub-capsular location within the paryenchyma of the prostate). The first anchor (with the connector attached thereto) is then deployed from the penetrator such that it becomes implanted at the desired first location. The penetrator may be retracted into the first introducer and the first introducer may be removed from the subject's urethra, leaving the connector trailing from the implanted first anchor, through the penetration tract created by the penetrator and into (or all the way out of) the subject's urethra. A second introducer bearing the second anchor may then be advanced over the trailing portion of the connector to a second location where it is affixed to the connector to compress prostate tissue between the first and second anchors or otherwise reposition the prostate tissue so as to decrease compression of the urethra, thereby allowing normal or improved micturition while avoiding substantial resection or cutting of the urethral wall or prostate gland. In some applications, multiple sets of tissue anchors may be placed at different locations to reposition the lobes of the prostate. In other cases, more than two anchors may be attached to a single connector such that more than two anchoring locations are established on that connector.

Still further in accordance with the invention, there are provided introducer-delivery devices useable to install the tissue retracting, lifting, compressing, supporting or repositioning systems of the foregoing character. In some embodiments, device for delivering the first (e.g., distal) anchor may comprise an elongate shaft that is insertable into a lumen or cavity of the subject's body and a penetrator (e.g., a needle) that is advanceable from the elongate shaft such that the penetrator penetrates into or through tissue. After the penetrator has been advanced, the first (e.g., distal) anchor is deployed from the penetrator such that it becomes implanted at the desired first location within the subject's body. A handpiece may be provided on the proximal end of the elongate shaft. Such handpiece may incorporate one or more actuators (e.g., triggers or other controls) for a) advancing/retracting the penetrator and b) deploying the first (e.g., distal) anchor from the penetrator. In some embodiments, a delivery device for delivering the second (e.g., proximal) anchor may comprise an elongate shaft with a mechanism that holds the second (e.g., proximal) anchor. After the free end of the connector has been inserted into the passageway of the second anchor, the elongate shaft bearing the second anchor is advanced into the body lumen or cavity such that the second (e.g., proximal) anchor tracks over the connector and becomes cinched up to the desired second position. Then the second anchor is affixed to the connector at such second position and released from the elongate shaft. Any residual or protruding connector may be cut and the elongate shaft may then be removed from the body lumen or cavity, leaving the first (e.g., distal) anchor, connector and second (e.g., proximal) anchor in place. A handpiece may be provided on the proximal end of this elongate member. Such handpiece may incorporate one or more actuators (e.g., triggers or other controls) for a) affixing (e.g., locking) the second anchor into the connector, b) releasing the second anchor from the elongate shaft and c) optionally cutting away any residual portion of the connector.

Still further aspects and elements of the invention will become apparent to those of skill in the art upon reading of the detailed description and examples set forth herebelow.

BRIEF DESCRIPTION OF THE DRAWINGS

FIG. 3A' shows a perspective view of an embodiment of a second elongate part that is used to construct the distal end of the embodiment of the distal anchor delivery device of FIG. 3Y.

FIGS. 4A and 4B show longitudinal sections through a first embodiment of a proximal anchor showing the steps of an embodiment of a method of attaching the proximal anchor to a connector.

FIG. 4C shows a first embodiment of a flat pattern that can be used to design the proximal anchor of FIG. 4A.

FIGS. 4D and 4E show longitudinal sections through a second embodiment of a proximal anchor showing the steps of an embodiment of a method of attaching the proximal anchor to a connector.

FIGS. 4F and 4G show longitudinal sections through a third embodiment of a proximal anchor showing the steps of an embodiment of a method of attaching the proximal anchor to a connector.

FIG. 4H shows an embodiment of a flat pattern that can be used to design the proximal anchor of FIGS. 4F and 4G.

FIGS. 4I and 4J show longitudinal sections through a fourth embodiment of a proximal anchor showing the steps of an embodiment of a method of attaching the proximal anchor to a connector.

FIGS. 4K and 4L show longitudinal sections through a proximal anchor showing the steps of an embodiment of a method of anchoring a connector to a proximal anchor by an elongate wedging device comprising multiple branches or bristles.

FIGS. 4M and 4N show longitudinal sections through an embodiment of a proximal anchor showing the steps of an embodiment of a method of anchoring a connector to a proximal anchor by a lock pin pulled by a flexible pull shaft.

FIGS. 4O and 4P show longitudinal sections through an embodiment of a proximal anchor showing the steps of an embodiment of a method of anchoring a connector to the proximal anchor by a hollow wedging element.

FIGS. 4Q and 4R show an embodiment of a method of using a compression cutter for cutting the excess length of a connector and a wedging element.

FIGS. 4S and 4T show longitudinal sections through a first embodiment of a proximal anchor comprising a crimping zone showing the steps of an embodiment of a method of anchoring a connector to the proximal anchor.

FIGS. 4U and 4V show longitudinal sections through a second embodiment of a proximal anchor comprising a crimping zone showing the steps of an embodiment of a method of anchoring a connector to the proximal anchor.

FIGS. 4W and 4X show a third embodiment of a proximal anchor comprising multiple crimping zones showing the steps of an embodiment of a method of anchoring a connector to the proximal anchor.

FIG. 4Y shows a side view of an embodiment of a proximal anchor comprising a tapering outer surface.

FIGS. 4Z through 4AB show side views of the embodiment of the proximal anchor of FIG. 4Y showing the steps of an embodiment of a method of anchoring a connector to the proximal anchor by an anchoring ring.

FIG. 4AC shows a cross sectional view of an embodiment of the cutting ring of FIGS. 4M and 4AB.

FIG. 4AD shows a side view of a first embodiment of a proximal anchor made of a thermal shape memory alloy.

FIG. 4AE shows a cross section of the proximal anchor of FIG. 4AD through the line 4AE-4AE when the shape memory material of the proximal anchor is in the martensite phase.

FIG. 4AE' shows a cross section of the proximal anchor of FIG. 4AD through the line 4AE-4AE when the shape memory material of the proximal anchor is in the programmed shape.

FIG. 4AF shows a cross section of the proximal anchor of FIG. 4AD through the line 4AF-4AF when the shape memory material of the proximal anchor is in the martensite phase.

FIG. 4AF' shows a cross section of the proximal anchor of FIG. 4AD through the line 4AF-4AF when the shape memory material of the proximal anchor is in the programmed shape.

FIG. 4AG shows a side view of a second embodiment of a proximal anchor made of a thermal shape memory alloy.

FIG. 4AH shows a cross section of the proximal anchor of FIG. 4AG through the line 4AH-4AH when the shape memory material of the proximal anchor is in the martensite phase.

FIG. 4AH' shows a cross section of the proximal anchor of FIG. 4AG through the line 4AH-4AH when the shape memory material of the proximal anchor is in the programmed shape.

FIGS. 4AI and 4AJ show longitudinal sections of an embodiment of a proximal anchor showing the steps of an embodiment of a method of anchoring a looped or folded region of the connector to the proximal anchor.

FIG. 4AK shows a side view of an embodiment of a proximal anchor made of a suitable elastic or super elastic or shape memory material comprising one or more inwardly opening flaps.

FIG. 4AL shows a longitudinal section through the embodiment of the proximal anchor of FIG. 4AK.

FIGS. 7A through 7H show a longitudinal section of a tubular organ showing the steps of a method of reducing the cross sectional area of the lumen of the tubular organ.

FIG. 7I shows a schematic diagram of a tubular organ showing the configuration of the tubular organ before performing the method shown in FIGS. 7A through 7H.

FIG. 7J shows a schematic diagram of the tubular organ of FIG. 7I showing a possible configuration obtained after performing the method shown in FIGS. 7A through 7H.

FIG. 7K shows an embodiment of a distal anchor delivery device comprising a helical needle.

FIGS. 7W through 7Y shows cross sections of a tubular organ showing the steps of a first embodiment of a method of reducing the cross sectional area of the lumen of the tubular organ by implanting a device that pinches the walls of the tubular organ to create a recess.

FIGS. 7Z through 7AD show cross sections of a tubular organ showing the steps of a second embodiment of a method of reducing the cross sectional area of the lumen of the tubular organ by implanting a device that pinches the walls of the tubular organ to create a recess.

FIG. 7AE shows a cross section of a tubular organ showing the steps of a first embodiment of a method of reducing the cross sectional area of the lumen of the tubular organ by implanting devices that pinch the walls of the tubular organ to create two recesses.

FIG. 7AF shows a cross section of a tubular organ showing a step of a second embodiment of a method of reducing the cross sectional area of the lumen of the tubular organ by implanting devices that pinch the walls of the tubular organ to create two recesses.

FIG. 7AG shows a cross section of a tubular organ showing a method of reducing the cross sectional area of the lumen of the tubular organ by creating a recess in the walls of the tubular organ and reinforcing the recessed region.

FIG. 8A shows an anchoring system implanted in a stomach to reduce the volume of the stomach to treat obesity.

FIG. 8B shows a cross sectional view of a stomach before implanting an anchoring system to reduce the volume of the stomach.

FIG. 8C shows a cross sectional view of the stomach of FIG. 8B after implanting an anchoring system to reduce the volume of the stomach.

FIG. 8D shows a section through wound edges closed by an anchoring system in a first configuration.

FIG. 8E shows a section through wound edges closed by an anchoring system in a second configuration.

FIG. 8F shows an anchoring device used to reconnect torn tissues of the musculoskeletal system.

FIG. 8G shows a sagittal section through the head of a patient suffering from sleep apnea.

FIG. 8H shows a sagittal section through the head of a patient suffering from sleep apnea who has been treated with two anchoring devices that displace the obstructing portions of the soft palate SP and the tongue To.

FIG. 8I shows an anchoring system that is implanted to lift loose skin in the face of a human.

FIG. 8J shows a view of a human face showing facial regions that may be treated by a method similar to the method shown in FIG. 8I to improve the cosmetic appearance of the human.

FIG. 8K shows a sagittal section through the lower abdomen of a human female showing an embodiment of a method of treating female urinary incontinence by a sling attached to the anatomy by anchoring devices.

FIG. 8L shows a cross section of a normal urethra UT.

FIG. 8M shows a cross section of the urethra UT in a human female suffering from stress urinary incontinence.

FIG. 8N shows a cross section of the urethra UT in a human female suffering from stress urinary incontinence where the urethra UT has been supported with a sling.

FIG. 8O shows a section through the lower abdomen of a human female suffering from stress urinary incontinence where the urethra UT has been supported with a sling.

FIG. 8P shows a section through the lower abdomen showing an embodiment of a colposuspension procedure wherein one or more regions of the vaginal wall of a patient suffering from incontinence are suspended to the Cooper's ligament by one or more anchoring devices.

FIG. 8Q shows an anchoring device used to attach a seal to a puncture site on a blood vessel BV to seal the puncture site.

FIG. 8R shows a view of the pectoral region of a human female.

FIG. 8S shows the pectoral region of a human female wherein mastopexy has been performed on one or more regions of the breasts using the anchoring devices disclosed herein.

DETAILED DESCRIPTION

The following detailed description and the accompanying drawings are intended to describe some, but not necessarily all, examples or embodiments encompassed by the present invention.

A number of the drawings in this patent application show anatomical structures of the male reproductive and/or urinary system. In general, these anatomical structures are labeled with the following reference letters:

| | |
|---|---|
| Urethra | UT |
| Urinary Bladder | UB |
| Prostate Gland | PG |
| Target Tissue | TT |
| Urethral Wall | UW |
| Ligament | Li |
| Bone | Bo |
| Pubic Bone | PB |
| Soft Palate | SP |
| Tongue | To |
| Rectum | R |
| Vagina | V |
| Blood Vessel | BV |

Figure 1:
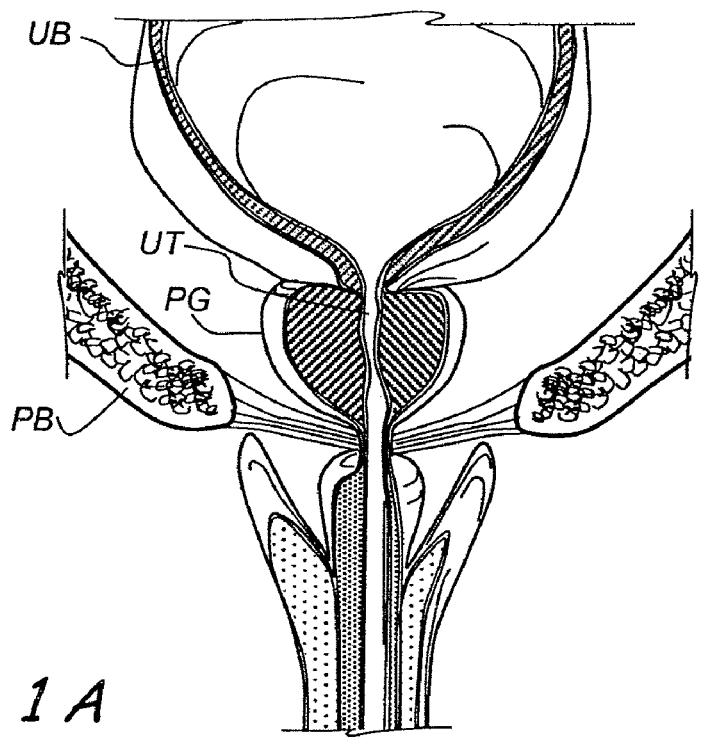
FIG. 1A shows a coronal section through the lower abdomen of a male human suffering from BPH showing a hypertrophied prostate gland.
FIG. 1B shows a coronal section through the lower abdomen of a male human suffering from BPH showing a hypertrophied prostate gland treated with an embodiment of the device of the present invention.
FIG. 1C shows a side view of an embodiment of the retractor shown in FIG. 1B.
FIGS. 1D through 1J show the various steps of a method of treating a prostate gland by the retractor shown in FIG. 1C.
Figure 1:
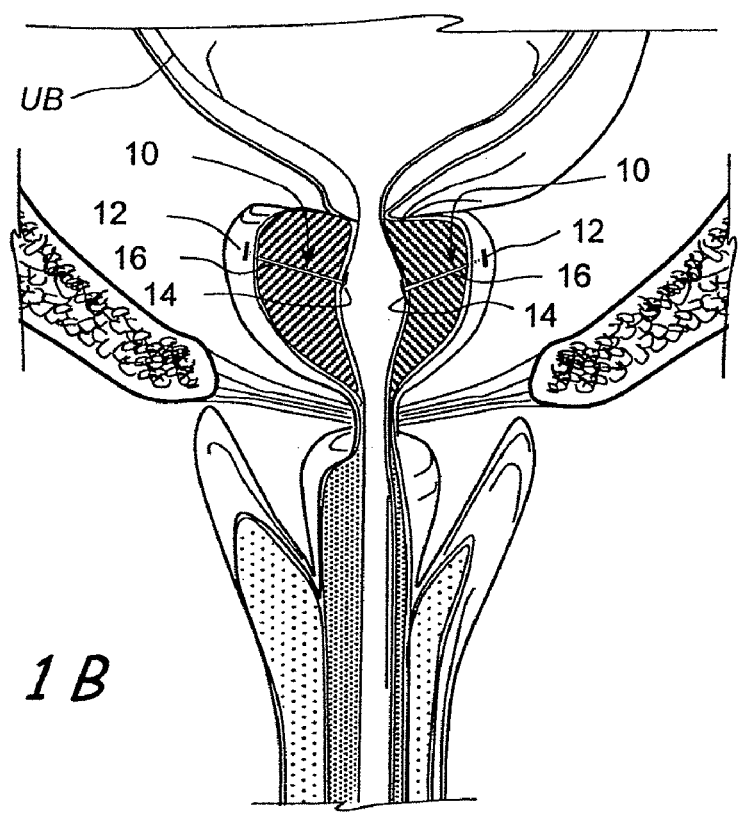

FIG. 1A shows a coronal section (i.e., a section cut approximately in the plane of the coronal suture or parallel to it) through the lower abdomen of a male human suffering from BPH showing a hypertrophied prostate gland. As depicted in FIG. 1A, the urinary bladder UB is a hollow muscular organ that temporarily stores urine. It is situated behind the pubic bone PB. The lower region of the urinary bladder has a narrow muscular opening called the bladder neck which opens into a soft, flexible, tubular organ called the urethra UT. The muscles around the bladder neck are called the internal urethral sphincter. The internal urethral sphincter is normally contracted to prevent urine leakage. The urinary bladder gradually fills with urine until full capacity is reached, at which point the sphincters relax. This causes the bladder neck to open, thereby releasing the urine stored in the urinary bladder into the urethra. The urethra conducts urine from the urinary bladder to the exterior of the body. The urethra begins at the bladder neck and terminates at the end of the penis. The prostate gland PG is located around the urethra at the union of the urethra and the urinary bladder. In FIG. 1A, the prostate gland is hypertrophied (enlarged). This causes the prostate gland to press on a region of the urethra. This in turn creates an undesired obstruction to the flow of urine through the urethra.

FIG. 1B shows a coronal section through the lower abdomen of a male human suffering from BPH showing a hypertrophied prostate gland treated with an embodiment of the device of the present invention. It has been discovered that the enlarged prostate gland is compressible and can be retracted so as to relieve the pressure from the urethra. In accordance with one embodiment of the present invention, a retractor device can be placed through the prostate gland in order to relieve the pressure on the urethra. In FIG. 1B, a retractor 10 is implanted in the prostate gland. Retractor 10 comprises a distal anchor 12 and a proximal anchor 14. Distal anchor 12 and a proximal anchor 14 are connected by a connector 16. The radial distance from the urethra to distal anchor 12 is greater than the radial distance from the urethra to proximal anchor 14. The distance or tension between the anchors is sufficient to compress, displace or change the orientation of an anatomical region between distal anchor 12 and proximal anchor 14. The connector 16 can be inelastic so as to maintain a constant force or distance between the proximal and distal anchors or be elastic so as to attempt to draw the proximal and distal anchors closer together. In the embodiment shown in FIG. 1B, distal anchor 12 is located on the outer surface of the capsule of prostate gland CP and acts as a capsular anchor. Alternatively, distal anchor 12 may be embedded inside the tissue of prostate gland PG or in the surrounding structures around the prostate such as periosteum of the pelvic bones, within the bones themselves, pelvic fascia, coopers ligament, muscles traversing the pelvis or bladder wall. Also, in the embodiment shown in FIG. 1B, proximal anchor 14 is located on the inner wall of urethra UT and acts as a urethral anchor. Alternatively, proximal anchor 14 may be embedded inside the tissue of prostate gland PG or surrounding structures as outlined above. Distal anchor 12 and proximal anchor 14 are implanted in the anatomy such that a desired distance or tension is created in connector 16. This causes distal anchor 12 and proximal anchor 14 to retract or compress a region of prostate gland PG to relieve the obstruction shown in FIG. 1A. In FIG. 1B, two retractors 10 are implanted in prostate gland PG. Each retractor 10 is implanted in a lateral lobe (side lobe) of prostate gland PG. The various methods and devices disclosed herein may be used to treat a single lobe or multiple lobes of the prostate gland or other anatomical structures. Similarly, two or more devices disclosed herein may be used to treat a single anatomical structure. For example, a lateral lobe of prostate gland PG may be treated using two retractors 10. One or more retractors may be deployed at particular angles to the axis of the urethra to target one or more lateral lobes and/or middle lobe of the prostate gland. In one embodiment, retractor 10 is deployed between the 1 o'clock and 3 o'clock position relative to the axis of the urethra to target the left lateral lobe of the prostate gland. In another embodiment, retractor 10 is deployed between the 9 o'clock and 11 o'clock position relative to the axis of the urethra to target the right lateral lobe of the prostate gland. In another embodiment, retractor 10 is deployed between the 4 o'clock and 8 o'clock position relative to the axis of the urethra to target the middle lobe of the prostate gland.

Figure 1C:
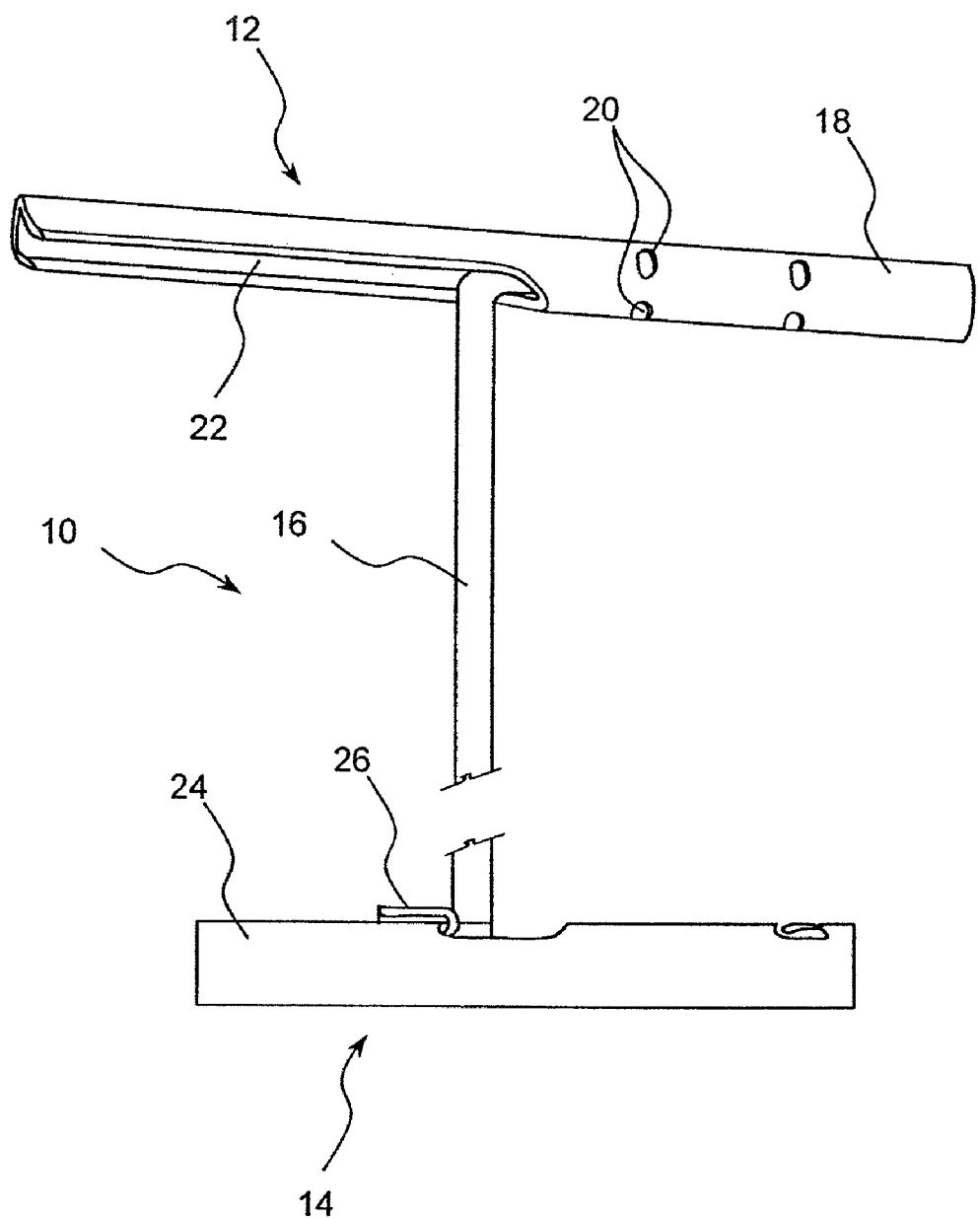
Figure 1:
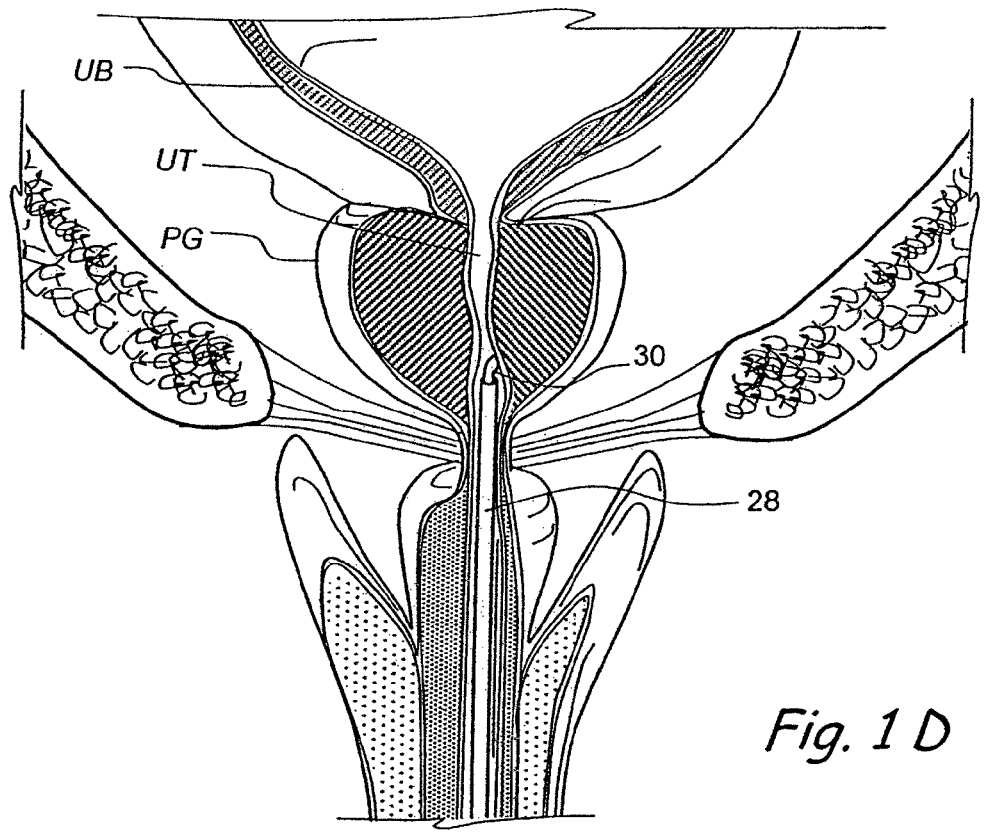
Figure 1:
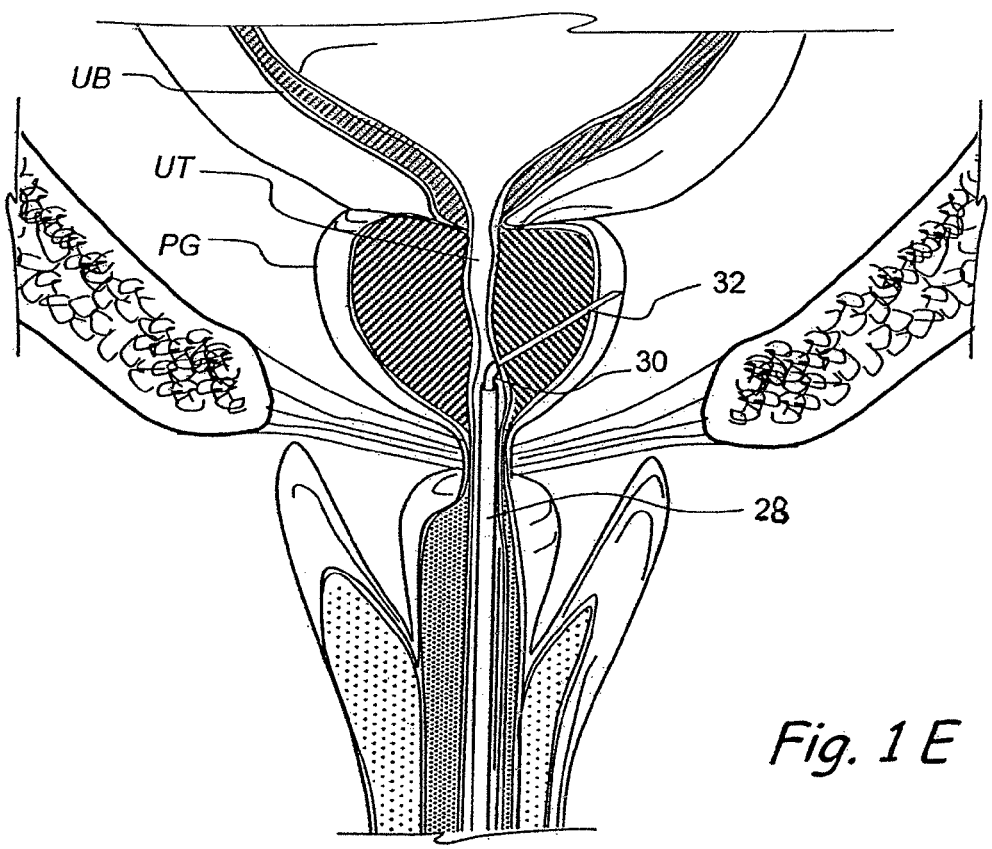
Figure 1:
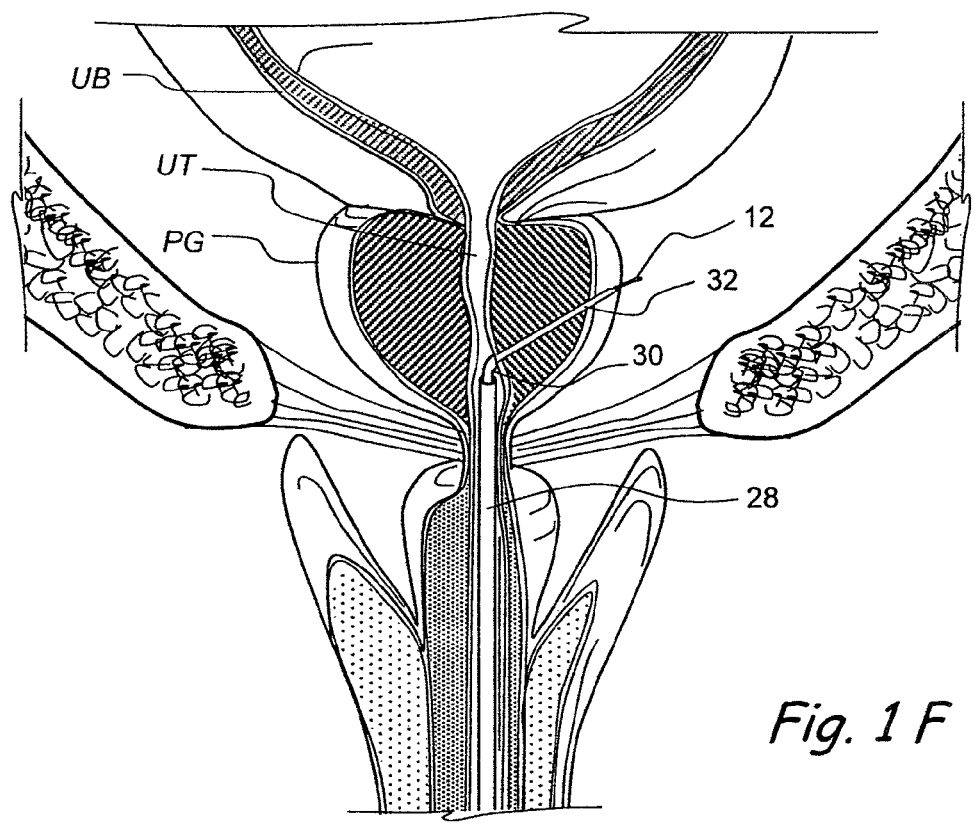
Figure 1:
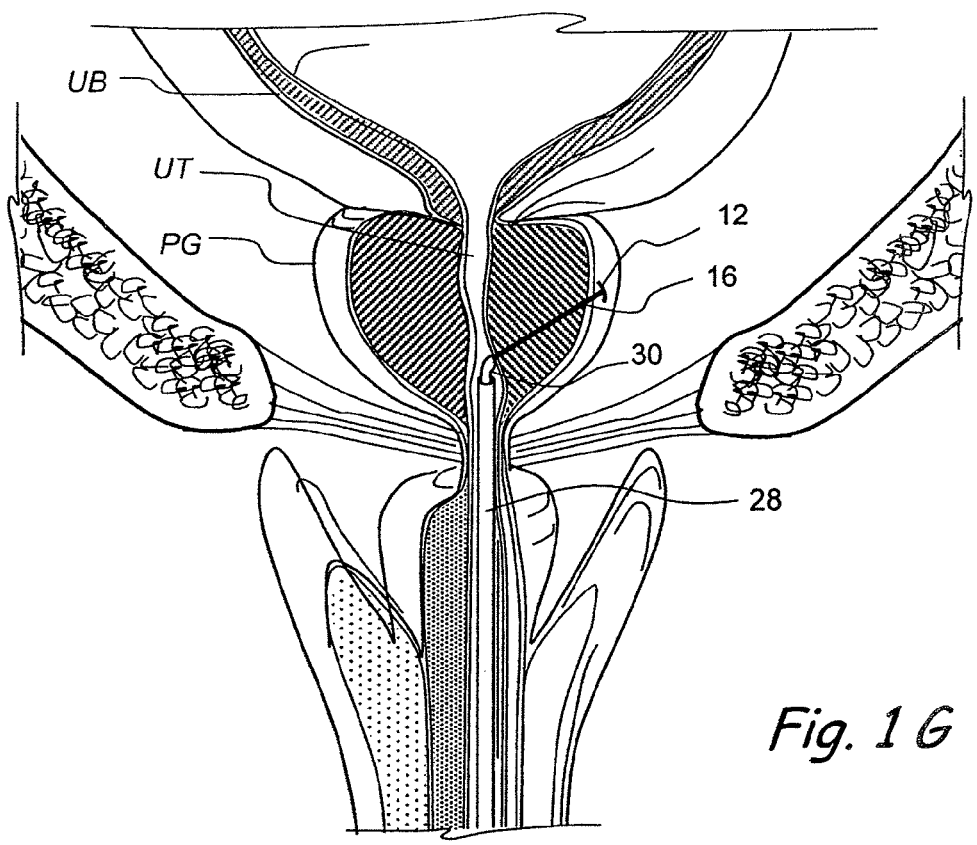

FIG. 1C shows a side view of one embodiment of the retractor shown in FIG. 1B. FIG. 1C shows retractor 10 comprising distal anchor 12 and proximal anchor 14. Distal anchor 12 and proximal anchor 14 are connected by connector 16. In the embodiment shown in FIG. 1C, distal anchor 12 comprises a tube 18 having a lumen. Tube 18 can be made of suitable elastic or non-elastic materials including, but not limited to metals, polymers, etc. Typical examples of such materials include, but are not limited to stainless steel 304, stainless steel 316, nickel-Titanium alloys, titanium, Pebax, Polyimide, braided Polyimide, Polyurethane, Nylon, PVC, Hytrel, HDPE, PEEK, PTFE, PFA, FEP, EPTFE, shape memory polymers, such as polyesterurethane, polyetherurethane, polyetherpolyesters, polyetherpolyamines or combinations of oligo e-caprolactore diol and oligo p-dioxanone diol polymers, etc. Connector 16 is attached to tube 18. In one embodiment, connector 16 is a USP size 0 polypropylene monofilament suture. In the embodiment shown in FIG. 1C, a distal region of connector 16 is located in the lumen of tube 18 such that the distal tip of connector 16 emerges out of one end of the lumen of tube 18. The distal tip of connector 16 is enlarged, such that the diameter of the enlarged distal tip of connector 16 is greater than the inner diameter of tube 18. In one embodiment, the diameter of connector 16 is 0.014 inches and the diameter of the enlarged distal tip of connector 16 is 0.025 inches. In one embodiment, the enlarged distal tip of connector 16 is created by controlled melting of the distal tip of connector 16. This attaches connector 16 to tube 18. Tube 18 may comprise one or more additional attachment mechanisms to attach a distal region of connector 16 to tube 18. In one embodiment, the distal region of connector 16 is attached to tube 18 by a suitable biocompatible adhesive. In the embodiment shown in FIG. 1C, the distal region of connector 16 is attached to tube 18 by one or more inwardly opening flaps 20 that are cut in the material of tube 18. Flaps 20 grip connector 16 and thus prevent the relative motion of connector 16 and tube 18. The angle between one of flaps 20 and connector 16 may range from 1 degree to 90 degrees. Tube 18 further comprises a longitudinal slot 22. Longitudinal slot 22 extends from one end to roughly the mid section of tube 18. Connector 16 emerges out of this longitudinal slot 22. Thus, when connector 16 is pulled in the proximal direction, distal anchor 12 assumes a T-shape that helps to anchor distal anchor 12 to an anatomical structure. Distal anchor 12 may comprise a sharp edge to help penetrate distal anchor 12 through the anatomy. In a preferred embodiment, distal anchor 12 is constructed by laser cutting an electropolished nickel-titanium alloy (e.g., nitinol) tube made of 50.8% nickel-49.2% titanium. In the preferred embodiment, the outer diameter of tube 18 is 0.026 inches, the inner diameter of tube 18 is 0.015 inches, the length of tube 18 is 0.315 inches and the length of longitudinal slot 22 is 0.170 inches.

In the embodiment shown in FIG. 1C, proximal anchor 14 comprises a tube 24 comprising a lumen. Tube 24 can be made of suitable elastic or non-elastic materials including, but not limited to metals, polymers, etc. Typical examples of such materials include, but are not limited to stainless steel 304, stainless steel 316, nickel-Titanium alloys, titanium, Pebax, Polyimide, braided Polyimide, Polyurethane, Nylon, PVC, Hytrel, HDPE, PEEK, PTFE, PFA, FEP, ePTFE, such as polyesterurethane, polyetherurethane, polyetherpolyesters, polyetherpolyamines or combinations of oligo e-caprolactone diol and oligo p-dioxanone diol polymers, etc. An outwardly opening flap 26 is cut through the material of tube 24. Flap 26 is folded on the outer surface of tube 18 as shown in FIG. 1C. This creates an opening to the lumen of tube 24 that is lined by the atraumatic edge of the folded flap 26.

Connector 16 enters tube 24 through this opening to the lumen of tube 24. Proximal anchor 14 further comprises an attachment mechanism to attach connector 16 to tube 24. Connector 16 can be made of suitable elastic or non-elastic materials including, but not limited to metals, polymers, etc. Typical examples of such materials include, but are not limited to stainless steel 304, stainless steel 316, nickel-Titanium alloys, suture materials, titanium, silicone, nylon, polyamide, polyglycolic acid, polypropylene, Pebax, PTFE, ePTFE, silk, gut, or any other braided or mono-filament material. In a preferred embodiment, tube 24 has a length of 0.236 inches and an outer diameter of 0.027 inches and an inner diameter of 0.020 inches. The length of opening to the lumen of tube 24 is approximately 0.055 inches. In the preferred embodiment, the attachment mechanism comprises a lock pin that frictionally attaches connector 16 to tube 24. The lock pin and tube 24 are made of stainless steel 316L. In the preferred embodiment, tube 24 is laser cut and then electropolished. Lock pin is constructed using EDM (electrical discharge machining) and then passivated.

FIGS. 1D through 1J show the various steps of a method of treating a prostate gland by the retractor shown in FIG. 1C. Similar methods may be also used to deploy retractor or compression devices in other anatomical structures. In the step shown in FIG. 1D, a sheath 28 such as a standard resectoscope sheath is introduced into the urethra (trans-urethrally). Sheath 28 is advanced through urethra UT such that the distal end of sheath 28 is positioned near a region of urethra UT that is obstructed by a hypertrophied prostate gland PG. Distal anchor delivery device 30 is introduced through sheath 28. Distal anchor delivery device 30 can be placed in the sheath 28 after the distal end of sheath 28 is positioned near the region of the urethra UT that is obstructed or the distal anchor delivery device 30 can be pre-loaded in the sheath 28 before positioning of the sheath 28. Distal anchor delivery device 30 is advanced through sheath 28 such that the distal end of distal anchor delivery device 30 emerges out of the distal end of sheath 28. Distal anchor delivery device 30 is oriented such that a working channel opening of distal anchor delivery device 30 points towards a lateral lobe of prostate gland PG.

In the step shown in FIG. 1E, a needle 32 is introduced through distal anchor delivery device 30. Needle 32 can be placed in distal anchor delivery device after the distal anchor delivery device 30 is advanced through sheath 28 or the needle 32 can be pre-loaded in the distal anchor delivery device 30. In one embodiment, needle 32 is a 20 gauge needle. Needle 32 is advanced through distal anchor delivery device 30 such that it emerges through the working channel opening. Needle 32 is further advanced such that it penetrates through the tissue of prostate gland PG and the distal end of needle 32 emerges out of the capsule of prostate gland CP.

In the step shown in FIG. 1F, distal anchor 12 connected to connector 16 is advanced through needle 32. Distal anchor 12 can be pre-loaded in needle 32 or can be loaded in needle 32 after needle 32 has been advanced through distal anchor delivery device 30. Distal anchor 12 is advanced through needle 32 such that it emerges out of the distal end of needle 32.

In the step shown in FIG. 1G, needle 32 is removed from distal anchor delivery device 30 by pulling needle 32 in the proximal direction.

Figure 1H:
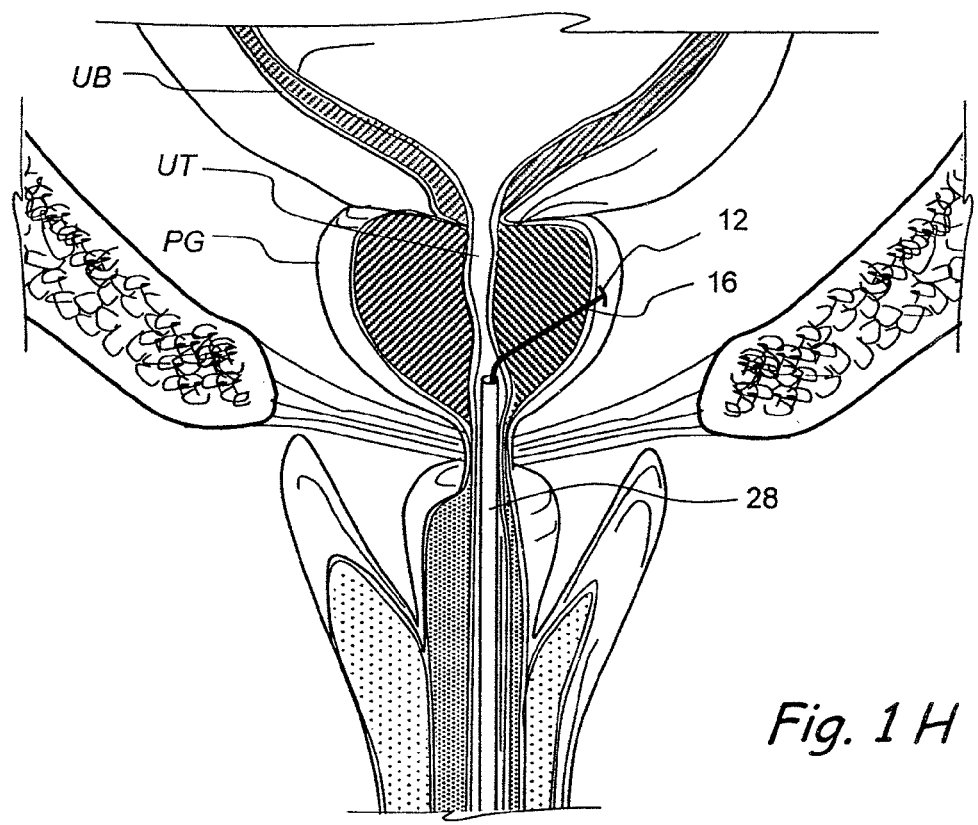

In the step shown in FIG. 1H, distal anchor delivery device 30 is removed from sheath 28 by pulling distal anchor delivery device 30 in the proximal direction. Also, connector 16 is pulled to orient distal anchor 12 perpendicularly to connector 16.

Figure 1I:
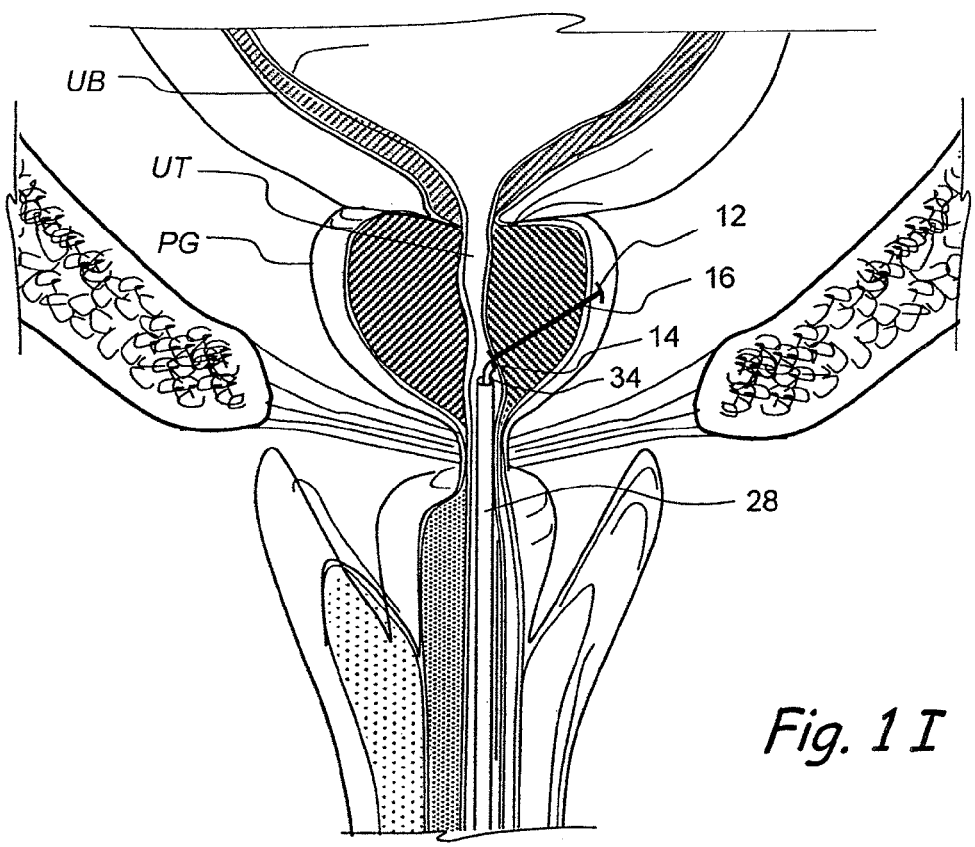

In the step shown in FIG. 1I, connector 16 is passed through proximal anchor 14 located on a proximal anchor delivery device 34. Proximal anchor delivery device 34 is advanced through sheath 28 such that the distal end of proximal anchor delivery device 34 emerges out of the distal end of sheath 28. A desired tension is introduced in connector 16 such that distal anchor 12 is pulled by connector 16 with a desired force. Alternatively, the proximal anchor can be visualized through an endoscope or under fluoroscopy and advanced along the connector until the desired retraction of the tissue is achieved.

Figure 1J:
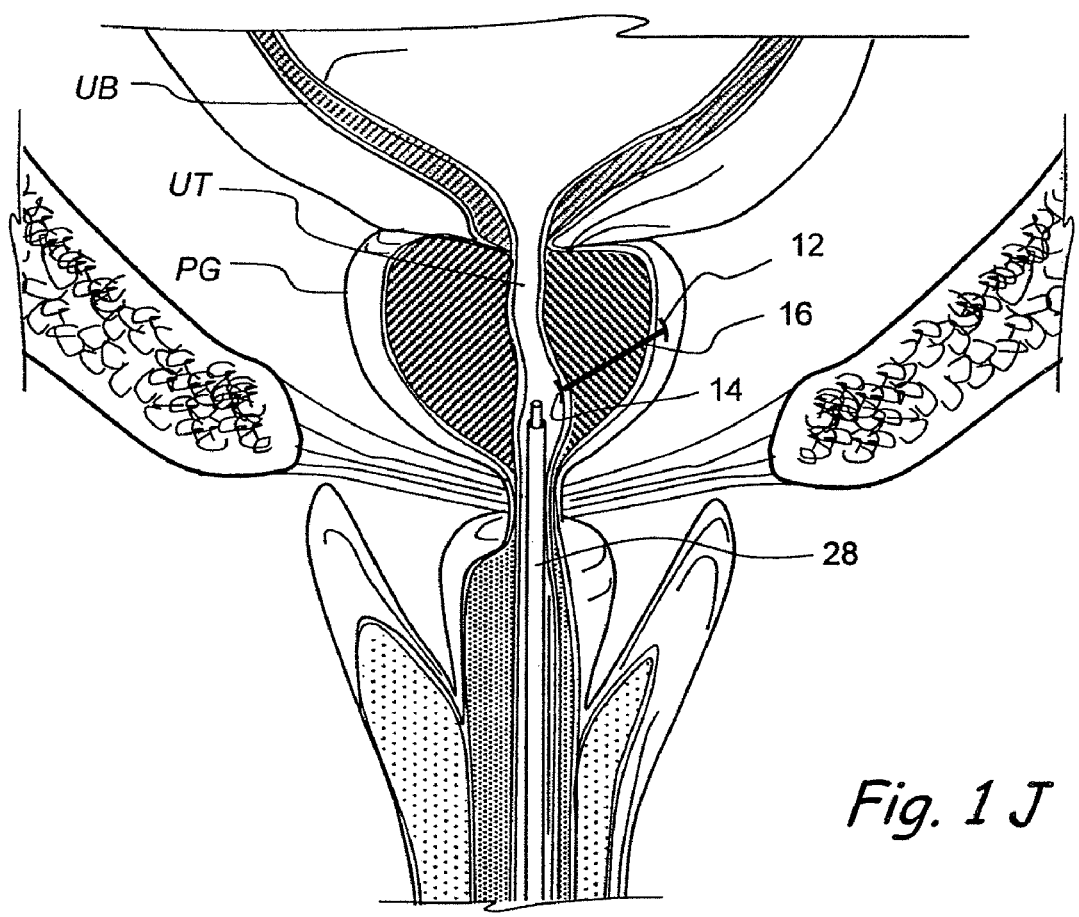

In the step shown in FIG. 1J, connector 16 is attached to proximal anchor 14. Proximal anchor 14 is also released from proximal anchor delivery device 34, thus deploying proximal anchor 14 in the anatomy. Proximal anchor delivery device 34 and sheath 28 are removed form the anatomy. Retractor 10 comprising distal anchor 12, proximal anchor 14 and connector 16 is used to retract, lift, support, reposition or compress a region of prostate gland PG located between distal anchor 12 and proximal anchor 14. This method may be used to retract, lift, support, reposition or compress multiple regions or lobes of the prostate gland PG. In the method shown in FIGS. 1D through 1J, distal anchor 12 is deployed on the outer surface of the capsule of prostate gland CP. Thus, distal anchor 12 acts as a capsular anchor. Alternatively, distal anchor 12 may be deployed inside the tissue of prostate gland PG or beyond the prostate as outlined previously. Similarly, in the method shown in FIGS. 1D through 1J, proximal anchor 14 is deployed on the inner wall of urethra UT and acts as a urethral anchor. Alternatively, proximal anchor 14 may be deployed inside the tissue of prostate gland PG.

Figure 2A:
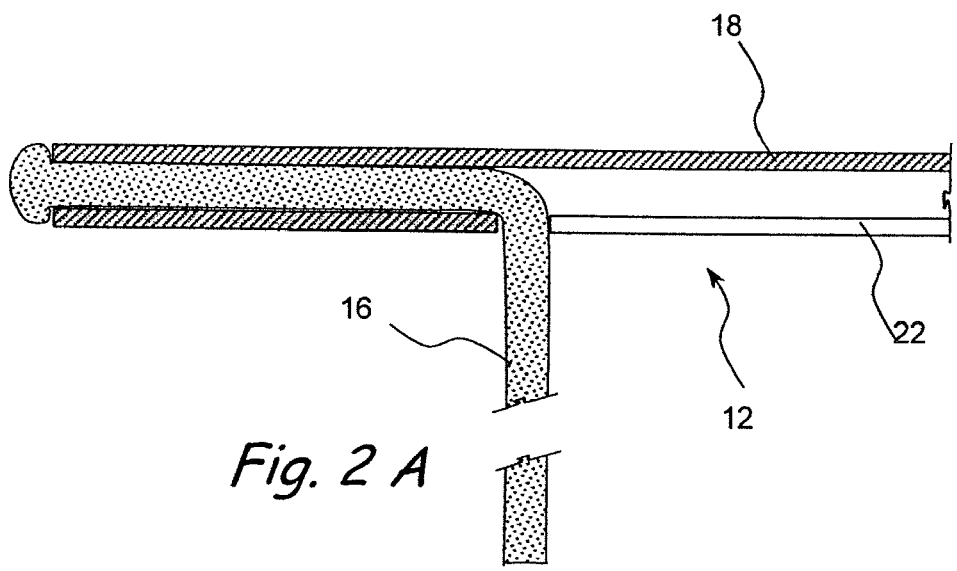
FIG. 2A shows a sectional view through the embodiment of a distal anchor shown in FIG. 1C.

FIG. 2A shows a sectional view through the embodiment of a distal anchor shown in FIG. 1C. In the embodiment shown in FIG. 2A, distal anchor 12 comprises tube 18 comprising a lumen. Tube 18 is attached to a connector 16. In the embodiment shown in FIG. 2A, a distal region of connector 16 is located in the lumen of tube 18 such that the distal tip of connector 16 emerges out of one end of the lumen of tube 18. Distal anchor 12 and/or connector 16 comprise one or more attachment mechanisms to attach distal anchor 12 to connector 16. In the embodiment shown in FIG. 2A, the attachment mechanism comprises an enlarged distal tip of connector 16. In one embodiment, the enlarged distal tip is created by controlled melting of the distal tip of connector 16. The enlarged distal tip anchors connector 16 to tube 18. In another embodiment, the attachment mechanism comprises a suitable biocompatible adhesive that attaches the distal region of connector 16 to tube 18. Other examples of attachment mechanisms include, but are not limited to one or more knots on connector 16, one or more turnbuckles on connector 16, crimped regions of distal anchor 12, additional crimping elements that crimp onto the outer surface of connector 16, or crimping elements that fit inside the tube, etc. Tube 18 further comprises longitudinal slot 22. Longitudinal slot extends from one end to roughly the mid section of tube 18. Connector 16 emerges out of this longitudinal slot 22. Thus, when connector 16 is pulled in the proximal direction, distal anchor 12 assumes a T-shape that helps to anchor distal anchor 12 to an anatomical structure. Distal anchor 12 may comprise a sharp edge to help penetrate distal anchor 12 through the anatomy. In one embodiment, distal anchor 12 comprises a nickel-titanium alloy (e.g., nitinol) tube and connector 16 comprises a polypropylene suture.

Figure 2B:
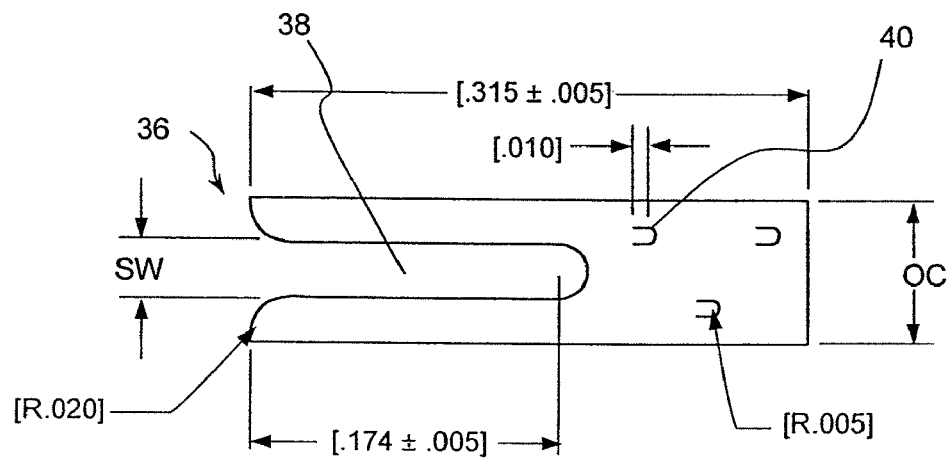
FIG. 2B shows a first embodiment of a flat pattern that can be used to design the distal anchor of FIG. 2A.

In one embodiment of a method of manufacturing distal anchor 12, a tube is laser cut with a radially aligned laser. The geometry of the laser cut pattern is specified using a flat pattern drawing which is mapped onto the outside circumference of the tube. FIG. 2B shows a first embodiment of a flat pattern that can be used to manufacture a distal anchor 12 of FIG. 2A. In FIG. 2B, flat pattern 36 comprises a rectangular region. The length of the rectangular region represents the length of the tube. The width of the rectangular region OC represents the outer circumference of the tube. In one embodiment, the length of the rectangular region is 0.315+/−0.005 inches and the width of the rectangular region is 0.088+/−0.001 inches. Flat pattern 36 further comprises a U-shaped slot 38 cut at the proximal end of flat pattern 36 as shown in FIG. 2B. The width of slot 38 is 0404+/−0.002 inches. The length of the straight region of slot 38 is 0.174+/−0.005 inches. The distal end of slot 38 comprises a semi-circular region as shown in FIG. 2B. The proximal end of slot 38 comprises rounded edges with a radius of 0.2+/−0.005 inches. The distal region of flat pattern 36 may comprise one or more semicircular notches 40 that create inwardly opening flaps 20. In the embodiment shown in FIG. 2B, flat pattern 36 comprises three notches 40. In this embodiment, the width of notches 40 is 0.010+/−0.001 inches. The length of the straight region of notches 40 is 0.010+/−0.001 inches. The distal end of notches 40 comprises a semi-circular region as shown in FIG. 2B. A suitable connector 16 is passed through the lumen of the nickel-titanium alloy (e.g., nitinol) tube. Connector 16 is attached to the distal end of the nickel-titanium alloy (e.g., nitinol) tube. Inwardly opening flaps 20 are crimped onto the outer surface of connector 16. This crimping produces additional anchoring sites on the nickel-titanium alloy (e.g., nitinol) tube to anchor connector 16 to the nickel-titanium alloy (e.g., nitinol) tube. The nickel-titanium alloy (e.g., nitinol) tube then acts as distal anchor 12. A region of connector 16 emerges out of distal anchor through slot 38. The diameter of slot 38 may be designed to allow the edges of slot 38 to accurately contact the outer surface of connector 16.

Figure 2C:
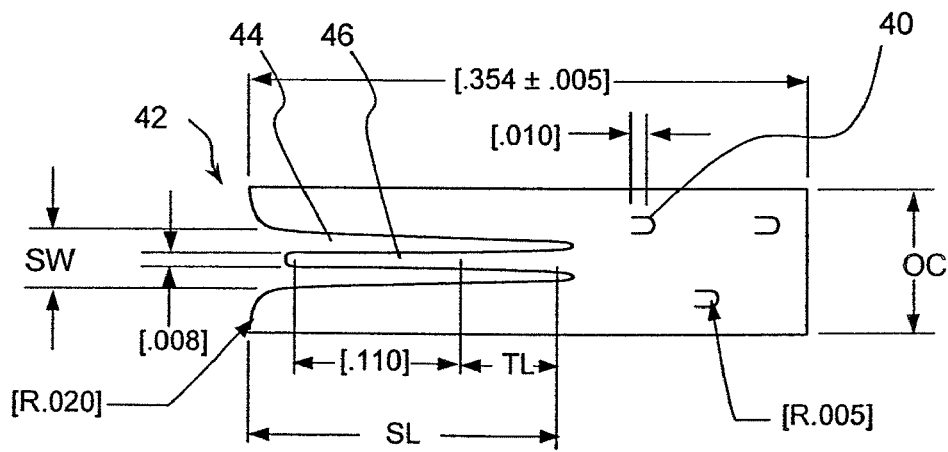
FIG. 2C shows a second embodiment of a flat pattern that can be used to design the distal anchor of FIG. 2A.
Figure 2:
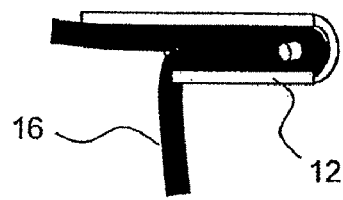
FIG. 2D shows a longitudinal sectional view through an embodiment of a distal anchor that is attached to a connector by a crimped loop.
FIG. 2E shows a longitudinal sectional view through an embodiment of a distal anchor that is attached to a connector by multiple crimped loops.
FIG. 2F shows a perspective view through an embodiment of a distal anchor that is attached to a connector by a buckle.
FIG. 2G shows a side view of the embodiment of a distal anchor of FIG. 2F that is attached to a connector under tension.
FIG. 2H shows a perspective view of an embodiment of a distal anchor that is attached to a connector by a knot.
FIG. 2I shows a longitudinal sectional view through an embodiment of a distal anchor that is attached to a connector by an adhesive.
FIG. 2J shows an alternate or complementary attachment mechanism.
Figure 2:
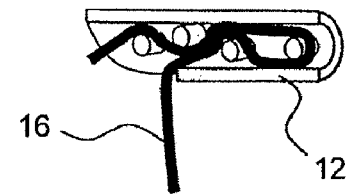
Figure 2:
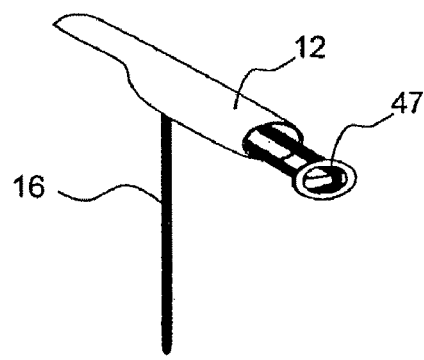
Figure 2:
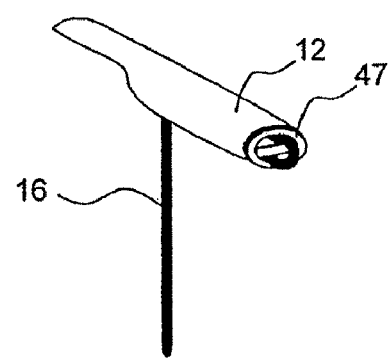
Figure 2:
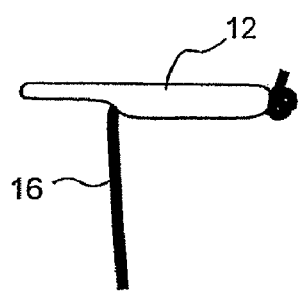
Figure 2:
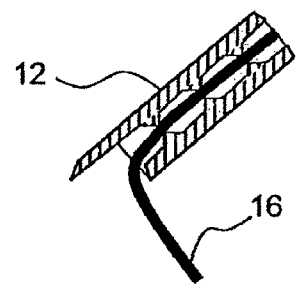
Figure 2:
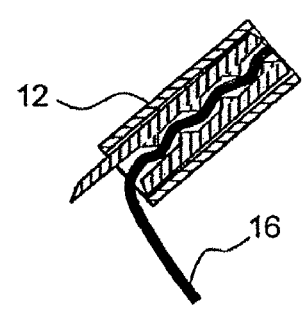

FIG. 2C shows a second embodiment of a flat pattern that can be used to design distal anchor 12 of FIG. 2A. In FIG. 2C, flat pattern 42 comprises a rectangular region. In one embodiment, the length of the rectangular region is 0.354+/−0.005 inches and the width of the rectangular region OC is 0.88+/−0.001 inches. Flat pattern 42 further comprises a W-shaped slot 44 cut at the proximal end of flat pattern 42 as shown in FIG. 2C. The distal end of slot 44 comprises two semi-circular regions as shown in FIG. 2C. In the embodiment shown in FIG. 2C, the radius of the semicircular regions is approximately 0.0015 inches. The length of slot 44 measured along the length of flat pattern 42 from the proximal end of flat pattern 42 to the proximal edges of the semicircular regions is 0.174+/−0.005 inches. Slot 44 encloses a central folding tab 46. In the embodiment shown in FIG. 2C, folding tab 46 comprises a straight proximal region and a tapering distal region. The length of the straight proximal region of folding tab 46 is 0.11+/−0.010 inches. The length of the tapering distal region of folding tab 46 is 0.040+/−0.005 inches. The proximal end of slot 44 has rounded edges with a radius of 0.020+/−0.005 inches. The distal region of flat pattern 42 may comprise one or more semicircular notches 40. In the embodiment shown in FIG. 2C, flat pattern 42 comprises three notches 40 that create inwardly opening flaps 20. In this embodiment, the width of notches 40 is 0.010+/−0.001X inches. The length of the straight region of notches 40 is 0.010+/−0.001 inches. The distal end of notches 40 comprises a semi-circular region as shown in FIG. 2C. A suitable connector 16 is passed through the lumen of the nickel-titanium alloy (e.g., nitinol) tube. Connector 16 is attached to the distal end of the nickel-titanium alloy (e.g., nitinol) tube. Inwardly opening flaps 20 are crimped onto the outer surface of connector 16. This crimping produces additional anchoring sites on the nickel-titanium alloy (e.g., nitinol) tube to anchor connector 16 to the nickel-titanium alloy (e.g., nitinol) tube. The nickel-titanium alloy (e.g., nitinol) tube then acts as distal anchor 12. A region of connector 16 emerges out of distal anchor through slot 44. To prevent or reduce the scraping of connector 16 by the distal edge of slot 44, a blunt edge is created at the distal edge of slot 44. This blunt edge is created by folding or bending folding tab 46 along the length of distal anchor 12. Several alternate designs of the blunt edge may be created using a variety of lengths of folding tab 46 and/or a variety of methods of folding or bending.

In the example shown in FIG. 2A, distal anchor 12 is attached to connector 16 by an attachment mechanism comprising an enlarged distal tip of connector 16. Several alternate or complementary attachment mechanisms are illustrated in FIGS. 2D-2J.

FIG. 2D shows a longitudinal sectional view through an embodiment of a distal anchor that is attached to a connector by a crimped loop. In FIG. 2D, the distal end of connector 16 is looped. This looped distal end of connector 16 is inserted into distal anchor 12. Distal anchor 12 is crimped to attach the looped distal end of connector 16 to distal anchor 12.

FIG. 2E shows a longitudinal sectional view through an embodiment of a distal anchor that is attached to a connector by multiple crimped loops. In FIG. 2E, the distal end of connector 16 is folded multiple times to obtain multiple loops. These multiple loops of connector 16 are inserted into distal anchor 12. Distal anchor 12 is crimped to attach the multiple loops of connector 16 to distal anchor 12.

FIG. 2F shows a perspective view through an embodiment of a distal anchor that is attached to a connector by a buckle. In FIG. 2F, the distal end of connector 16 is passed through distal anchor 12. The distal end of connector 16 is passed through a buckle 47 and is looped. The distal end of connector 16 is inserted back into distal anchor 12. The distal end of connector 16 may be attached to distal anchor 12 by one or more mechanisms disclosed herein. In the embodiment shown in FIG. 2F, the distal end of connector 16 is attached to distal anchor 12 by a suitable biocompatible adhesive. Distal anchor 12 may be crimped to attach connector 16 to distal anchor 12.

FIG. 2G shows a side view of the embodiment of a distal anchor of FIG. 2F that is attached to a connector under tension. Buckle 47 prevents the looped distal end of connector 16 from unraveling within distal anchor 12.

FIG. 2H shows a perspective view of an embodiment of a distal anchor that is attached to a connector by a knot. In FIG. 2H, the distal end of connector 16 is passed through distal anchor 12. The distal end of connector 16 is knotted. This knot attaches the distal end of connector 16 to distal anchor 12.

FIG. 2I shows a longitudinal sectional view through an embodiment of a distal anchor that is attached to a connector by an adhesive. In FIG. 2I, the distal end of connector 16 is passed through distal anchor 12. This distal end of connector 16 is attached to distal anchor 12 by a suitable biocompatible adhesive. Examples of biocompatible adhesives that can be used to attach connector 16 to proximal anchor 12 include, but are not limited to epoxies, cyanoacrylates and thermoplastics. The inner surface of distal anchor 12 may be roughened or may be provided with one or more projections or depressions to increase the strength of the attachment between connector 16 to proximal anchor 12.

The various distal anchors disclosed herein may be delivered by one or more distal anchor delivery devices. Such distal anchor delivery devices may be introduced in the body of a human or animal through a variety of access routes. For example, the prostate gland of a patient with BPH may be treated by a distal anchor delivery device introduced transurethrally.

Figure 3A:
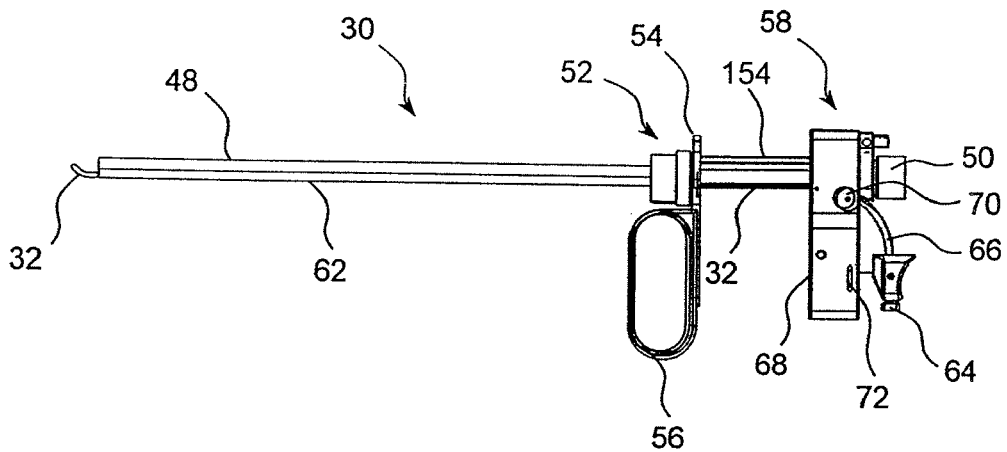
FIG. 3A shows a side view of a first embodiment of a distal anchor delivery device.

FIG. 3A shows a side view of a first embodiment of a distal anchor delivery device 30. Distal anchor delivery device 30 comprises an elongate endoscope introducing tube 48. The endoscope introducing tube 48 may range in length from 8 inches to 13 inches. In one embodiment, endoscope introducing tube 48 is made of stainless steel. The proximal end of endoscope introducing tube 48 may comprise an endoscope hub 50 to lock an endoscope to endoscope introducing tube 48. In the text the endoscope is used to mean any telescope, camera or optical system that provides visualization. In one embodiment, the endoscope is a 4 mm endoscope. A region of endoscope introducing tube 48 is attached to a distal handle assembly 52. In one embodiment, distal handle assembly 52 is made of anodized aluminum, stainless steel and nickel-plated brass components. The components may be fastened to each other by soldering, braising, welding or stainless steel fasteners. In the embodiment shown in FIG. 3A, distal handle assembly 52 comprises a distal attachment 54 that encloses endoscope introducing tube 48. Distal attachment 54 is further attached to a distal handle 56. A region of endoscope introducing tube 48 proximal to distal handle assembly 52 passes through a proximal handle assembly 58. In one embodiment, proximal handle assembly 58 is made of machined acetal resin engineering plastic (e.g., Delrin®, E.I. du Pont de Nemours and Company, Wilmington, Del.), polytetrafluoroethylene (PTFE), and nickel-plated brass components. The components may be fastened to each other by stainless steel fasteners. Proximal handle assembly 58 can slide over the outer surface of endoscope introducing tube 48. In the embodiment shown in FIG. 3A, distal anchor delivery device 30 further comprises one or more guide rails 60. The distal ends of guide rails 60 are attached to a proximal surface of distal attachment 54. Guide rails 60 pass through proximal handle assembly 58 such that proximal handle assembly 58 can slide over the outer surface of guide rails 60. Guide rails 60 help to stabilize the orientation of proximal handle assembly 58 relative to distal handle assembly 52 during the relative motion of proximal handle assembly 58 relative to distal handle assembly 52. Distal anchor delivery device 30 further comprises an elongate needle introducing tube 62. Needle introducing tube 62 is attached to endoscope introducing tube 48 as shown in FIG. 3A. In one embodiment, needle introducing tube 62 is made of stainless steel. Needle introducing tube 62 passes through distal handle assembly 52 and is attached to a region of distal handle assembly 52. The distal tip of needle introducing tube 62 may comprise a curved region. The curved distal tip of needle introducing tube 62 is used to direct the exit trajectory of an elongate needle 32 that slides through needle introducing tube 62. In one embodiment, needle 32 is made of nickel-titanium allow (e.g., nickel-titanium alloy (e.g., nitinol)) and comprises a ground beveled tip. The proximal end of needle 32 is attached to proximal handle assembly 58. Thus a user can move needle 32 through needle introducing tube 62 by moving proximal handle assembly 58 along endoscope introducing tube 48. Distal anchor delivery device 30 may comprise a needle stop to control the maximum movement of proximal handle assembly 58 along endoscope introducing tube 48. This in turn controls the maximum depth of penetration of needle 32 into a tissue. Needle 32 comprises a lumen through which a distal anchor deploying system is introduced in the anatomy. The distal anchor deploying system is used to deploy distal anchor 12 in the anatomy. The distal anchor deploying system comprises a pusher 64 that pushes distal anchor 12 out of needle 32 and into the anatomy. In one embodiment, pusher 64 is made of nickel-titanium alloy (e.g., nitinol). In the embodiment shown in FIG. 3A, the proximal end of pusher 64 is attached to a trigger 66 that is attached to a proximal handpiece 68 of the proximal handle assembly 58. Trigger 66 is attached to proximal handpiece 68 by a pivot 70. Thus, a user can move pusher 64 relative to needle 32 by moving trigger 66. Proximal handle assembly 58 further comprises a safety system 72 that prevents unwanted motion of trigger 66. In the embodiment shown in FIG. 3A, safety system 72 comprises a lock pin that locks trigger 66 to proximal handpiece 68. In one embodiment, the components of the safety system are made of stainless steel.

In one embodiment, distal anchor delivery device 30 is sized to be introduced through a 25F cystoscope sheath. The length of distal anchor delivery device 30 within the sheath ranges from 6 to 10 inches. In this embodiment, endoscope introducing tube 48 and endoscope hub 50 are designed to fit a 4 mm telescope. In this embodiment, the outer diameter of endoscope introducing tube 48 ranges from 0.174 to 0.200 inches and the inner diameter of endoscope introducing tube 48 ranges from 0.160 to 0.180 inches. In this embodiment, the outer diameter of needle introducing tube 62 ranges from 0.059 to 0.83 inches and the inner diameter of needle introducing tube 62 ranges from 0.041 to 0.072 inches. In this embodiment, the outer diameter of needle 32 ranges from 0.034 to 0.043 inches and the inner diameter of needle 32 ranges from 0.027 to 0.035 inches. In this embodiment, the outer diameter of pusher 64 ranges from 0.020 to 0.026 inches and the inner diameter of pusher 64 ranges from 0.014 to 0.019 inches. In this embodiment, the radius of the curved distal tip of needle introducing tube 62 ranges from 0.25 to 0.50 inches. In this embodiment, the maximum distance through which proximal handle assembly 58 can slide over the outer surface of endoscope introducing tube 48 ranges from 1 to 2 inches. In this embodiment, the maximum distance through which pusher 64 travels relative to needle 32 ranges from 0.2 to 0.8 inches. In a preferred embodiment, distal anchor delivery device 30 is sized to be introduced through a 25F cystoscope sheath. The length of distal anchor delivery device 30 within the sheath is 9.5 inches. In this preferred embodiment, endoscope introducing tube 48 and endoscope hub 50 are designed to fit a 4 mm telescope. In this preferred embodiment, the outer diameter of endoscope introducing tube 48 is 0.18 inches and the inner diameter of endoscope introducing tube 48 is 0.16 inches. In this preferred embodiment, the outer diameter of needle introducing tube 62 is 0.083 inches and the inner diameter of needle introducing tube 62 is 0.072 inches. In this preferred embodiment, the outer diameter of needle 32 is 0.037 inches and the inner diameter of needle 32 is 0.030 inches. In this preferred embodiment, the outer diameter of pusher 64 is 0.025 inches and the inner diameter of pusher 64 is 0.020 inches. In this preferred embodiment, the radius of the curved distal tip of needle introducing tube 62 is 0.3 inches. In this preferred embodiment, the maximum distance through which proximal handle assembly 58 can slide over the outer surface of endoscope introducing tube 48 is 1.7 inches. In this preferred embodiment, the maximum distance through which pusher 64 travels relative to needle 32 is 0.4 inches.

Figure 3B:
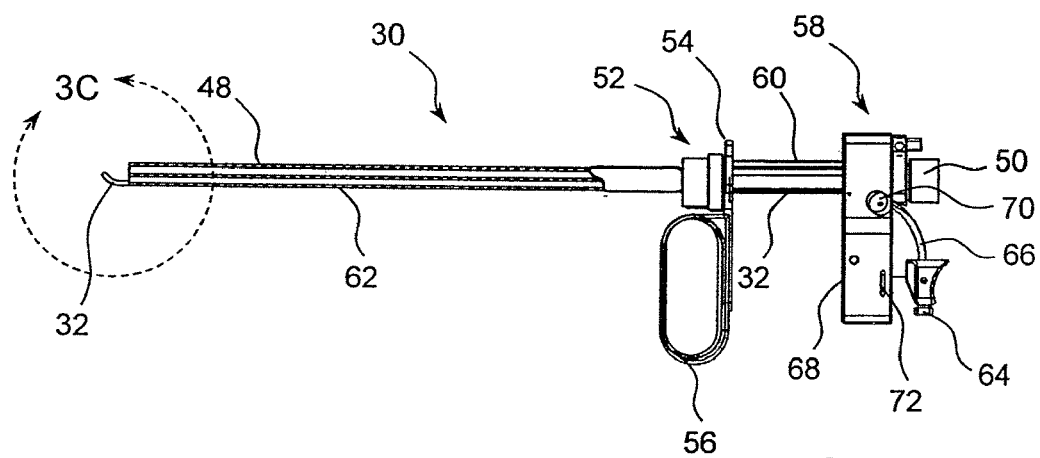
FIG. 3B shows the distal anchor delivery device of FIG. 3A with a portion of the distal region removed.

FIG. 3B shows the distal anchor delivery device of FIG. 3A with a portion of the distal region removed.

Figure 3C:
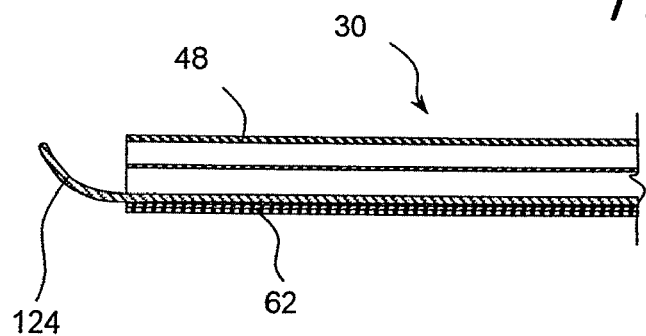
FIG. 3C shows an enlarged view of the distal region 3C of FIG. 3B.
Figure 3:
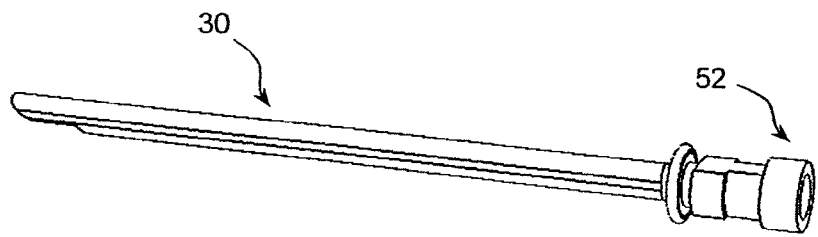
FIGS. 3D through 3K show various steps of a method of deploying a distal anchor in the anatomy by the distal anchor delivery device of FIG. 3A.
FIG. 3L shows a side view of a second embodiment of a distal anchor delivery device.
FIGS. 3M through 3T show steps of an embodiment of a method for deploying the anchor of FIG. 3L in an anatomical region.
FIG. 3U shows a first side view of the distal tip of an embodiment of a needle that can be used to introduce one or more of the distal anchors disclosed herein.
FIG. 3V shows a second side view of the distal tip of the embodiment of the needle shown in FIG. 3U.
FIG. 3W shows a longitudinal section through the distal tip of a distal anchor delivery device comprising a bushing to guide the trajectory of a needle through the distal anchor delivery device.
FIG. 3X shows a longitudinal section through the distal tip of a distal anchor delivery device comprising a distal crimp or dimple to guide the trajectory of a needle through the distal anchor delivery device.
FIG. 3Y shows a perspective view of the distal tip of a distal anchor delivery device comprising a bent, curved or angled needle introducing lumen.
FIG. 3Z shows a perspective view of an embodiment of a first elongate part that is used to construct the distal end of the embodiment of the distal anchor delivery device of FIG. 3Y.
Figure 3:
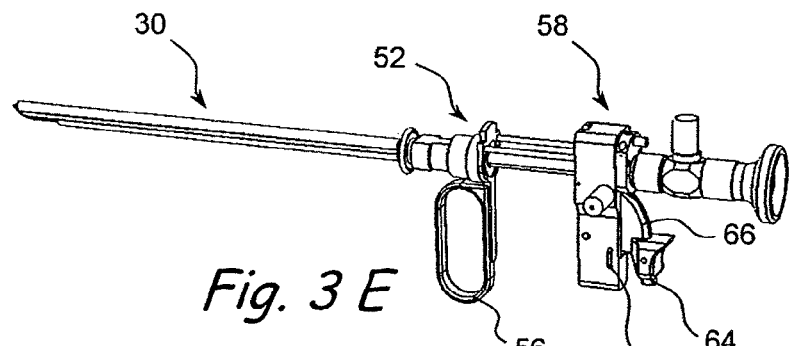
Figure 3:
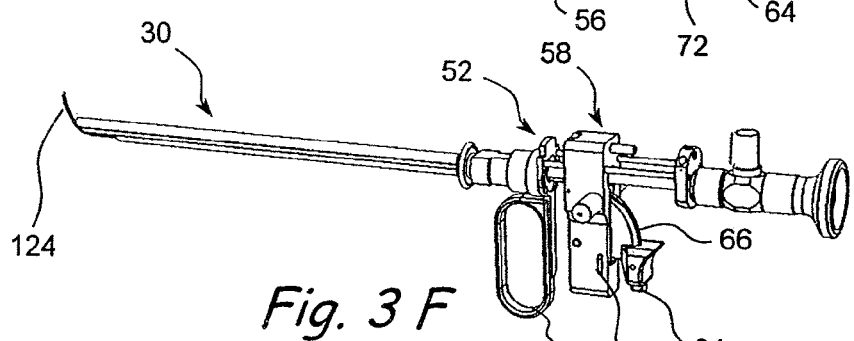
Figure 3:
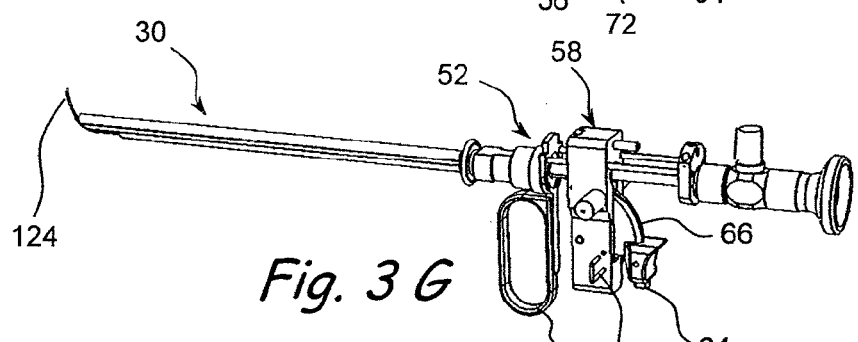
Figure 3:
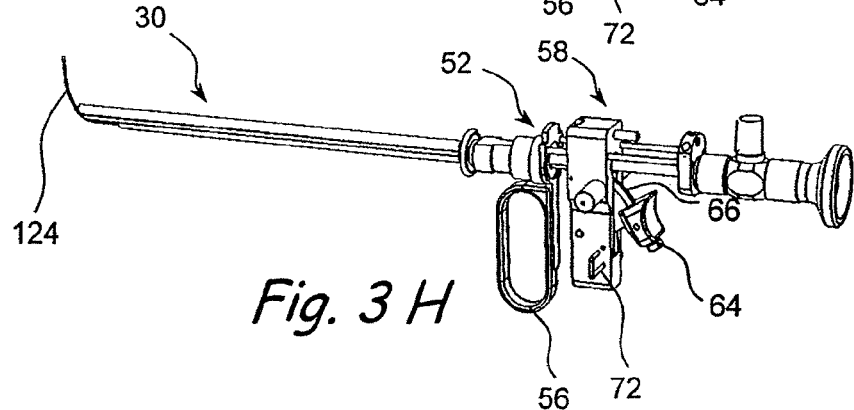
Figure 3:
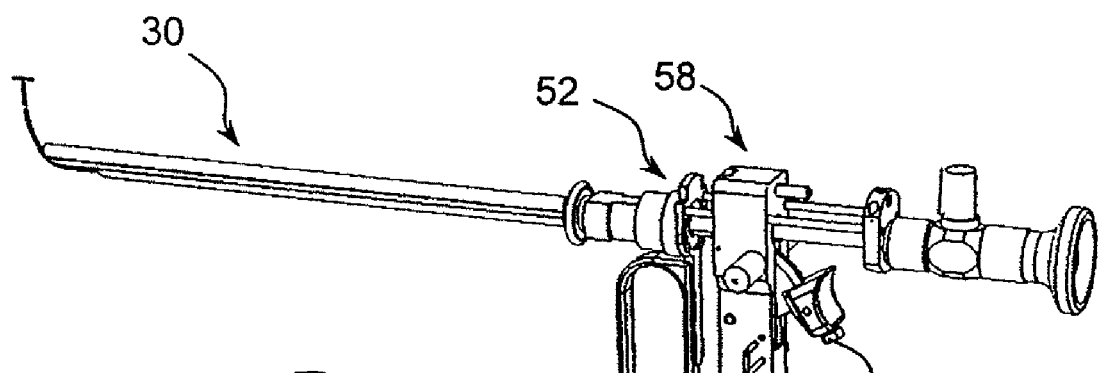
Figure 3:
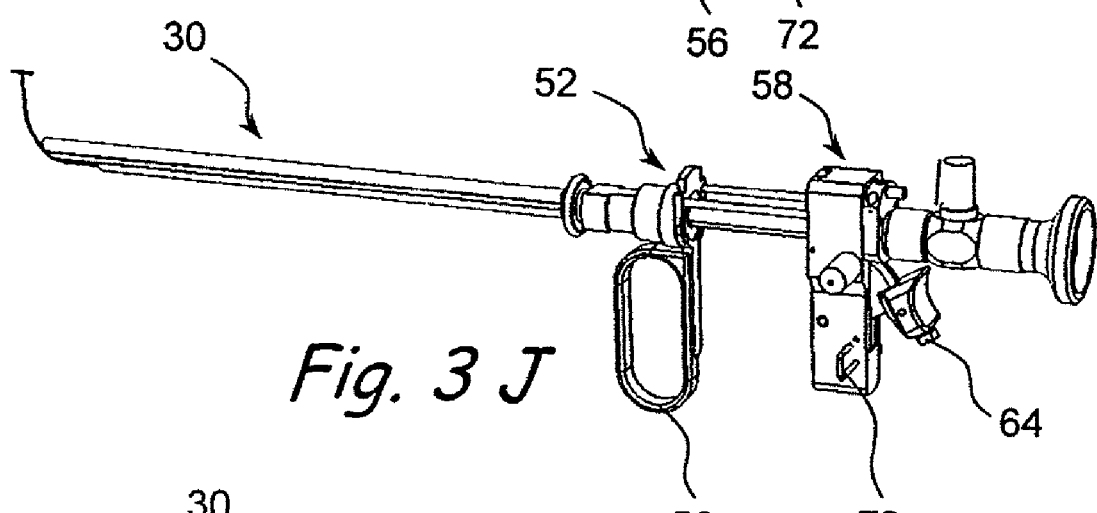
Figure 3:
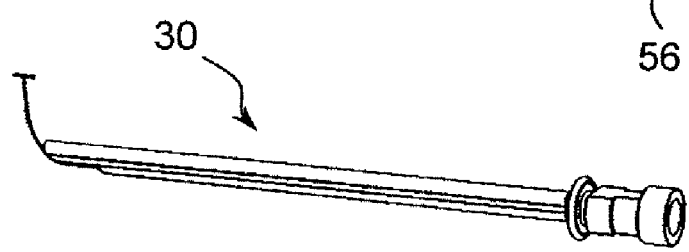
Figure 3:
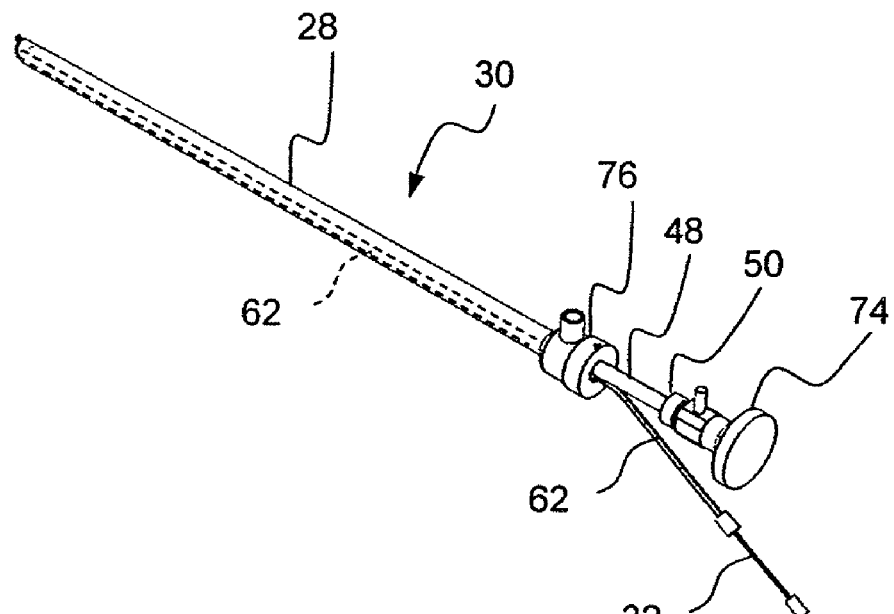
Figure 3:
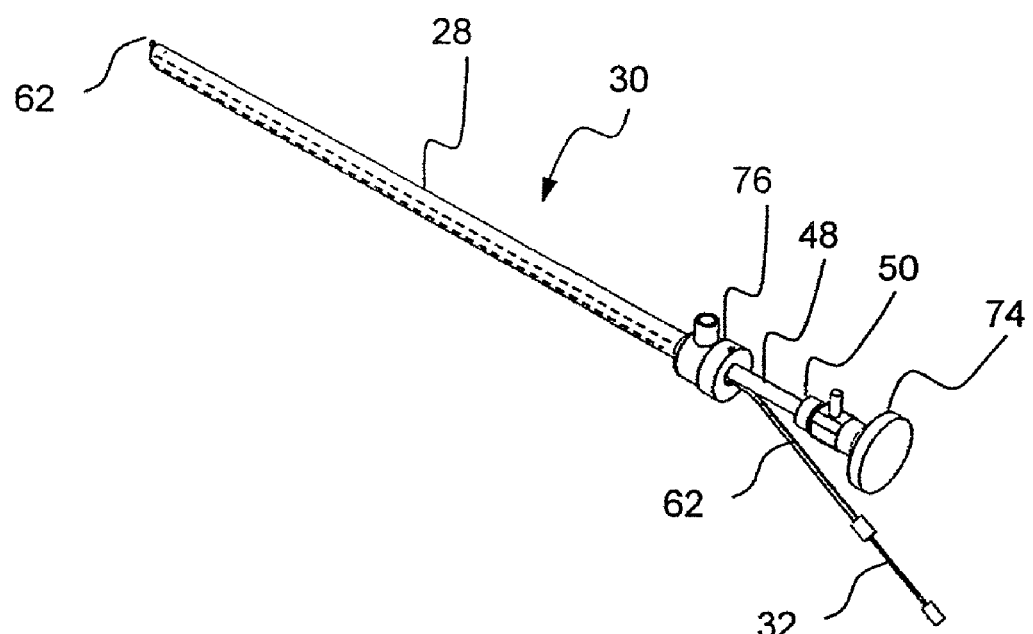
Figure 3:
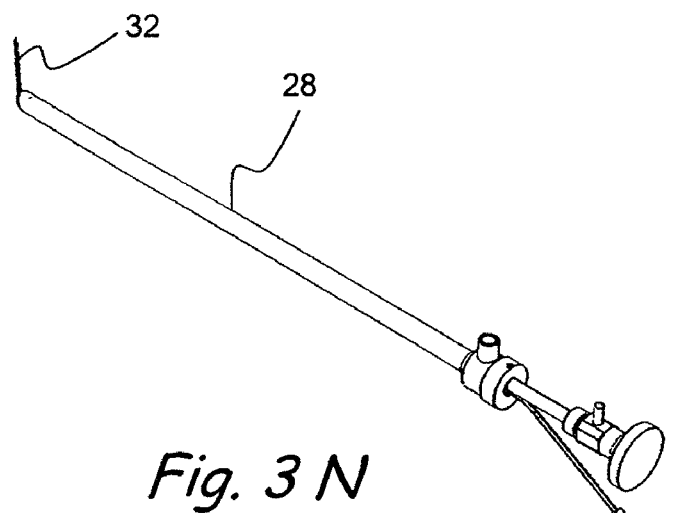
Figure 3:
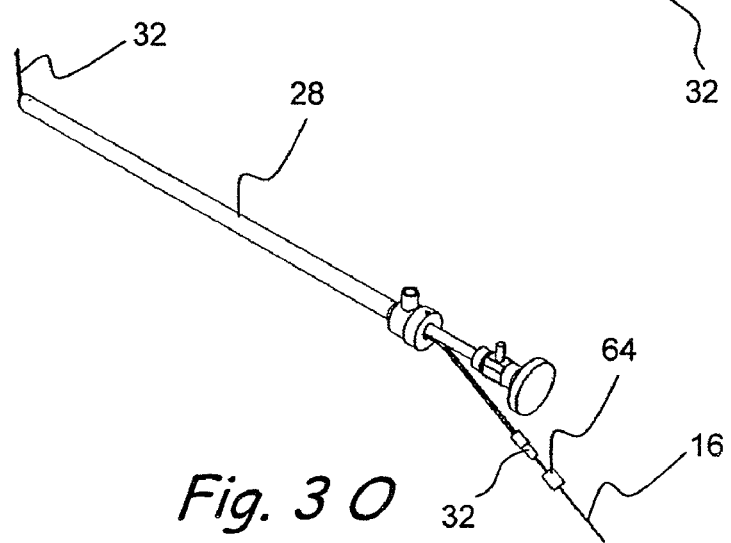
Figure 3:
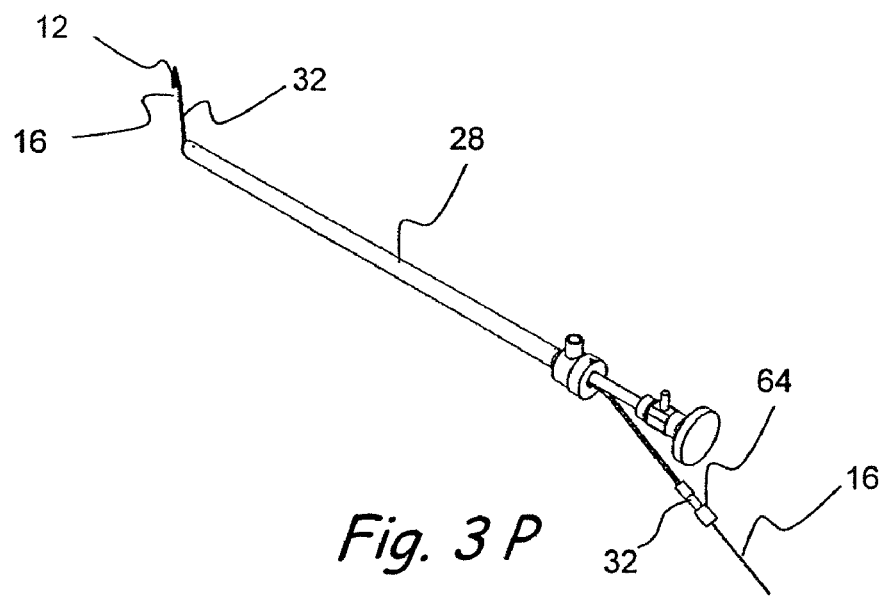
Figure 3:
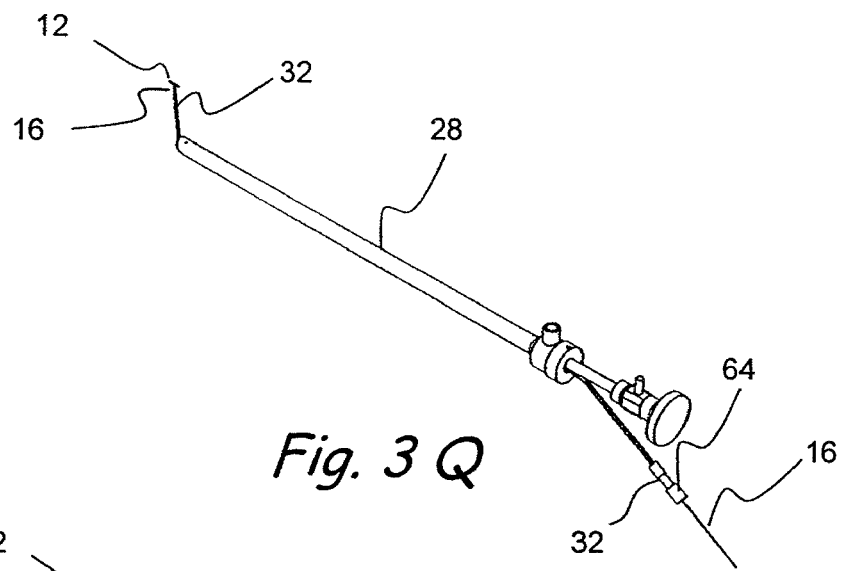
Figure 3:
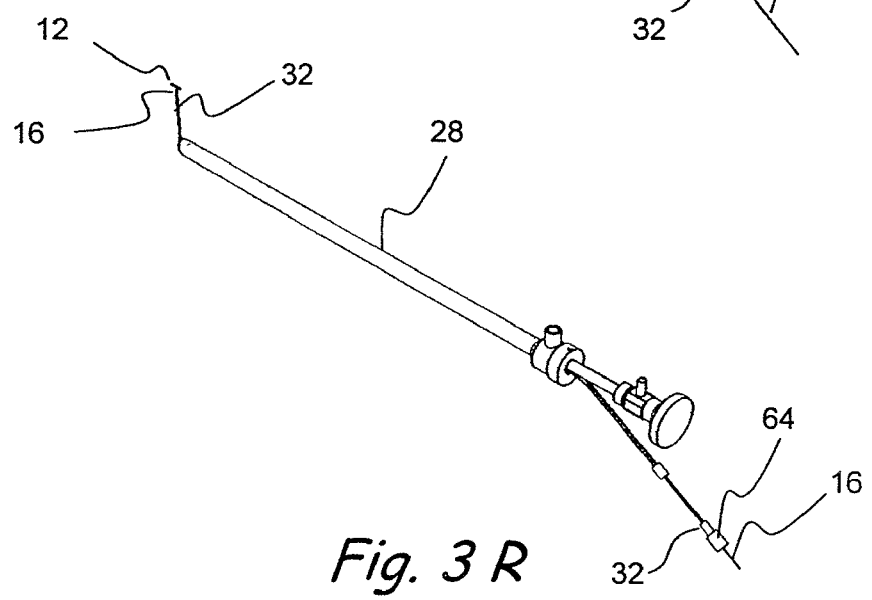
Figure 3:
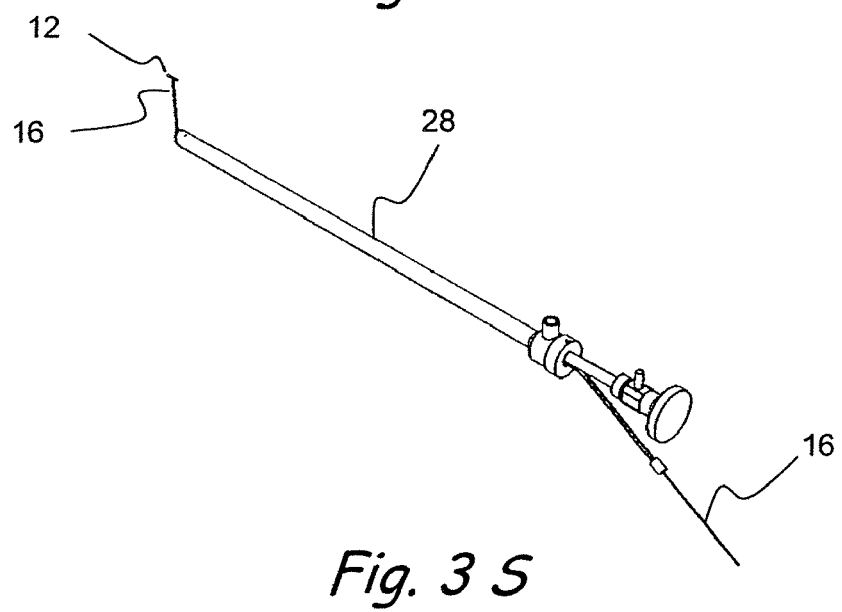
Figure 3:
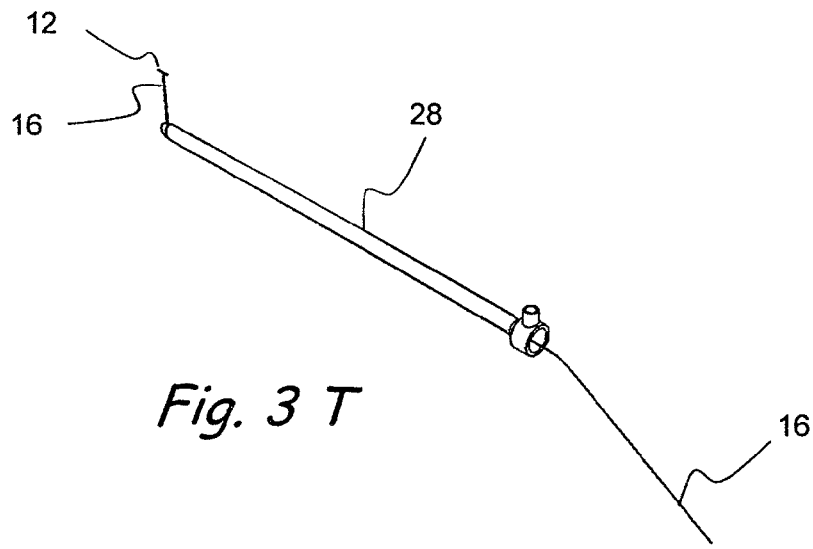
Figure 3:
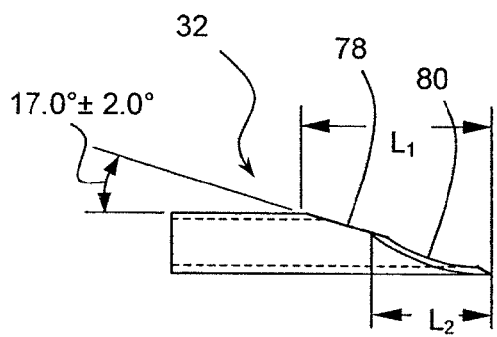
Figure 3:
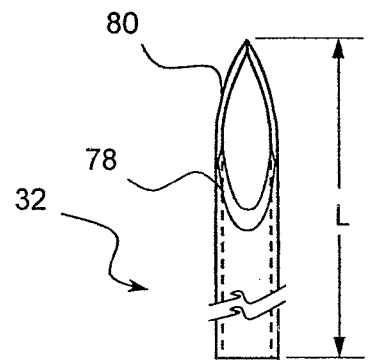
Figure 3:
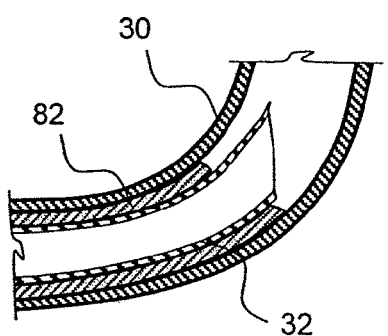
Figure 3:
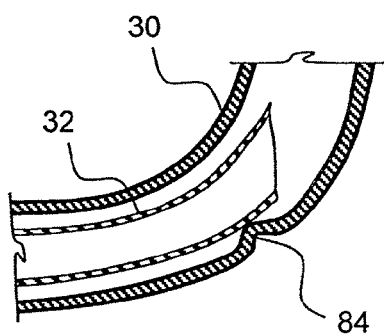

FIG. 3C shows an enlarged view of the distal region 3C of FIG. 3B. FIG. 3C shows the distal end of distal anchor delivery device 30 comprising elongate endoscope introducing tube 48 and needle introducing tube 62.

FIGS. 3D through 3K show various steps of a method of deploying distal anchor 12 in the anatomy by distal anchor delivery device 30 of FIG. 3A. For the description below regarding FIGS. 3D through 3K, the procedure is described as if applied to prostate gland although other anatomical regions could be used. In FIG. 3D, an elongate sheath 28 is introduced in the urethra. In one embodiment, sheath 28 is a 25F cystoscope resectoscope sheath. The position of sheath 28 is adjusted such that the distal tip of sheath 28 is close to the region of the urethra enclosed by the prostate gland. In FIG. 3E, distal anchor delivery device 30 is introduced through sheath 28 into the urethra. This step may performed under endoscopic visualization by an endoscope 74 inserted in the endoscope introducing tube 48 of distal anchor delivery device 30. Distal anchor delivery device 30 may be rotated to orient the distal tip of needle introducing tube 62 in a desired orientation with respect to an anatomical organ such as the prostate gland. In FIG. 3F, proximal handle assembly 58 is moved in the distal direction over endoscope introducing tube 48 relative to distal handle assembly 52. This in turn causes needle 32 to advance through needle introducing tube 62. The distal tip of needle 32 emerges out of the distal tip of needle introducing tube 62. Needle 32 penetrates through one or more anatomical regions. In one method embodiment, the distal tip of needle 32 emerges out of the capsule of the prostate gland and enters the surrounding pelvic space. In one method embodiment, the dimensions of the prostate gland are measured. This information is then used to determine the distance through which needle 32 is advanced through needle introducing tube 62. In FIG. 3G, safety system 72 is released. This step unlocks trigger 66 from proximal handpiece 68. In FIG. 3H, trigger 66 is lifted. This causes pusher 64 to advance in the distal direction through needle 32. This in turn causes distal anchor 12 to emerge out through the distal end of needle 32 and into the anatomy. In one method embodiment, distal anchor 12 emerges out of needle 32 and enters the surrounding pelvic space. In FIG. 3I, connector 16 is pulled in the proximal direction. This causes distal anchor 12 to orient itself perpendicularly to connector 16. In FIG. 3J, needle 32 is removed from the anatomy by pulling proximal handle assembly 58 in the proximal direction over endoscope introducing tube 48. In FIG. 3K, distal anchor delivery device 30 is removed from the anatomy.

FIG. 3L shows a side view of a second embodiment of a distal anchor delivery device 30. Distal anchor delivery device 30 comprises an endoscope introducing tube 48. The proximal end of endoscope introducing tube 48 may comprise an endoscope hub 50 to lock an endoscope 74 to endoscope introducing tube 48. Endoscope introducing tube 48 encloses a lumen through which endoscope 74 may be introduced into the anatomy. Distal anchor delivery device 30 comprises a needle introducing tube 62. Endoscope 74 is introduced through endoscope introducing tube 48 such that the distal end of needle introducing tube 62 is located near the distal end of endoscope 74. Needle introducing tube 62 is used to introduce a needle 32 into the anatomy. The distal end of needle introducing tube 62 may comprise a curved, bent or tapered region to introduce needle 32 into the anatomy at an angle to the axis of endoscope 74. Needle introducing tube 62 is attached to endoscope introducing tube 48 by a coupling element 76. Distal anchor delivery device 30 may be introduced into the anatomy through a suitable sheath. Such as sheath may comprise a flushing or aspiration port. The flushing or aspiration port may be in fluid communication with the lumen of the sheath to allow a user to introduce fluids into or remove fluids from an anatomical region.

FIGS. 3M through 3T show perspective views of distal anchor delivery device 30 of FIG. 3L showing the steps of an embodiment of a method of deploying an anchor in an anatomical region. Distal anchor delivery device 30 comprises endoscope introducing tube 48 that encloses a lumen. An endoscope 74 is located in the lumen of endoscope introducing tube 48. In the step shown in FIG. 3M, distal anchor delivery device 30 is introduced in an anatomical region such as the urethra through an elongate sheath 28. Distal anchor delivery device 30 may be rotated to orient the distal tip of needle introducing tube 62 in a desired orientation. A needle 32 is introduced through needle introducing tube 62. In the step shown in FIG. 3N, needle 32 is advanced through needle introducing tube 62 such that the distal end of needle 32 emerges out of the distal end of needle introducing tube 62 and enters an anatomical region. In one method embodiment, needle 32 is advanced such that the distal end of needle 32 penetrates through the prostate gland and enters the surrounding pelvic space. In this embodiment, the dimensions of the prostate gland may be measured. This information may then be used to determine the distance through which distal end of needle 32 penetrates through the prostate gland. In the step shown in FIG. 3O, distal anchor 12 attached to connector 16 is introduced into needle 32. Distal anchor 12 is pushed in the distal direction through needle 32 by pusher 64. In the step shown in FIG. 3P, distal anchor 12 is further pushed in the distal direction through needle 32 by pusher 64 such that distal anchor 12 emerges out of the distal end of needle 32. In the step shown in FIG. 3Q, connector 16 is pulled in the proximal direction. This causes distal anchor 12 to orient itself perpendicularly to connector 16. In the step shown in FIG. 3R, needle 32 and pusher 64 are pulled along the proximal direction. This step reintroduces the distal tip of needle 32 into needle introducing tube 62. In the step shown in FIG. 3S, pusher 64 and needle 32 are pulled further along the proximal direction such that pusher 64 and needle 32 are removed from distal anchor delivery device 30. In the step shown in FIG. 3T, distal anchor delivery device 30 is pulled along the proximal direction to remove distal anchor delivery device 30 from the anatomy.

FIG. 3U shows a first side view of the distal tip of an embodiment of a needle that can be used to introduce one or more of the distal anchors disclosed herein. FIG. 3U shows a needle 32 comprising a sharp distal tip. Needle 32 may be made of suitable biocompatible materials including, but not limited to nickel-titanium alloy (e.g., nitinol), stainless steel, etc. Needle 32 may comprise one or more curved, bent or angled regions. The outer diameter of needle 32 may range from 0.034 inches to 0.043 inches. Needle 32 encloses a lumen such that the inner diameter of needle 32 ranges from 0.027 niches to 0.035 inches. In a preferred embodiment, the outer diameter of needle 32 is approximately 0.0372 inches and the inner diameter is approximately 0.0295 inches. The length of needle 32 may range from 10 to 15 inches. In a preferred embodiment, length of needle 32 is 13+/−0.2 inches. In the embodiment shown in FIG. 3U, the distal tip of needle 32 has a first bevel 78 and a second bevel 80. In a preferred embodiment, the angle between first bevel 78 and the axis of needle 32 is 17 degrees. In this embodiment, the distance along the axis of needle 32 from the proximal end of first bevel 78 to the distal end of needle 32 is approximately 0.12 inches. Second bevel 80 is curved as shown in FIG. 3U. In the embodiment shown in FIG. 3U, the distance along the axis of needle 32 from the proximal end of second bevel 80 to the distal end of needle 32 is approximately 0.07 inches.

FIG. 3V shows a second side view of the distal tip of the embodiment of the needle shown in FIG. 3U. FIG. 3V shows a side view of needle 32 showing first bevel 78 and second bevel 80.

In an alternate embodiment, the outer diameter of needle 32 is 0.050+/−0.008 inches. Needle 32 encloses a lumen such that the inner diameter of needle 32 is 0.038+/−0.008 inches. The length of needle 32 is 12+/−4 inches. The angle between first bevel 78 and the axis of needle 32 may range from 20 to 24 degrees.

The distal tip of distal anchor delivery device 30 may comprise one or more guiding mechanisms to accurately guide the trajectory of needle 32 as needle 32 emerges from the distal tip of distal anchor delivery device 30. Such guiding mechanisms may also be used to prevent or reduce the scraping of the inner surface of distal anchor delivery device 30 by the sharp distal end of needle 32. For example, FIG. 3W shows a longitudinal section through the distal tip of distal anchor delivery device 30 comprising a bushing 82 to guide the trajectory of needle 32 through distal anchor delivery device 30. Bushing 82 may be made of suitable biocompatible materials including, but not limited to biocompatible metals such as stainless steel, nickel-titanium alloy (e.g., nickel-titanium alloy (e.g., nitinol)), and/or polymers; etc. In the example shown in FIG. 3W, bushing 82 is made of a curved cylindrical member. Bushing 82 lines the inner surface of distal anchor delivery device 30. In one embodiment, bushing 82 is attached to the inner surface of distal anchor delivery device 30 by a suitable adhesive. The distal end of bushing 82 is located proximal to the distal tip of distal anchor delivery device 30 as shown. This enables the distal sharp tip of needle 32 to emerge from the distal tip of distal anchor delivery device 30 without substantially scraping the inner surface of distal anchor delivery device 30.

FIG. 3X shows a longitudinal section through the distal tip of distal anchor delivery device 30 comprising a distal crimp 84 or dimple to guide the trajectory of needle 32 through distal anchor delivery device 30. Distal crimp 84 may be by crimping or dimpling the distal region of distal anchor delivery device 30 such that a region of distal crimp 84 extends into the lumen of distal anchor delivery device 30. Distal crimp 84 is located proximal to the distal tip of distal anchor delivery device 30 as shown. Distal crimp 84 acts as a ramp for needle 32. Thus needle 32 emerges from the distal tip of distal anchor delivery device 30 without substantially scraping the inner surface of distal anchor delivery device 30. Distal anchor delivery device 30 may comprise one or more distal crimps 84 or dimples.

Figure 3Y:
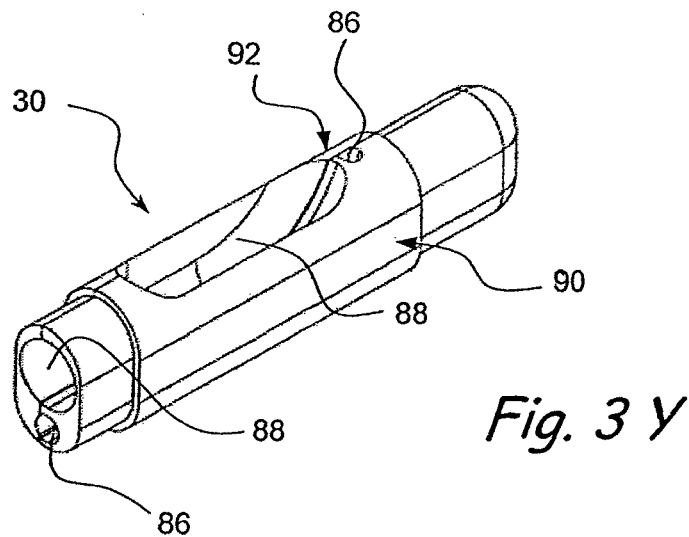
Figure 3A:
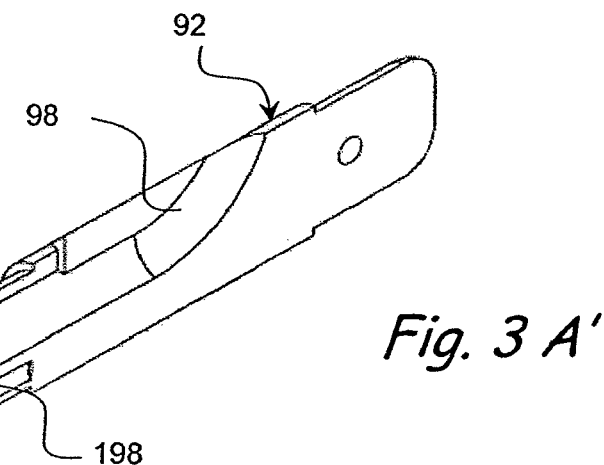

The distal tip of distal anchor delivery device 30 may comprise a bent, curved or angled tip. Such a bent, curved, or angled tip may be designed to introduce one or more devices such as needle 32 into the anatomy at an angle to the axis of distal anchor delivery device 30. In an alternate embodiment, the distal tip of distal anchor delivery device 30 comprises one or more bent, curved or angled lumens. For example, FIG. 3Y shows a perspective view of the distal tip of distal anchor delivery device 30 comprising a bent, curved or angled needle introducing lumen 86. Needle introducing lumen 86 may be used to introduce a needle 32 or other devices into the anatomy. In the embodiment shown in FIG. 3Y, needle introducing lumen 86 comprises a straight proximal region and a bent, curved or angled distal region. The distal most region of needle introducing lumen 86 may be oriented to the longitudinal axis of distal anchor delivery device 30 at an angle ranging from 30 degrees to 70 degrees. In the embodiment shown in FIG. 3Y, distal anchor delivery device 30 further comprises a bent, curved or angled endoscope introducing lumen 88. Endoscope introducing lumen 88 may be used to introduce an endoscope 74 or other devices into the anatomy. In the embodiment shown in FIG. 3Y, endoscope introducing lumen 88 comprises a straight proximal region and a bent, curved or angled distal region. The distal most region of endoscope introducing lumen 88 may be oriented to the longitudinal axis of distal anchor delivery device 30 at an angle. Thus, both needle 32 and endoscope 74 may be introduced into the anatomy at desired angles through distal anchor delivery device 30.

Figure 3Z:
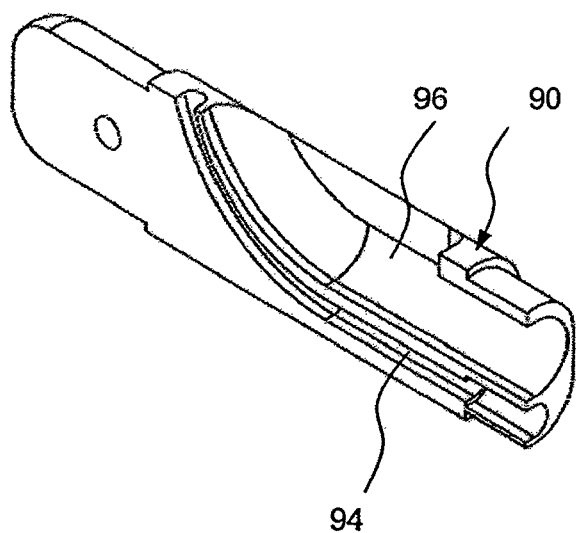

In one embodiment, needle introducing lumen 86 may be made by drilling a lumen through the distal region of distal anchor delivery device 30. In another embodiment, needle introducing lumen 86 is made of two grooved elongate parts that are attached to each other such that the two grooved elongate parts enclose needle introducing lumen 86. For example, the embodiment of the distal tip of distal anchor delivery device 30 shown in FIG. 3Y is made of two elongate parts: a first elongate part 90 and a second elongate part 92. FIG. 3Y' shows a perspective view of an embodiment of a first elongate part 90 that is used to construct the distal end of an embodiment of distal anchor delivery device 30. First elongate part 90 comprises a first groove 94. First groove 94 has a D-shaped cross section. The diameter of the semi-circular region of first groove 94 is approximately 0.045+/−0.005 inches. First elongate part 90 further comprises a second groove 96. Second groove 96 also has a D-shaped cross section. The diameter of the semi-circular region of second groove 96 is approximately 0.172+/−0.010 inches. FIG. 3Z shows a perspective view of an embodiment of a second elongate part 92 that is used to construct the distal end of an embodiment of distal anchor delivery device 30. Second elongate part 92 comprises a third groove 98. Third groove 98 has a D-shaped cross section. First elongate part 90 and second elongate part 92 are attached to each other such that second groove 96 and third groove 98 form endoscope introducing lumen 88. Also, when first elongate part 90 and second elongate part 92 are attached to each other, first groove 94 and an outer surface of second elongate part 92 form a D-shaped needle introducing lumen 86.

Figure 4:
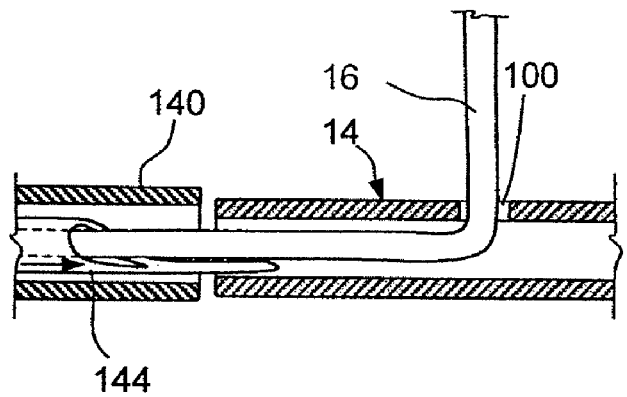
Figure 4:
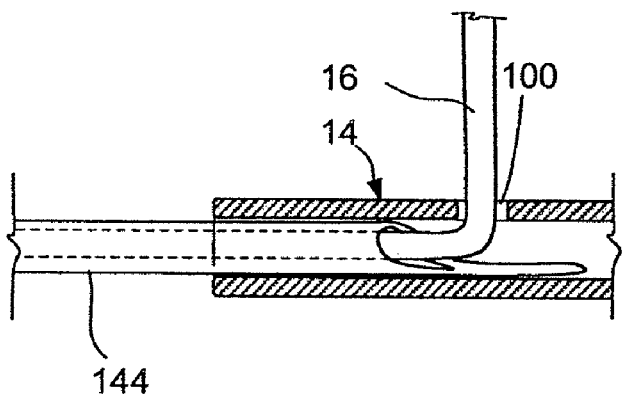
Figure 4:
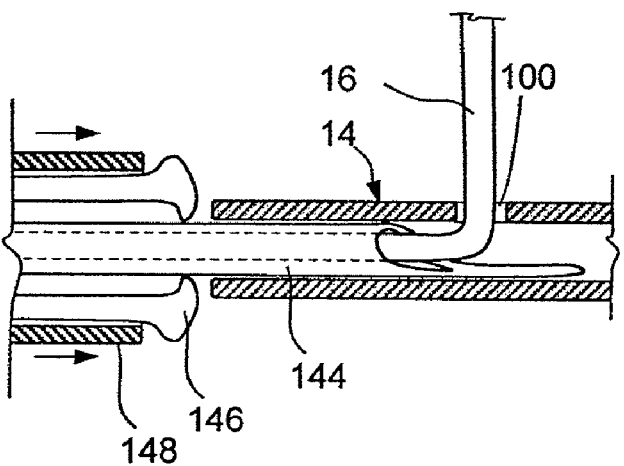
Figure 4:
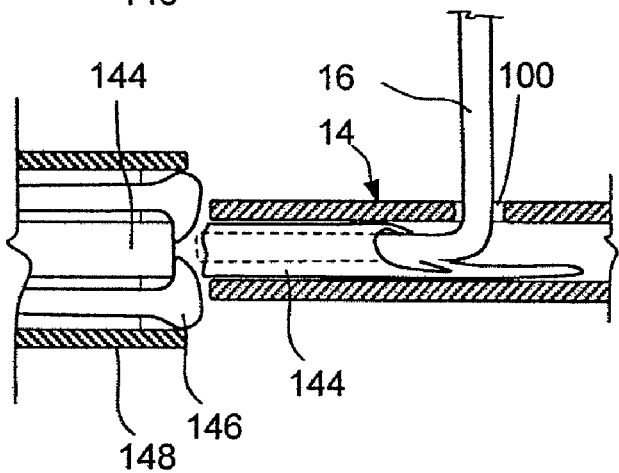
Figure 4:
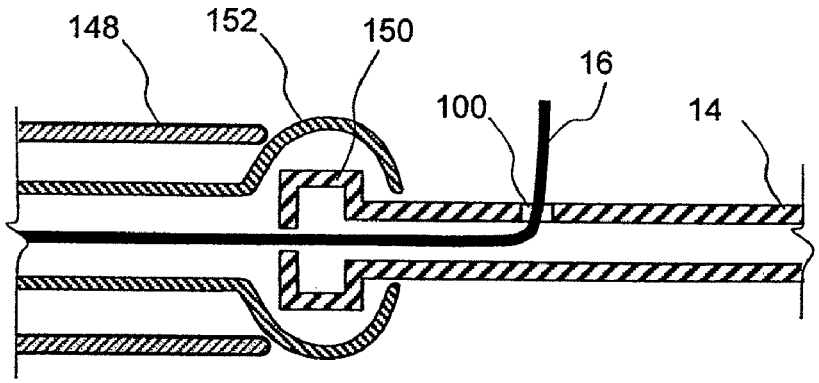
Figure 4:
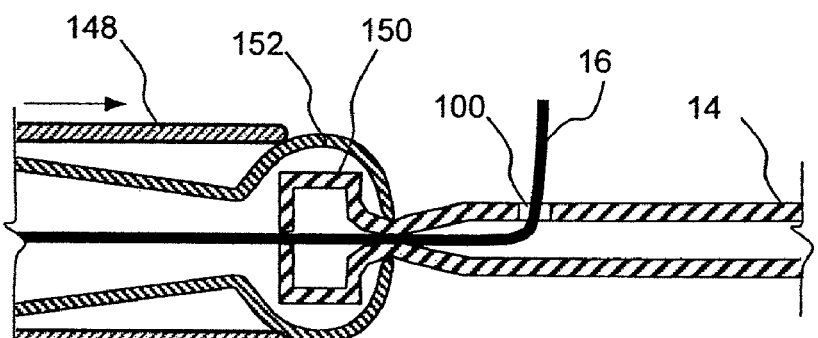
Figure 4:
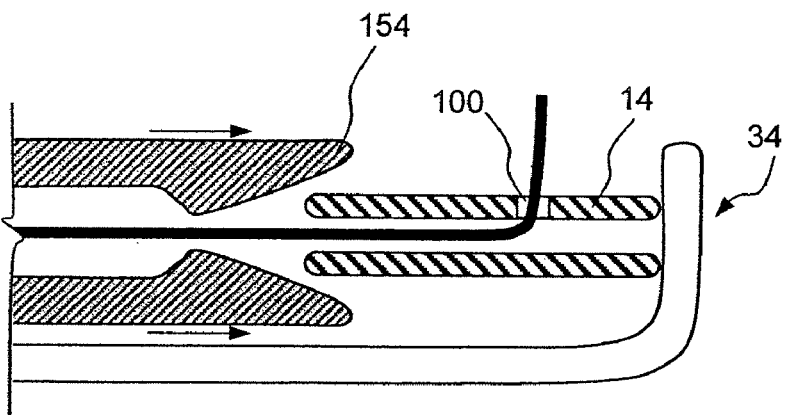
Figure 4:
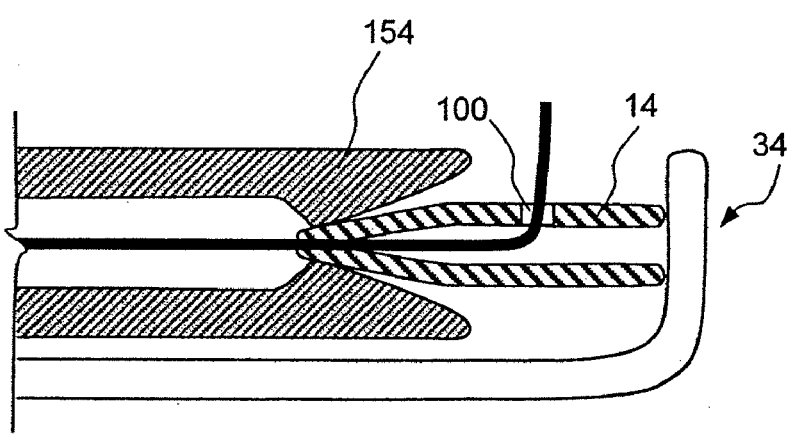
Figure 4:
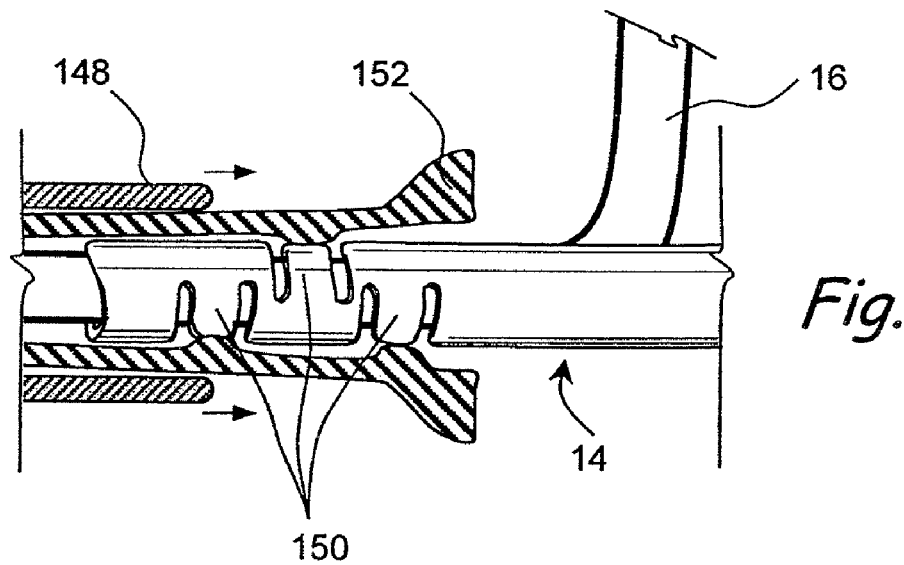
Figure 4:
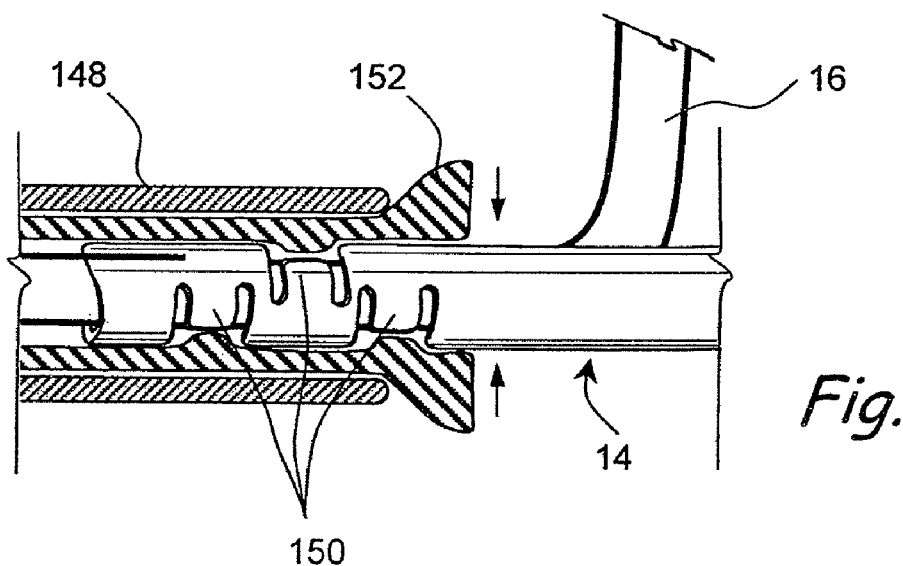
Figure 4:
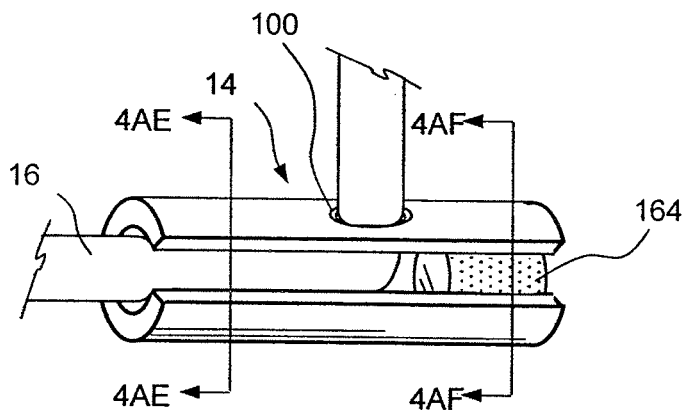
Figure 4:
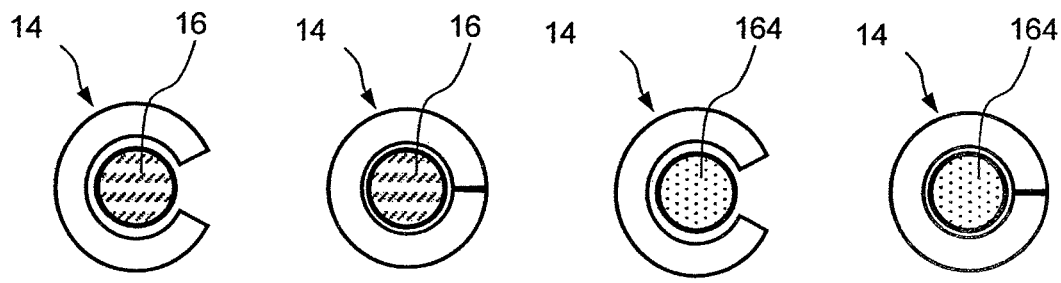
Figure 4:
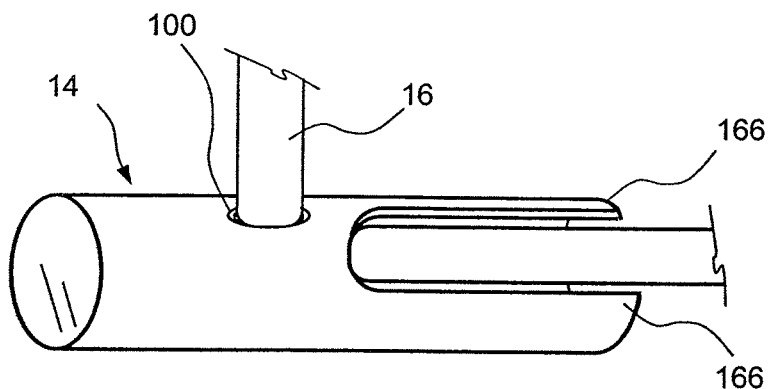
Figure 4:
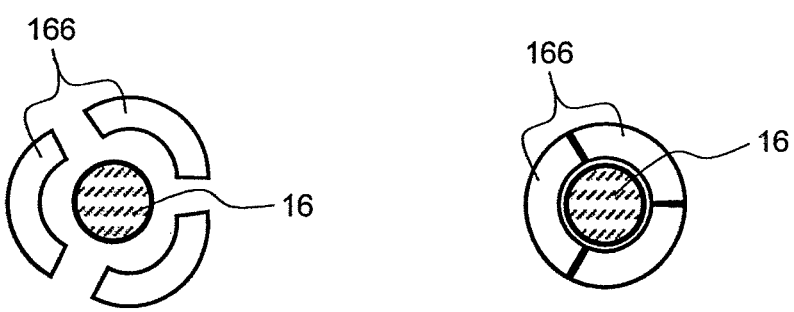
Figure 4:
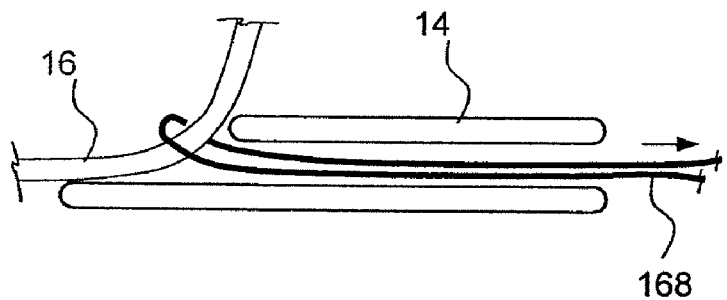
Figure 4:
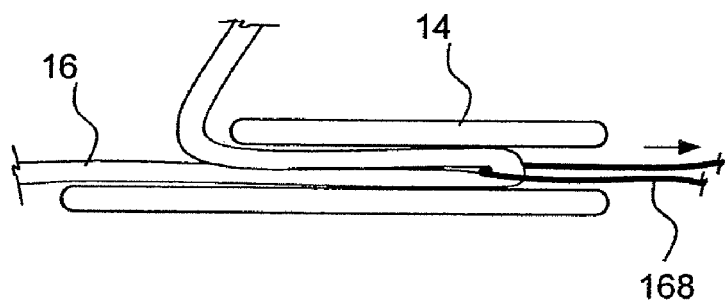
Figure 4:
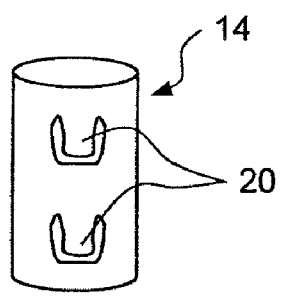
Figure 4:
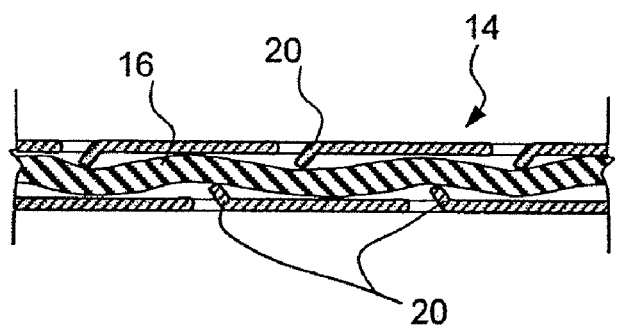

FIGS. 4A and 4B show longitudinal sections through a first embodiment of a proximal anchor showing the steps of an embodiment of a method of attaching the proximal anchor to a connector. In the embodiment shown in FIG. 4A, proximal anchor 14 comprises a hollow tube. The hollow tube comprises a connector opening 100 located roughly midway between the ends of the tube. In the embodiment shown in FIG. 4A, connector opening 100 is made by cutting outwardly opening flap 26 in the material of the tube. Outwardly opening flap 26 is folded as shown in FIG. 4A to create a blunt edge to connector opening 100. Proximal anchor 14 further comprises a locking tab 102. Locking tab 102 is made by cutting a flap in the material of proximal anchor 14 and bending the flap into the lumen of proximal anchor 14 as shown. Connector 16 enters proximal anchor 14 through connector opening 100. Connector 16 emerges out of proximal anchor 14 through the distal end of proximal anchor 14. Connector 16 can be attached to proximal anchor 14 by a lock pin 104. Lock pin 104 comprises an elongate body with a tapering distal tip. Lock pin 104 comprises a locking slot 106. Locking slot 106 is designed such that locking tab 102 fits into locking slot 106. This temporarily locks lock pin 104 to proximal anchor 14 as shown in FIG. 4A. In FIG. 4B, lock pin 104 is pushed in the distal direction by a user. This releases locking tab 102 from locking slot 106. This in turn releases lock pin 104 from proximal anchor 14. Lock pin 104 then moves in the distal direction. The tapering distal tip of lock pin 104 then wedges firmly between connector 16 and proximal anchor 14. This attaches connector 16 to proximal anchor 14. Lock pin 104 and proximal anchor 14 may comprise further mechanisms to prevent relative motion between lock pin and proximal anchor 14 after connector 16 is attached to proximal anchor 14.

One or more edges of connector opening 100 may be smoothened. In one method embodiment, the edges are smoothened by applying a coating. In another method embodiment, the edges are smoothened by polishing. In another embodiment, the edges are smoothened by folding the material around connector opening 100.

In one embodiment of a method of manufacturing proximal anchor 104, a tube is laser cut with a radially aligned laser. The geometry of the laser cut pattern is specified using a flat pattern drawing which is mapped onto the outside circumference of the tube. FIG. 4C shows a first embodiment of a flat pattern that can be used to manufacture proximal anchor 14 of FIG. 4A. The length of the rectangular region represents the length of the tube. The width of the rectangular region OC represents the outer circumference of the tube. In FIG. 4C, third flat pattern 108 comprises a rectangular region. In one embodiment, the length of the rectangular region is 0.236+/−0.005 inches and the width of the rectangular region OC is 0.088+/−0.002 inches. Third flat pattern 108 further comprises a U-shaped slot 110 cut at the proximal end of third flat pattern 108 as shown in FIG. 4C. The largest width of slot 110 is 0.028+/−0.001 inches. The total length of slot 110 is 0.050+/−0.002 inches. The proximal end of slot 110 encloses a rectangular region as shown in FIG. 4C. The rectangular region is folded to create outwardly opening flap 26. The distal end of slot 110 comprises rounded edges with a radius of approximately 0.014 inches. The distal region of third flat pattern 108 comprises a second U-shaped slot 112 as shown in FIG. 4C. In one embodiment of a method of manufacturing proximal anchor 14, a nickel-titanium alloy (e.g., nickel-titanium alloy (e.g., nitinol)) or stainless steel tube is cut according to third flat pattern 108. The rectangular region of slot 110 is bent outwards to create outwardly opening flap 26. The region enclosed by second U-shaped slot 112 is bent inwards to create locking tab 102.

FIGS. 4D and 4E show longitudinal sections through a second embodiment of a proximal anchor showing the steps of an embodiment of a method of attaching the proximal anchor to a connector. In the embodiment shown in FIG. 4D, proximal anchor 14 comprises a hollow tube. The hollow tube comprises a connector opening 100 located roughly midway between the ends of the tube. In the embodiment shown in FIG. 4D, connector opening 100 is made by cutting outwardly opening flap 26 in the material of the tube. Outwardly opening flap 26 is folded as shown in FIG. 4D to create a blunt edge to connector opening 100. Connector 16 enters proximal anchor 14 through connector opening 100. Connector 16 emerges out of proximal anchor 14 through a first shearing opening 114 of proximal anchor 14. Connector 16 can be attached to proximal anchor 14 by a lock pin 104. Lock pin 104 comprises an elongate body with a tapering proximal tip. Proximal anchor 14 further comprises a securing mechanism to prevent lock pin 104 from separating from proximal anchor 14. In the embodiment shown in FIG. 4D, the securing mechanism comprises a locking crimp 103. Locking crimp 103 is made by crimping a region of the wall of proximal anchor 14. Locking crimp 103 prevents lock pin 104 from accidentally emerging from the distal end of proximal anchor 14. In the embodiment shown in FIG. 4D, proximal anchor 14 further comprises a second securing mechanism. The second securing mechanism comprises a locking tab 102. Locking tab 102 fits into a locking slot 106 present on lock pin 104. This temporarily locks lock pin 104 to proximal anchor 14 as shown in FIG. 4D. Lock pin 104 further comprises a distal locking notch 118 that is located distal to locking slot 106. Connector 16 is attached to proximal anchor 14 by pulling an actuator 120 located on a proximal anchor delivery device 34. Actuator 120 comprises a distal bent region as shown in FIG. 4D. The distal bent region of actuator 120 pulls the distal end of lock pin 104 in the proximal direction. Actuator 120 further comprises a second shearing opening 122, such that connector 16 passes through second shearing opening 122. Proximal anchor is prevented from moving in the proximal direction by a holder 124 located on a proximal anchor delivery device 34.

In FIG. 4E, a user pulls actuator 120 in the proximal direction. Actuator 120 in turn pulls lock pin 104 in the proximal direction. This releases locking tab 102 from locking slot 106. This in turn releases lock pin 104 from proximal anchor 14. Lock pin 104 then moves in the proximal direction. The tapering proximal tip of lock pin 104 then wedges firmly between connector 16 and proximal anchor 14. This attaches connector 16 to proximal anchor 14. Also, locking tab 102 locks into distal locking notch 118 thereby further securing lock pin 104 to proximal anchor 14. The movement of lock pin 104 in the proximal direction also shears connector 16 between first shearing opening 114 and second shearing opening 122. This cuts connector 16 thereby releasing proximal anchor 14 from proximal anchor delivery device 34.

Connector 16 may enter or exit proximal anchor 14 through one or more connector openings. The walls of such openings may comprise one or more bent tabs. Such bent tabs may be bent inwards into the proximal anchor and may be used to wedge lock pin 104 to connector 16. For example, FIGS. 4F and 4G show longitudinal sections through a third embodiment of a proximal anchor showing the steps of an embodiment of a method of attaching the proximal anchor to a connector. In the embodiment shown in FIG. 4F, proximal anchor 14 comprises a hollow tube. The hollow tube comprises a connector opening 100 located roughly midway between the ends of the tube. In the embodiment shown in FIG. 4F, connector opening 100 is made by cutting an H-shaped slot in the material of the tube. The H-shaped slot creates an outwardly opening flap 26. Outwardly opening flap 26 is folded as shown in FIG. 4F to create a blunt edge to connector opening 100. The H-shaped slot also creates an inwardly opening wedging tab 126 as shown in FIG. 4F. Proximal anchor 14 further comprises a locking tab 102. Locking tab 102 is made by cutting a flap in the material of proximal anchor 14 and bending the flap into the lumen of proximal anchor 14 as shown. Connector 16 enters proximal anchor 14 through connector opening 100. Connector 16 emerges out of proximal anchor 14 through an end of proximal anchor 14. Connector 16 can be attached to proximal anchor 14 by a lock pin 104. Lock pin 104 comprises an elongate body with a tapering tip. Lock pin 104 comprises a locking slot 106. Locking slot 106 is designed such that locking tab 102 fits into locking slot 106. This temporarily locks lock pin 104 to proximal anchor 14 as shown in FIG. 4F.

In FIG. 4G, lock pin 104 is moved by a user. This releases locking tab 102 from locking slot 106. This in turn releases lock pin 104 from proximal anchor 14. Lock pin 104 then moves within proximal anchor 14 such that the tapering tip of lock pin 104 wedges firmly between connector 16 and proximal anchor 14. Further, wedging tab 126 gets wedged between lock pin 104 and connector 16. This attaches connector 16 to proximal anchor 14. Lock pin 104 and proximal anchor 14 may comprise mechanisms to prevent relative motion between lock pin 104 and proximal anchor 14 after connector 16 is attached to proximal anchor 14.

In one embodiment of a method of manufacturing proximal anchors of FIGS. 4F and 4G, a tube is laser cut with a radially aligned laser. The geometry of the laser cut pattern is specified using a flat pattern drawing which is mapped onto the outside circumference of the tube. FIG. 4H shows an embodiment of a flat pattern that can be used to design proximal anchor 14 of FIGS. 4F and 4G. In FIG. 4H, fourth flat pattern 128 comprises a rectangular region. In one embodiment, the length of the rectangular region is 0.236+/−0.005 inches and the width of the rectangular region OC is 0.088+/−0.002 inches. The proximal region of fourth flat pattern 128 comprises a U-shaped slot 112 as shown in FIG. 4H. Fourth flat pattern 128 further comprises an H-shaped slot 130 as shown in FIG. 4H. The largest width of slot 110 is 0.028+/−0.001 inches. The total length of slot 110 is 0.050+/−0.002 inches. In one embodiment of a method of manufacturing proximal anchor 14 of FIGS. 4F and 4G, a nickel-titanium alloy (e.g., nickel-titanium alloy (e.g., nitinol)) or stainless steel tube is cut according to fourth flat pattern 128. The proximal rectangular region created by H-shaped slot 130 is bent outwards to create outwardly opening flap 26. The distal rectangular region created by H-shaped slot 130 is bent inwards to create wedging tab 126. The region created by U-shaped slot 112 is bent inwards to create locking tab 102.

FIGS. 4I and 4J show longitudinal sections through a fourth embodiment of a proximal anchor showing the steps of an embodiment of a method of attaching the proximal anchor to a connector. Proximal anchor 14 comprises a hollow tube. The tube comprises a proximal opening and a distal opening. Proximal anchor 14 further comprises multiple connector openings 198. Connector 16 is introduced through one connector opening 100 and is weaved through the multiple connector openings 198 as shown in FIGS. 4I and 4J. The edges of connector openings 198 may be coated or polished to facilitate smooth movement of proximal anchor 14 over connector 16. Proximal anchor 14 further comprises lock pin 104 located in the lumen of proximal anchor 14. Proximal anchor 14 may comprise one or more restricting elements to restrict the movement of lock pin 104 within proximal anchor 14. In the embodiment shown in FIGS. 4I and 4J, proximal anchor 14 comprises two crimps 132 that act as restricting elements. Crimps 132 prevent lock pin 104 from escaping from the lumen of proximal anchor 14. In the step shown in FIG. 4I, proximal anchor 14 is advanced over connector 16 to position proximal anchor 14 in a desired location. In the step shown in FIG. 4J, lock pin 104 is advanced through proximal anchor 14. Lock pin 104 wedges between connector 16 and proximal anchor 14. This locks connector 16 to proximal anchor 14. The excess length of connector 16 may be cut or trimmed.

Several embodiments of lock pin 104 may be used to lock connector 16 to proximal anchor 14. Such lock pins 104 may comprise one or more tapered regions that wedge between connector 16 and a region of proximal anchor 14. In addition, several alternate embodiments of wedging elements may be used to attach connector 16 to a region of proximal anchor 14. For example, FIGS. 4K and 4L show longitudinal sections through a proximal anchor showing the steps of an embodiment of a method of anchoring a connector to a proximal anchor by an elongate wedging device comprising multiple branches or bristles. In the embodiment shown in FIG. 4K, proximal anchor 14 comprises a connector opening 100 through which a connector 16 passes. An elongate wedging element 134 also passes through proximal anchor 14 such that one end of wedging element 134 can be pulled by a user. The embodiment of wedging element 134 shown in FIG. 4K comprises an elongate wedging shaft 136. One or more branches or bristles 138 are connected to wedging shaft 136. In one embodiment, wedging shaft 136 and bristles 138 are made of suitable polymeric materials. Examples of such polymeric materials include, but are not limited to polyester, polyimide, PEEK, polyurethane, etc. In one embodiment, one or more bristles 138 are connected to each other to form a web. The movement of proximal anchor 14 is restricted by a stopper 140. In the step shown in FIG. 4K, proximal anchor 14 is advanced over connector 16 to position proximal anchor 14 in a desired location. In the step shown in FIG. 4L, a user pulls wedging element 134. This causes a region of wedging element 134 comprising one or more bristles 138 to wedge between proximal anchor 14 and connector 16. This in turn locks connector 16 to proximal anchor 14. The excess length of connector 16 and/or wedging element 134 may be cut or trimmed.

The various wedging elements, lock pins, etc. disclosed herein may be deployed using one or more flexible pull shafts. For example, FIGS. 4M and 4N show longitudinal sections through an embodiment of a proximal anchor showing the steps of an embodiment of a method of anchoring a connector to a proximal anchor by a lock pin pulled by a flexible pull shaft. In FIG. 4M, proximal anchor 14 comprises a hollow elongate body comprising a connector opening 100 through which a connector 16 passes. Proximal anchor 14 encloses an elongate lock pin 104 comprising a tapering proximal end. A user can pull lock pin 104 in the proximal direction by pulling an elongate flexible pull shaft 142. Flexible pull shaft 142 is detachably attached to lock pin 104. The movement of proximal anchor 14 is restricted by a stopper 140. In the step shown in FIG. 4M, proximal anchor 14 is advanced over connector 16 to position proximal anchor 14 in a desired location. In the step shown in FIG. 4N, flexible pull shaft 142 is pulled in the proximal direction by a user. This pulls lock pin 104 in the proximal direction. Lock pin 104 wedges between connector 16 and proximal anchor 14. This locks connector 16 to proximal anchor 14. Flexible pull shaft 142 is detached from lock pin 104. In one embodiment, the attachment between flexible pull shaft 142 and lock pin 104 is designed to break at a pre-defined high force. In this embodiment, after the step of locking connector 16 to proximal anchor 14, flexible pull shaft 142 is pulled in the proximal direction at the pre-defined high force. This detaches flexible pull shaft 142 from lock pin 104. In another embodiment, the attachment between flexible pull shaft 142 and lock pin 104 is electrolytically detachable. In this embodiment, after the step of locking connector 16 to proximal anchor 14, an electric current is passed through the attachment between flexible pull shaft 142 and lock pin 104. This electrolytically dissolves the attachment between flexible pull shaft 142 and lock pin 104. This in turn detaches flexible pull shaft 142 from lock pin 104.

FIGS. 4O and 4P show longitudinal sections through an embodiment of a proximal anchor showing the steps of an embodiment of a method of anchoring a connector to the proximal anchor by a hollow wedging element. In FIG. 4O, proximal anchor 14 comprises a hollow elongate body comprising a connector opening 100 through which a connector 16 passes. Proximal anchor 14 encloses an elongate hollow wedging element 144 comprising a tapering distal end. Hollow wedging element 144 is made of suitable high tensile strength materials such that hollow wedging element 144 can be pushed over connector 16. Examples of such materials include, but are not limited to high stiffness polyimide, or PEEK, etc. The movement of proximal anchor 14 is restricted by a stopper 140. In the step shown in FIG. 4O, proximal anchor 14 is advanced over connector 16 to position proximal anchor 14 in a desired location. Hollow wedging element 144 is advanced over connector 16 while pulling connector 16 in the proximal direction. This causes hollow wedging element 144 to wedge between connector 16 and proximal anchor 14 as shown in FIG. 4P. This in turn attaches proximal anchor 14 to connector 16. In one embodiment, the lumen of hollow wedging element 144 is lined with one or more barbs or projections. The one or more barbs or projections allow motion of connector 16 through the lumen of hollow wedging element 144 in one direction and prevent or substantially resist motion of connector 16 through the lumen of hollow wedging element 144 in the opposite direction. In an alternate embodiment, wedging element 144 may be non-coaxial with connector 16. In another alternate embodiment, wedging element 144 may be pulled in a proximal direction in order to wedge wedging element 144 between connector 16 and proximal anchor 14.

The excess lengths of connector 16 and/or wedging elements may be cut or trimmed using a variety of mechanisms. For example, FIGS. 4Q and 4R show an embodiment of a method of using a compression cutter for cutting the excess length of connector 16 and a wedging element. In the step shown in FIG. 4Q, a connector 16 is attached to proximal anchor 14 by hollow wedging element 144. This may be done by the steps shown in FIGS. 4O-4P. A compression cutter 146 is advanced over hollow wedging element 144. Compression cutter 146 comprises two or more distal cutting edges. The outer surface of the distal cutting edges comprises an enlarged region as shown in FIG. 4Q. The enlarged region increases the radial profile of compression cutter 146 near the distal cutting edges. A compressing shaft 148 is advanced over compression cutter 146. In the step shown in FIG. 4R, compressing shaft 148 is advanced over the distal end of compression cutter 146. This exerts a radially inward force on the distal cutting edges. This in turn compresses the distal cutting edges causing them to cut the region of connector 16 and hollow wedging element 144 enclosed by the distal cutting edges. Thus excess lengths of connector 16 and hollow wedging element 144 are removed from proximal anchor 14.

FIGS. 4S and 4T show longitudinal sections through a first embodiment of a proximal anchor comprising a crimping zone showing the steps of an embodiment of a method of anchoring a connector to the proximal anchor. In FIG. 4S, proximal anchor 14 comprises a hollow elongate body comprising a connector opening 100. A connector 16 enters proximal anchor 14 through connector opening 100. Connector 16 exits proximal anchor 14 through one end of proximal anchor 14. The proximal end of proximal anchor 14 comprises a crimping zone 150. Crimping zone 150 can be crimped by a suitable radial compressive force. Crimping zone 150 is enclosed by an elongate crimping device 152 as shown in FIG. 4S. The distal end of crimping device 152 may be used to maintain the position of proximal anchor 14. The distal end of crimping device 152 is compressed by a compressing shaft 148. In the step shown in FIG. 4S, proximal anchor 14 is advanced over connector 16 to position proximal anchor 14 in a desired location. In the step shown in FIG. 4T, compressing shaft 148 is advanced over crimping device 152 in the distal direction till compression shaft 148 passes over the enlarged distal end of crimping device 152. This exerts a radially compressive force on the distal end of crimping device 152. Crimping device 152 in turn exerts a compressive force on crimping zone 150. This force compresses crimping zone 150 causing it to crimp over connector 16. This in turn causes proximal anchor 14 to attach to connector 16. The excess length of connector 16 may be cut or trimmed using a variety of cutting or trimming mechanisms.

FIGS. 4U and 4V show longitudinal sections through a second embodiment of a proximal anchor comprising a crimping zone showing the steps of an embodiment of a method of anchoring a connector to the proximal anchor. Proximal anchor 14 comprises a hollow elongate body comprising a connector opening 100. A connector 16 enters proximal anchor 14 through connector opening 100. Connector 16 exits proximal anchor 14 through one end of proximal anchor 14. The proximal end of proximal anchor 14 can be crimped by a suitable radial compressive force. The proximal end of proximal anchor 14 is enclosed by an elongate crimping shaft 154 as shown in FIG. 4U. Crimping shaft 154 encloses a lumen. The distal end of the lumen of crimping shaft 154 is tapered as shown in FIG. 4U, such that the diameter of the lumen gradually decreases till a certain distance along the proximal direction. Connector 16 passes through the lumen of crimping shaft 154 as shown in FIG. 4U. The distal end of crimping shaft 154 and a region of proximal anchor delivery device 34 may be used to maintain the position of proximal anchor 14. In the step shown in FIG. 4U, proximal anchor 14 is advanced over connector 16 to position proximal anchor 14 in a desired location. In the step shown in FIG. 4V, crimping shaft 154 is advanced in the distal direction. The proximal end of proximal anchor 14 is forced into the lumen of crimping shaft 154. The tapering lumen of crimping shaft 154 exerts a radially compressive force on the proximal end of proximal anchor 14. This force compresses the proximal end of proximal anchor 14 causing it to crimp over connector 16. This in turn causes proximal anchor 14 to attach to connector 16. The excess length of connector 16 may be cut or trimmed using a variety of cutting or trimming mechanisms.

Compression shaft 148 and crimping shaft 154 may be connected to a trigger mechanism to allow a user to controllably move compression shaft 148 and crimping shaft 154.

FIGS. 4W and 4X show a third embodiment of a proximal anchor comprising multiple crimping zones showing the steps of an embodiment of a method of anchoring a connector to the proximal anchor. In FIG. 4W, proximal anchor 14 comprises a hollow elongate body comprising a connector opening. A connector 16 enters proximal anchor 14 through the connector opening. Connector 16 exits proximal anchor 14 through one end of proximal anchor 14. Proximal anchor 14 comprises multiple crimping zones 150. Crimping zones 150 can be crimped by a suitable radial compressive force. In the embodiment of proximal anchor shown in FIG. 4W, proximal anchor 14 comprises three crimping zones 150. The crimping zones 150 are created in the material of proximal anchor 14 by creating U-shaped laser cuts. Each U-shaped cut encloses a flap that acts as a crimping zone 150. In the embodiment shown in FIG. 4W, the U-shaped laser cuts are aligned circumferentially. In an alternate embodiment, the U-shaped laser cuts are aligned along the axis of proximal anchor 14. The region of proximal anchor 14 comprising crimping zones 150 is enclosed by an elongate crimping device 152 as shown in FIG. 4W. The lumen of crimping device 152 may comprise one or more projections that coincide with crimping zones 150. The distal end of crimping device 152 comprises a tapering region as shown in FIG. 4W such that the outer diameter of crimping device 152 increases along the distal direction. The distal end of crimping device 152 is compressed by a compressing shaft 148. In the step shown in FIG. 4W, proximal anchor 14 is advanced over connector 16 to position proximal anchor 14 in a desired location. In the step shown in FIG. 4X, compressing shaft 148 is advanced over crimping device 152 in the distal direction till compression shaft 148 passes over the tapering distal end of crimping device 152. This exerts a radially compressive force on the distal end of crimping device 152. Crimping device 152 in turn exerts a compressive force on crimping zones 150. This force compresses crimping zones 150 causing them to crimp over connector 16. This in turn causes proximal anchor 14 to attach to connector 16. The excess length of connector 16 may be cut or trimmed using a variety of cutting or trimming mechanisms.

FIG. 4Y shows a side view of an embodiment of a proximal anchor comprising a tapering outer surface. In the embodiment shown in FIG. 4Y, proximal anchor 14 comprises an elongate tapering body with effective diameter "d" at one end smaller than effective diameter "D" at the other end. Proximal anchor 14 further comprises an external groove or slot 156 on the outer surface of the elongate tapering body. Examples of suitable biocompatible materials that may be used to construct proximal anchor 14 include, but are not limited to metals e.g. nickel-titanium alloy (e.g., nickel-titanium alloy (e.g., nitinol)), stainless steel, titanium, polymers (e.g. polyester, polyimide, PEEK, polyurethane, etc.

FIGS. 4Z through 4AB show side views of the embodiment of the proximal anchor of FIG. 4Y showing the steps of an embodiment of a method of anchoring a connector to the proximal anchor by an anchoring ring. In the step shown in FIG. 4Z, proximal anchor 14 is positioned at a desired location in the anatomy along a connector 16 such that a portion of connector 16 passes through slot 156. An anchoring ring 158 is advanced over proximal anchor 14. Examples of suitable biocompatible materials that may be used to construct anchoring ring 158 include, but are not limited to metals e.g. nickel-titanium alloy (e.g., nitinol), stainless steel, titanium, etc.; polymers e.g. polyester, polyimide, PEEK, polyurethane, etc. Anchoring ring 158 is advanced over proximal anchor 14 by a suitable pushing device. In one embodiment, the pushing device is a hollow, elongate pushing rod. As anchoring ring 158 is advanced over proximal anchor 14, the diameter of the region of proximal anchor 14 enclosed by anchoring ring 158 increases. After anchoring ring 158 is advanced to a certain distance along proximal anchor 14, anchoring ring 158 firmly grips the outer surface of proximal anchor 14. This causes a region of connector 16 to be compressed between a region of anchoring ring 158 and a region of proximal anchor 14. This in turn causes proximal anchor 14 to attach to connector 16. The excess length of connector 16 may be cut or trimmed using a variety of cutting or trimming mechanisms. In one embodiment of a method of cutting or trimming connector 16, a cutting ring 160 is advanced over proximal anchor 14 as shown in FIG. 4AA. Examples of suitable biocompatible materials that may be used to construct cutting ring 160 include, but are not limited to metals e.g. nickel-titanium alloy (e.g., nitinol), stainless steel, titanium, etc.; polymers e.g. polyester, polyimide, PEEK, polyurethane, etc. Cutting ring 160 comprises a circular body that is attached to a cutting blade 162. As cutting ring 160 is advanced over proximal anchor 14, the diameter of the region of proximal anchor 14 enclosed by cutting ring 160 increases. After cutting ring 160 is advanced to a certain distance along proximal anchor 14, cutting blade 162 comes into contact with a region of connector 16. Cutting ring 160 is advanced further to cut connector 16 by cutting blade 162 as shown in FIG. 4AB.

FIG. 4AC shows a cross sectional view of an embodiment of the cutting ring of FIGS. 4AA and 4AB. In the embodiment shown in FIG. 4AC, cutting ring 160 comprises a circular body that is attached to a cutting blade 162 that projects radially inwards.

FIG. 4AD shows a side view of a first embodiment of a proximal anchor made of a thermal shape memory alloy. In FIG. 4AD, proximal anchor 14 comprises a hollow elongate body made of a suitable shape memory material. Examples of such shape memory materials include, but are not limited to nickel-titanium alloys (nickel-titanium alloy (e.g., nitinol)), copper-aluminum-nickel alloys, copper-zinc-aluminum alloys, iron-manganese-silicon alloys, etc. In the embodiment shown in FIG. 4AD, proximal anchor 14 is made of nickel-titanium alloy (e.g., nitinol). Proximal anchor 14 encloses a lumen. One end of proximal anchor 14 may be plugged by a lumen plug 164. In the embodiment shown in FIG. 4AD, proximal anchor 14 also comprises a longitudinal slit. The longitudinal slit creates a fluid communication between the lumen of proximal anchor 14 and the exterior of proximal anchor 14. Proximal anchor 14 comprises a connector opening 100. A connector 16 enters proximal anchor 14 through connector opening 100. Connector 16 exits proximal anchor 14 through one end of proximal anchor 14. A user can control the diameter of the lumen of proximal anchor 14 by changing the temperature of proximal anchor 14. In one embodiment of a method of anchoring proximal anchor 14 to connector 16, proximal anchor 14 is introduced in the anatomy in the martensite phase of the shape memory material of proximal anchor 14. The diameter of the lumen of proximal anchor 14 in the martensite state is sufficiently large to allow proximal anchor 14 to be advanced over connector 16. The martensite phase may be achieved for example, by cooling proximal anchor 14 and introducing the cooled proximal anchor 14 in the anatomy. After proximal anchor 14 warms up to the body temperature, the shape memory material recovers a programmed shape and becomes super-elastic. In the programmed shape, the diameter of the lumen of proximal anchor 14 is sufficiently small to allow proximal anchor 14 to attach to connector 16. The excess length of connector 16 may be cut or trimmed using a variety of cutting or trimming mechanisms. In one method embodiment, the temperature of proximal anchor 14 is maintained or changed by controlling the temperature of a liquid such as saline that is brought into contact with proximal anchor 14 by a user. In one embodiment, the lumen of proximal anchor 14 is lined with one or more barbs or projections. The one or more barbs or projections allow motion of connector 16 through the lumen of proximal anchor 14 in one direction and prevent or substantially resist motion of connector 16 through the lumen of proximal anchor 14 in the opposite direction.

FIG. 4AE shows a cross section of the proximal anchor of FIG. 4AD through the line 4AE-4AE when the shape memory material of the proximal anchor is in the martensite phase. In FIG. 4AE, the diameter of the lumen of proximal anchor 14 is larger than the outer diameter of proximal anchor 14. This allows a user to advance proximal anchor 14 over connector 16. FIG. 4AE' shows a cross section of the proximal anchor of FIG. 4AD through the line 4AE-4AE when the shape memory material of the proximal anchor is in the programmed shape. In FIG. 4AE', the diameter of the lumen of proximal anchor 14 is smaller than the outer diameter of proximal anchor 14. This causes a region of proximal anchor 14 to compress a region of connector 16. This in turn causes proximal anchor 14 to attach to connector 16.

FIG. 4AF shows a cross section of the proximal anchor of FIG. 4AD through the line 4AF-4AF when the shape memory material of the proximal anchor is in the martensite phase. In FIG. 4AF, the diameter of the lumen of proximal anchor 14 is larger than the outer diameter of lumen plug 164. FIG. 4AF' shows a cross section of the proximal anchor of FIG. 4AD through the line 4AF-4AF when the shape memory material of the proximal anchor is in the programmed shape. In FIG. 4AF', the diameter of the lumen of proximal anchor 14 is smaller than the outer diameter of lumen plug 164. This causes lumen plug 164 to substantially plug one end of the lumen of proximal anchor 14.

FIG. 4AG shows a side view of a second embodiment of a proximal anchor made of a thermal shape memory alloy. In FIG. 4AG, proximal anchor 14 comprises a hollow elongate body made of a suitable shape memory material. Examples of such shape memory materials include, but are not limited to nickel-titanium alloys (nickel-titanium alloy (e.g., nitinol)), copper-aluminum-nickel alloys, copper-zinc-aluminum alloys, iron-manganese-silicon alloys, etc. In the embodiment shown in FIG. 4AG, proximal anchor 14 is made of nickel-titanium alloy (e.g., nitinol). Proximal anchor 14 encloses a lumen. One end of proximal anchor 14 may be plugged. In the embodiment shown in FIG. 4AG, proximal anchor 14 comprises two or more shape memory arms 166. Proximal anchor 14 comprises a connector opening 100. A connector 16 enters proximal anchor 14 through connector opening 100. Connector 16 exits proximal anchor 14 through the region enclosed by shape memory arms 166. A user can control the size of the region enclosed by shape memory arms 166 by changing the temperature of proximal anchor 14. In one embodiment of a method of anchoring proximal anchor 14 to connector 16, proximal anchor 14 is introduced in the anatomy in the martensite phase of the shape memory material of shape memory arms 166. The size of the region enclosed by shape memory arms 166 in the martensite state is sufficiently large to allow proximal anchor 14 to be advanced over connector 16. The martensite phase may be achieved for example, by cooling proximal anchor 14 and introducing the cooled proximal anchor 14 in the anatomy. After proximal anchor 14 warms up to the body temperature, the shape memory material recovers a programmed shape and becomes super-elastic. In the programmed shape, the size of the region enclosed by shape memory arms 166 is sufficiently small to cause shape memory arms 166 to compress a region of connector 16. This causes proximal anchor 14 to attach to connector 16. The excess length of connector 16 may be cut or trimmed using a variety of cutting or trimming mechanisms. In one method embodiment, the temperature of proximal anchor 14 is maintained or changed by controlling the temperature of a liquid such as saline that is brought into contact with proximal anchor 14 by a user. In one embodiment, the lumen of proximal anchor 14 is lined with one or more barbs or projections. The one or more barbs or projections allow motion of connector 16 through the lumen of proximal anchor 14 in one direction and prevent or substantially resist motion of connector 16 through the lumen of proximal anchor 14 in the opposite direction.

FIG. 4AH shows a cross section of the proximal anchor of FIG. 4AG through the line 4AH-4AH when the shape memory material of the proximal anchor is in the martensite phase. In FIG. 4AH, the size of the region enclosed by shape memory arms 166 is larger than the outer diameter of proximal anchor 14. This allows a user to advance proximal anchor 14 over connector 16. FIG. 4AH' shows a cross section of the proximal anchor of FIG. 4AG through the line 4AH-4AH when the shape memory material of the proximal anchor is in the programmed shape. In FIG. 4AH', the size of the region enclosed by shape memory arms 166 is smaller than the outer diameter of proximal anchor 14. This causes the region enclosed by shape memory arms 166 to compress a region of connector 16. This in turn causes proximal anchor 14 to attach to connector 16.

FIGS. 4AI and 4AJ show longitudinal sections of an embodiment of a proximal anchor showing the steps of an embodiment of a method of anchoring a looped or folded region of the connector to the proximal anchor. Proximal anchor 14 comprises a hollow elongate body. A pull wire 168 passes through the hollow proximal anchor 14. Pull wire 168 loops around connector 16 and reenters proximal anchor 14 as shown in FIG. 4AI. Thus, the loop of pull wire 168 pulls connector 16 towards proximal anchor 14. In FIG. 4AI, the loop of pull wire 168 is advanced over connector 16. This causes proximal anchor 14 to be advanced over connector 16. Proximal anchor 14 is advanced to position proximal anchor 14 in a desired location. In the step shown in FIG. 4V, pull wire 168 is pulled by a user. This pulls a loop of connector 16 inside proximal anchor 14. The loop of connector 16 pulled inside proximal anchor 14 wedges inside the lumen of proximal anchor 14. This in turn causes connector 16 to attach to proximal anchor 14. The excess length of connector 16 and/or pull wire 168 may be cut or trimmed using a variety of cutting or trimming mechanisms.

FIG. 4AK shows a side view of an embodiment of a proximal anchor made of a suitable elastic or super elastic or shape memory material comprising one or more inwardly opening flaps. In FIG. 4AK, proximal anchor 14 comprises a hollow tubular body. The hollow tubular body is made of a suitable elastic or super elastic or shape memory material. Examples of such materials include, but are not limited to metals such as nickel-titanium alloy (e.g., nitinol), stainless steel, titanium, etc. and polymers such as shape memory polymers, etc. The tubular body comprises one or more inwardly opening flaps 20. In the embodiment shown in FIG. 4AK, inwardly opening flaps 20 are oriented along the axis of proximal anchor 14. Inwardly opening flaps 20 allow the motion of a connector 16 that passes through proximal anchor 14 along the direction of orientation of inwardly opening flaps 20. Also, inwardly opening flaps 20 prevent the motion of connector 16 that passes through proximal anchor 14 along the direction opposite to the direction of orientation of inwardly opening flaps 20. This enables proximal anchor 14 to be advanced over connector 16 along one direction. In one embodiment, proximal anchor 14 is made of an elastic or super elastic material. In this embodiment, proximal anchor 14 is introduced in the anatomy by sliding proximal anchor 14 over connector 16 in the direction of orientation of inwardly opening flaps 106. Proximal anchor 14 is advanced over connector 16 till proximal anchor 14 is located in a desired location. Inwardly opening flaps 106 prevent the motion of proximal anchor 106 connector 16 in the direction opposite to the direction of orientation of inwardly opening flaps 106. In another embodiment, proximal anchor 14 is made of a shape memory material such as nickel-titanium alloy (e.g., nitinol). In this embodiment, proximal anchor 14 is introduced in the anatomy in the martensite phase of nickel-titanium alloy (e.g., nitinol). In this state, inwardly opening flaps 20 are aligned substantially parallel to the surface of proximal anchor 14. This allows proximal anchor 14 to be advanced over connector 16. The martensite phase may be achieved, for example, by cooling proximal anchor 14 and introducing the cooled proximal anchor 14 in the anatomy. After proximal anchor 14 warms up to the body temperature, the nickel-titanium alloy (e.g., nitinol) recovers a programmed shape and becomes super-elastic. In the programmed shape, inwardly opening flaps 20 are bent inwards into the lumen of proximal anchor 14. This attaches proximal anchor 14 to connector 16.

FIG. 4AL shows a longitudinal section through the embodiment of the proximal anchor of FIG. 4AK. Proximal anchor 14 comprises a hollow tubular body comprising one or more inwardly opening flaps 20. Inwardly opening flaps 20 prevent the motion of connector 16 along the direction opposite to the direction of orientation of inwardly opening flaps 20.

In an alternate embodiment, proximal anchor 14 is attached to connector 16 using a biocompatible adhesive. The biocompatible adhesive may be introduced by a suitable proximal anchor delivery device 34 that comprises an adhesive injecting tube. In one embodiment of a method of attaching proximal anchor 14 to connector 16, proximal anchor 14 is positioned at a desired location relative to connector 16. A suitable biocompatible adhesive is introduced such that the adhesive attaches proximal anchor 14 to a location on connector 16. In one embodiment, the adhesive is introduced through a lumen in actuator 120.

Figure 5A:
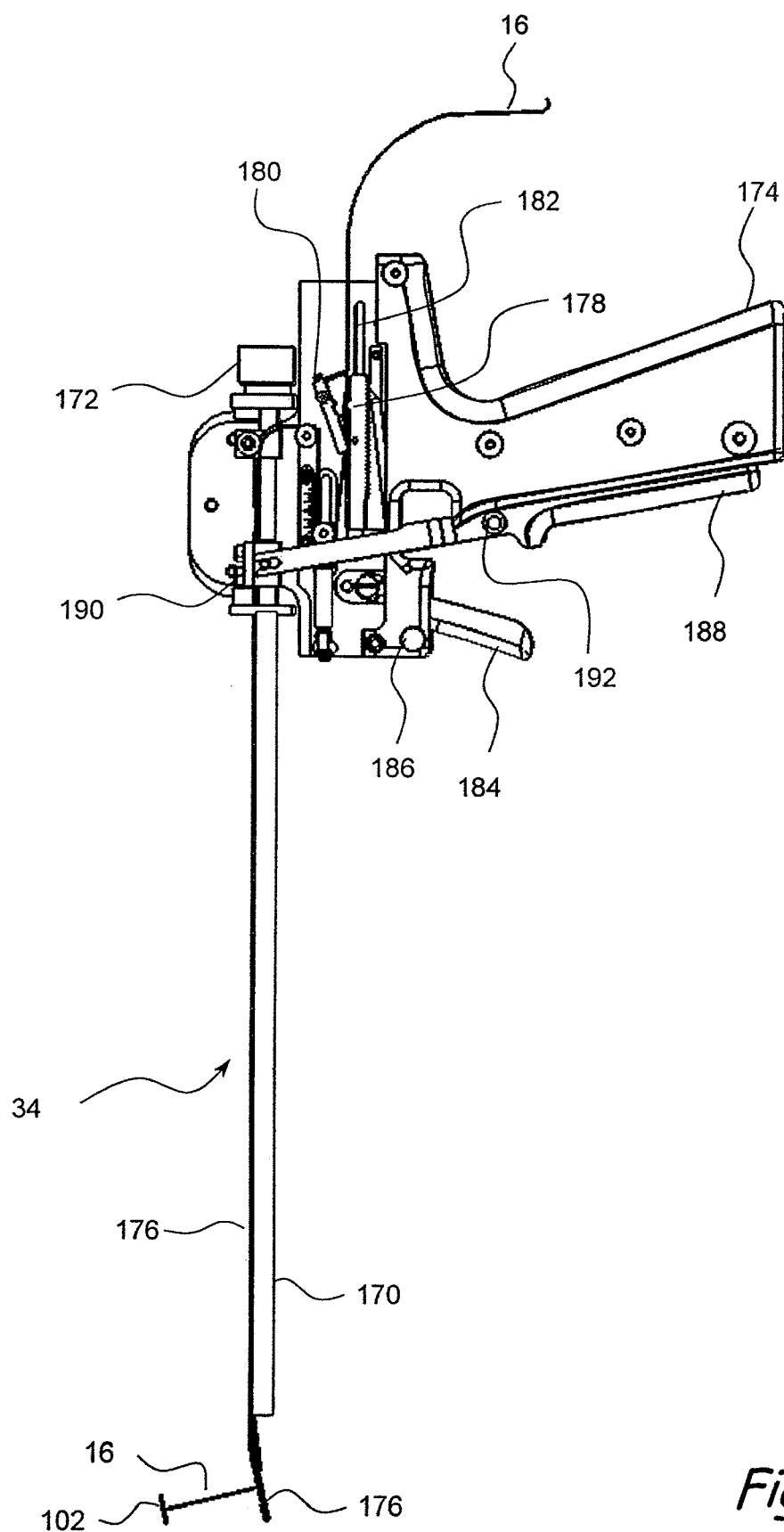
FIG. 5A shows a side view of a first embodiment of a proximal anchor delivery device comprising one or more finger activated triggers.
Figure 5:
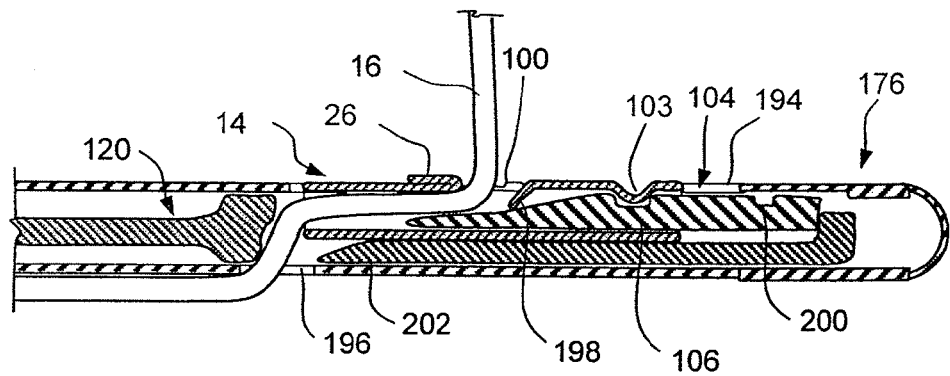
FIGS. 5B through 5D show longitudinal sections through the distal tip of the proximal anchor delivery device of FIG. 5A showing the steps of a method of deploying a proximal anchor in the anatomy.
FIG. 5E shows a side view of a proximal anchor similar to the proximal anchor in FIGS. 5B-5D having a undeployed lock pin partially inserted into the proximal anchor.
FIGS. 5F through 5H show longitudinal sections through the proximal anchor and the lock pin of FIG. 5E showing the steps of a method of attaching the proximal anchor to a connector using the lock pin.
FIG. 5I shows a side view of an embodiment of a lock pin that can be used to lock a connector to a proximal anchor as shown in the method of FIGS. 5B-5D.
FIG. 5J shows another side view of the lock pin of connector shown in FIG. 5I.
FIG. 5K shows an isometric view of an embodiment of an actuator that can be used to drive a lock pin into a proximal anchor.
FIG. 5L shows a side view of the embodiment of the actuator shown in FIG. 5K.
FIG. 5M shows a longitudinal section through the actuator of FIG. 5L.
FIG. 5N shows a side view of a second embodiment of a proximal anchor delivery device.
FIGS. 5O through 5S show the steps of an embodiment of a method of deploying an anchor in an anatomical region using the proximal anchor delivery device of FIG. 5N.
FIG. 5T shows the distal end of an embodiment of a proximal anchor delivery device comprising an anchor tube with a bent, curved or angled distal end.
FIG. 5U shows the step of deploying a proximal anchor in an anatomical region by the proximal anchor delivery device of FIG. 5T.
FIG. 5V shows a cystoscopic view of a region of canine urethra enclosed by the prostate gland that has been treated by a procedure similar to the procedure shown in FIGS. 1D through 1J.
Figure 5:
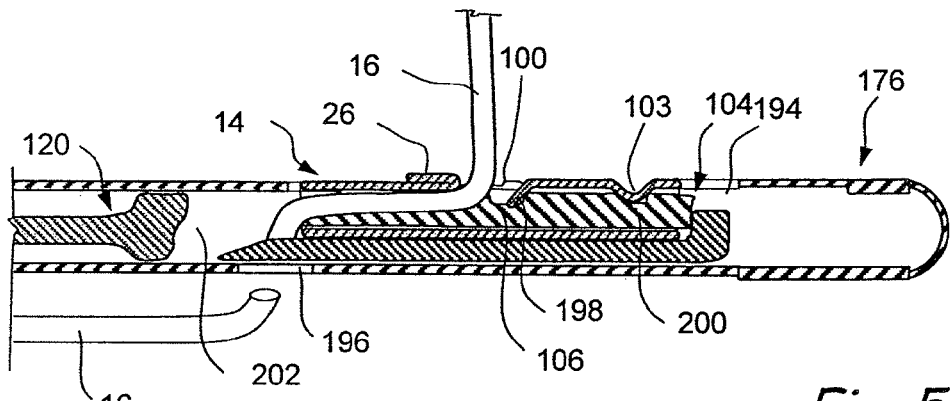
Figure 5:
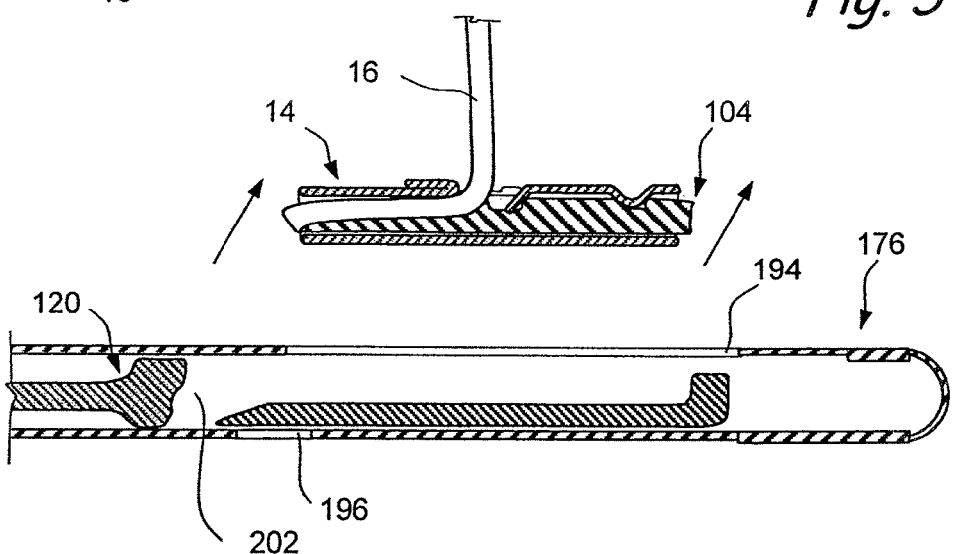
Figure 5:
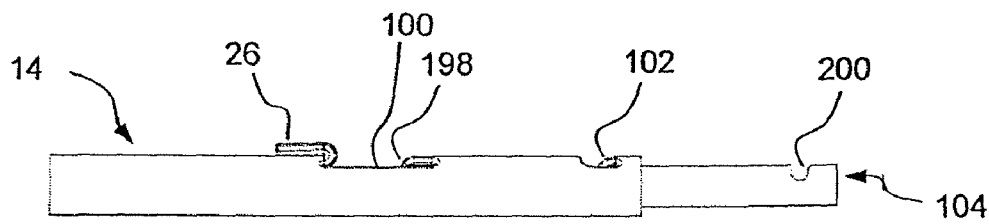
Figure 5:
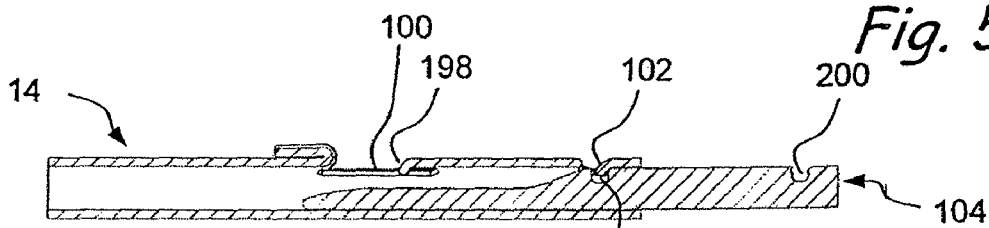
Figure 5:
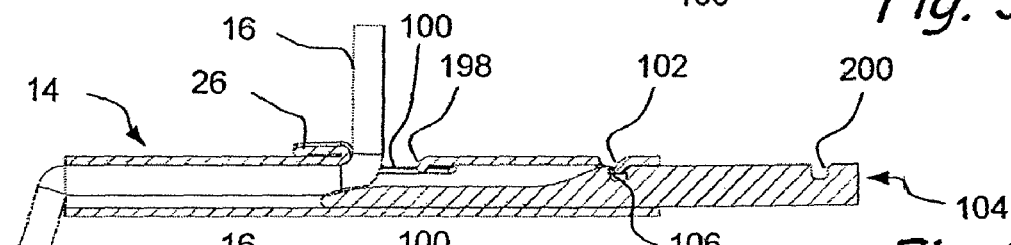
Figure 5:
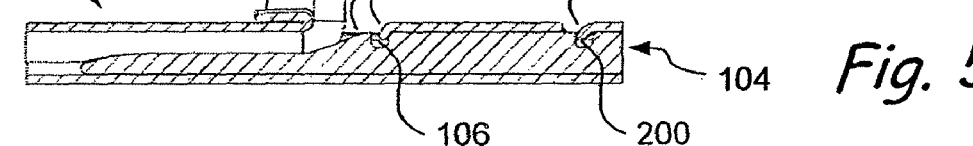
Figure 5:
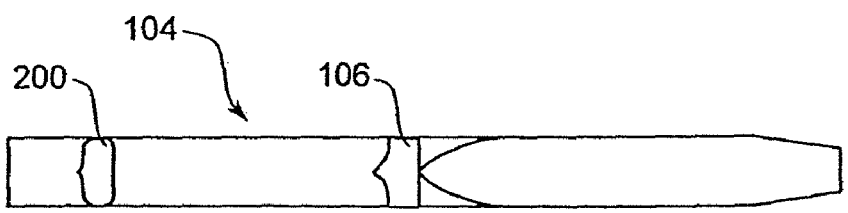
Figure 5:
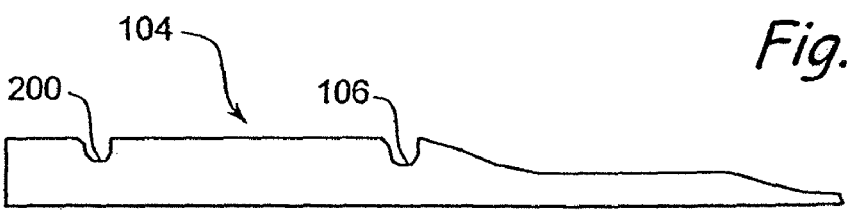

FIG. 5A shows a side view of a first embodiment of a proximal anchor delivery device comprising one or more finger activated triggers. The embodiment of proximal anchor delivery device 34 shown in FIG. 5A comprises an elongate endoscope channel 170. Elongate endoscope channel 170 may be made of suitable biocompatible materials. Examples of such materials include, but not limited to polymers e.g. polyester, polyimide, PEEK, polyurethane, polysulfone, polyetherimides, polycarbonate, and may be filled with glass or reinforcing fiber, etc; metals e.g. stainless steel, titanium, etc. In one embodiment, endoscope channel 170 is made of 316 stainless steel. The proximal end of endoscope channel 170 comprises an endoscope adapter hub 172. Endoscope adapter hub 172 allows a user to introduce an endoscope through the proximal end of endoscope channel 170. The proximal region of endoscope channel 170 is attached to a handle 174. Proximal anchor delivery device 34 further comprises an elongate anchor tube 176. Anchor tube 176 may be made of suitable biocompatible materials. Examples of such materials include, but not limited to polymers e.g. polyester, polyimide, PEEK, polyurethane, polysulfone, polyetherimides, polycarbonate, and may be filled with glass or reinforcing fiber, etc. metals e.g. stainless steel, titanium, nickel-titanium alloy (e.g., nitinol), etc. In one embodiment, anchor tube 176 is made of 316 stainless steel. The distal end of anchor tube 176 may comprise a blunt or atraumatic tip. Anchor tube 176 is attached to endoscope channel 170 such that anchor tube 176 is substantially parallel to endoscope channel 170 as shown in FIG. 5A. Anchor tube 176 comprises a lumen that encloses proximal anchor 14. Proximal anchor 14 is deployed in the anatomy through the distal region of anchor tube 176. The distal region of anchor tube 176 may comprise a bent, curved or angled region. Proximal anchor delivery device 34 is used to attach a proximal anchor 14 to a desired location on a connector 16. A suitable tension may be introduced into connector 16 before the step of attaching proximal anchor 14 to connector 16. In order to introduce this desired tension, proximal anchor delivery device 34 further comprises a tensioning mechanism. In the embodiment shown in FIG. 5A, the tensioning mechanism comprises a pulling mechanism. The pulling mechanism pulls connector 16 between a sliding rack 178 and a suture trap 180. Suture trap 180 is hinged to sliding rack 178 as shown in FIG. 5A. Sliding rack 178 moves on a sliding slot 182 located on handle 174. In one embodiment, various components of the pulling mechanism are constructed from stainless steel 304 and nickel-titanium alloy (e.g., nitinol). The step of moving sliding rack 178 on sliding slot 182 is performed by pulling a first trigger 184 attached to handle 174. Handle 174 may comprise a first trigger safety 186 to prevent unwanted movement of first trigger 184. After a desired tension has been created in connector 16, proximal anchor 14 may be deployed in the anatomy by a second trigger 188. In the embodiment shown in FIG. 5A, second trigger 188 comprises an elongate lever. One end of the elongate lever is hinged to handle 174. The other end of elongate lever is pivotally attached to an actuator block 190. Actuator block 190 slides over the outer surface of endoscope channel 170. Actuator block 190 is connected to an elongate actuator. The movement of the elongate actuator cuts connector 16 and also attaches proximal anchor 14 to connector 16. Handle 174 may comprise a second trigger safety 192 to prevent unwanted movement of second trigger 188.

In the embodiment shown in FIG. 5A, a portion of connector 16 passes through anchor tube 176. In an alternate embodiment, proximal anchor delivery device 34 further comprises an elongate suture tube. The suture tube is attached to the outer surface of endoscope channel 170. The distal end of the suture tube is attached to anchor tube 176 around second anchor tube opening 196 such that connector 16 emerges out of second anchor tube opening 196 and passes through the suture tube. Connector 16 emerges out of the proximal end of the suture tube and further passes through the tensioning mechanism.

In one embodiment, proximal anchor delivery device 34 is sized to be introduced through a 25F cystoscope sheath. The length of proximal anchor delivery device 34 within the sheath ranges from 6 to 14 inches. In this embodiment, endoscope channel 170 and endoscope adapter hub 172 are designed to fit a 4 mm telescope. In this embodiment, the outer diameter of endoscope channel 170 ranges from 0.174 to 0.200 inches and the inner diameter of endoscope channel 170 ranges from 0.160 to 0.180 inches. In this embodiment, the outer diameter of anchor tube 176 ranges from 0.050 to 0.072 inches and the inner diameter of anchor tube 176 ranges from 0.030 to 0.063 inches. In this embodiment, the maximum distance through which the actuator travels ranges from 0.060 to 0.300 inches. In a preferred embodiment, proximal anchor delivery device 34 is sized to be introduced through a 25F cystoscope sheath. The length of proximal anchor delivery device 34 within the sheath ranges from is approximately 10 inches. In this preferred embodiment, endoscope channel 170 and endoscope adapter hub 172 are designed to fit a Storz 4 mm telescope. In this preferred embodiment, the outer diameter of endoscope channel 170 is approximately 0.180 inches and the inner diameter of endoscope channel 170 is approximately 0.160 inches. In this preferred embodiment, the outer diameter of anchor tube 176 is approximately 0.059 inches and the inner diameter of anchor tube 176 is approximately 0.046 inches. In this preferred embodiment, the maximum distance through which the actuator travels is approximately 0.240 inches.

FIGS. 5B through 5D show longitudinal sections through the distal tip of the proximal anchor delivery device of FIG. 5A showing the steps of a method of deploying a proximal anchor in the anatomy. In the step shown in FIG. 5B, proximal anchor 14 is enclosed in the distal region of anchor tube 176. In the embodiment shown in FIG. 5B, anchor tube 176 comprises a first anchor tube opening 194 and a second anchor tube opening 196. Connector 16 enters anchor tube 176 through first anchor tube opening 194. Connector 16 passes through proximal anchor 14 and emerges out of anchor tube 176 through second anchor tube opening 196. In the embodiment shown in FIG. 5B, proximal anchor 14 comprises a hollow tube. Proximal anchor 14 comprises a locking crimp 103. The hollow tube further comprises a connector opening 100 located roughly midway between the ends of the tube. One edge of connector opening 100 is lined with an outwardly opening flap 26. Outwardly opening flap 26 is folded as shown in FIG. 5B to create a blunt edge to connector opening 100. The opposite edge of connector opening comprises a second locking tab 198. Second locking tab 198 is made by cutting a flap in the material of proximal anchor 14 and bending the flap into the lumen of proximal anchor 14 as shown. Connector 16 is locked to proximal anchor 14 by driving a lock pin 104 into proximal anchor 14. In FIG. 5B, lock pin 104 is partially inserted into proximal anchor 14 such that the length of the combination of lock pin 104 and proximal anchor 14 is more than the length of first anchor tube opening 194. This prevents unwanted separation of proximal anchor 14 from anchor tube 176 through second anchor tube opening 196. In the embodiment shown in FIG. 5B, lock pin 104 comprises a locking slot 106. Locking slot 106 allows lock pin 104 to lock to proximal anchor 14 by locking crimp 103. Lock pin 104 further comprises a second locking slot 200. In one embodiment, the distance from locking slot 106 to second locking slot 200 along the length of lock pin 104 is the same as the distance from second locking tab 198 to locking crimp 103 along the length of proximal anchor 14. In another embodiment, the distance from locking slot 106 to second locking slot 200 along the length of lock pin 104 is slightly more than the distance from second locking tab 198 to locking crimp 103 along the length of proximal anchor 14. In a preferred embodiment, proximal anchor 14 and lock pin 104 are made of stainless steel 316L. In the preferred embodiment, tube 24 is laser cut and then electropolished. Lock pin 104 is constructed using EDM (electrical discharge machining) and then passivated. The geometries of proximal anchor 14, connector 16 and lock pin 104 enable lock pin 104 to lock connector 16 to proximal anchor 14. In a preferred embodiment, the length of proximal anchor 14 is 0.236 inches, the outer diameter of proximal anchor 14 is 0.027 inches, the inner diameter of proximal anchor 14 is 0.020 inches, the length of lock pin 104 is 0.236 inches and the outer diameter of lock pin 104 is 0.019 inches.

In the embodiment shown in FIG. 5B, lock pin 104 is driven into proximal anchor 14 by an actuator 120. In the embodiment shown in FIG. 5B, actuator 120 comprises a bent distal tip. The bent distal tip forms a distal edge that is in contact with the distal end of lock pin 104. Actuator 120 further comprises an actuator opening 202. The distal edge of actuator opening 202 may be sharpened. Actuator opening 202 is located near second anchor tube opening 196 such that connector 16 passes through both actuator opening 202 and second anchor tube opening 196. In the step shown in FIG. 5B, a desired tension is created in connector 16.

In the step shown in FIG. 5C, actuator 120 is pulled in the proximal direction by a user. This causes the bent distal tip of actuator 120 to drive lock pin 104 towards proximal anchor 14. This in turn causes locking crimp 103 to unlock from locking slot 106. Lock pin 104 then moves in the proximal direction till locking crimp 103 locks into second locking slot 200 and second locking tab 198 locks into locking slot 106. This causes lock pin 104 to lock to proximal anchor 14. In this configuration, lock pin is inserted into proximal anchor 14 such that the length of the combination of lock pin 104 and proximal anchor 14 is smaller than the length of first anchor tube opening 194. The movement of lock pin 104 along the proximal direction further causes the proximal tapering end of lock pin 104 to wedge between proximal anchor 14 and connector 16. Thus, proximal anchor 14 is locked to connector 16. Further, pulling actuator 120 in the proximal direction causes connector 16 to get sheared between the edges of actuator opening 202 and second anchor tube opening 196. This cuts connector 16.

In the step shown in FIG. 5D, proximal anchor 14 is pulled by the tension in connector 16. Since the length of the combination of lock pin 104 and proximal anchor 14 is less than the length of first anchor tube opening 194, proximal anchor 14 emerges out of anchor tube 176 through first anchor tube opening 194. Thus, proximal anchor 14 is deployed in the anatomy.

FIG. 5E shows a side view of a proximal anchor similar to the proximal anchor in FIGS. 5B-5D having an undeployed lock pin partially inserted into the proximal anchor.

FIGS. 5F through 5H show longitudinal sections through the proximal anchor and the lock pin of FIG. 5E showing the steps of a method of attaching the proximal anchor to a connector using the lock pin. In FIG. 5E, proximal anchor 14 comprises locking tab 102 and second locking tab 198. Lock pin 104 comprises locking slot 106 and second locking slot 200. In FIG. 5E, locking tab 102 of proximal anchor 14 locks into locking slot 106 on lock pin 104. Thus lock pin 104 is temporarily locked to proximal anchor 14 in an undeployed configuration. In the step shown in FIG. 5G, connector 16 is passed through proximal anchor 14. In the embodiment shown in FIG. 5G, connector 16 enters proximal anchor 14 through connector opening 100 and exits proximal anchor 14 through the proximal end of proximal anchor 14. In the step shown in FIG. 5H, lock pin 104 is moved by a user along the proximal direction into proximal anchor 14. Lock pin 104 is moved until locking tab 102 locks into second locking slot 200 and second locking tab 198 locks into locking slot 106. This causes lock pin 104 to lock to proximal anchor 14. Also, the proximal tapering end of lock pin 104 wedges between proximal anchor 14 and connector 16. Thus, proximal anchor 14 is attached to connector 16. The excess length of connector 16 may be cut or trimmed.

Several embodiments of lock pin 104 may be used to lock connector 16 to proximal anchor 14. FIG. 5I shows a side view of an embodiment of a lock pin that can be used to lock connector 16 to proximal anchor 14 as shown in the method of FIGS. 5B-5D. In the embodiment shown in FIG. 5I, lock pin 104 is made from a cylinder of suitable biocompatible material. Examples of such biocompatible materials include, but are not limited to metals e.g. nickel-titanium alloy (e.g., nitinol), stainless steel, titanium, etc. or polymers e.g. EXAMPLES, etc. Lock pin 104 comprises a locking slot 106. Locking slot 106 allows lock pin 104 to lock to locking tab 102 of proximal anchor 14. Lock pin 104 further comprises a second locking slot 200 distal to locking slot 106. Lock pin 104 further comprises a tapering region proximal to locking slot 106. The tapering region acts as a wedge between the internal surface of proximal anchor 14 and connector 16, thereby locking connector 16 to proximal anchor 14. In one embodiment, the total length of lock pin 104 is about 0.236 inches. In this embodiment, lock pin 104 is made from a cylinder of stainless steel 316L of a diameter about 0.019 inches. In this embodiment, the length from the proximal tip of lock pin 104 to the proximal edge of locking slot 106 is about 0.122 inches. In this embodiment, the length from the proximal tip of lock pin 104 to the proximal edge of second locking slot 200 is about 0.206 inches. In one embodiment of a method for manufacturing lock pin 104, lock pin 104 is made by laser cutting a cylinder of a suitable biocompatible material.

FIG. 5J shows another side view of the lock pin of connector shown in FIG. 5I.

Figure 5K:
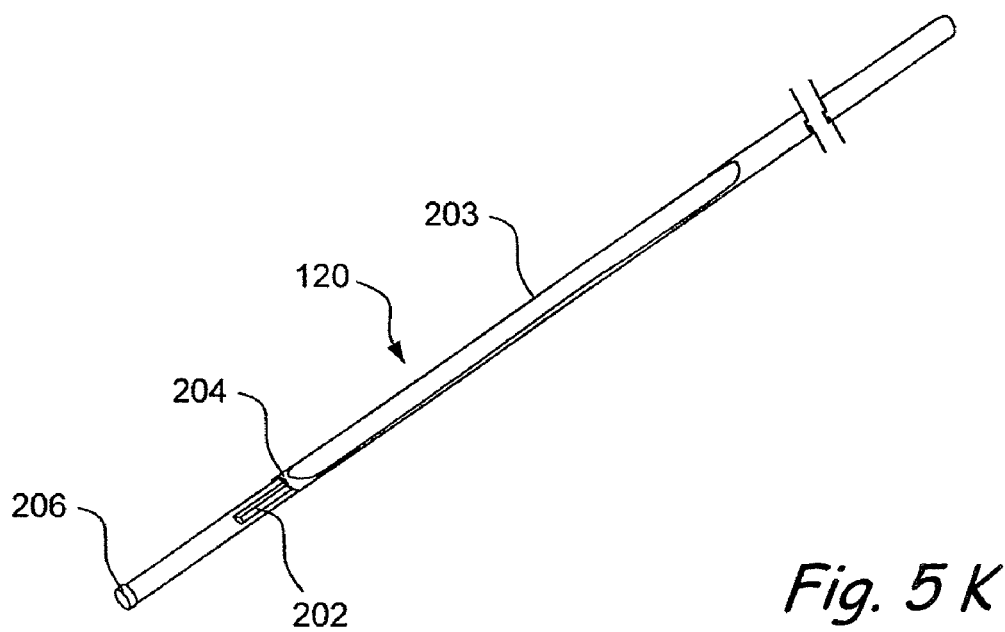

Several embodiments of actuator 120 may be used to drive lock pin 104 into proximal anchor 14 to lock connector 16 to proximal anchor 14. FIG. 5K shows an isometric view of an embodiment of an actuator 120 that can be used to drive lock pin 104 into proximal anchor 14. In the embodiment shown in FIG. 5K, actuator 120 comprises an elongate cylindrical or flattened pull rod 203. The proximal region of pull rod 203 is enlarged as shown in FIG. 5K. The distal region of actuator 120 comprises two projections: a proximal projection 204 and a distal projection 206. Proximal projection 204 and distal projection 206 are used to temporarily hold proximal anchor 14 between them. The region of actuator 120 between proximal projection 204 and a distal projection 206 comprises actuator opening 202.

Figure 5L:
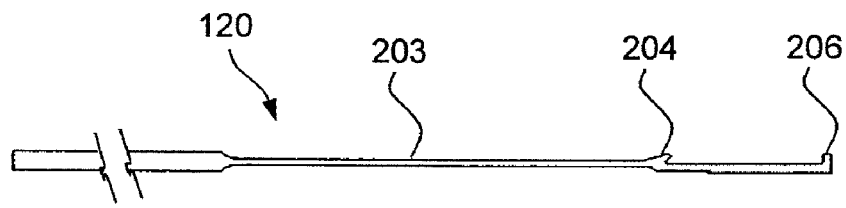

FIG. 5L shows a side view of the embodiment of the actuator shown in FIG. 5K. FIG. 5L shows actuator 120 comprising proximal projection 204 and distal projection 206. The region of actuator 120 between proximal anchor 14 and a distal projection 206 comprises actuator opening 202.

Figure 5M:
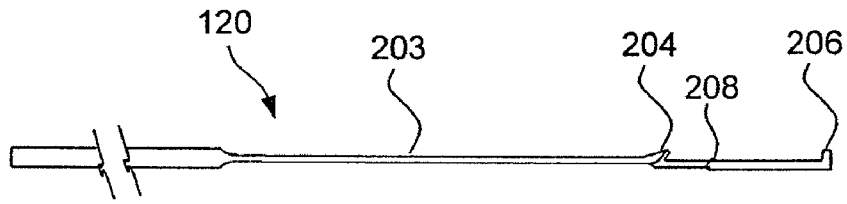

FIG. 5M shows a longitudinal section through the actuator of FIG. 5L. The distal edge of actuator opening 202 is sharpened to form an actuator cutting edge 208. In the embodiment shown in FIG. 5M, the angle between actuator cutting edge 208 and the longitudinal axis of actuator 120 is about 45 degrees. In one embodiment, the total length of actuator 120 is 14 inches. The distance between the proximal edge of distal projection 206 and the distal most region of proximal projection 204 is about 0.373 inches. In this embodiment, the length from the distal end of the enlarged proximal region of pull rod 203 to the distal end of actuator 120 is about 1.49 inches.

Figure 5N:
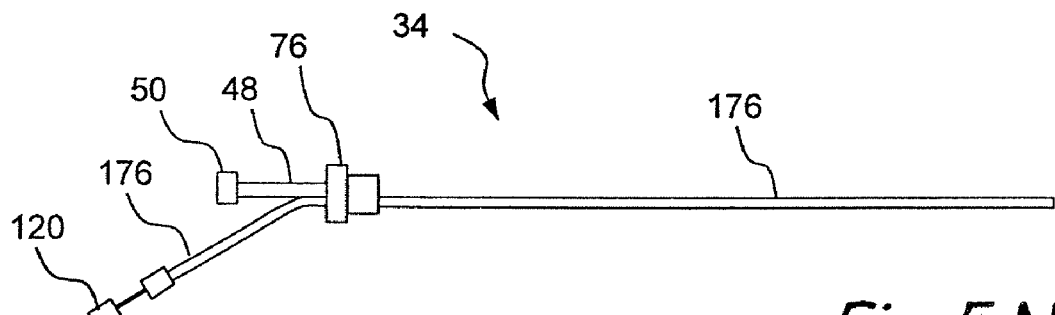
Figure 5:
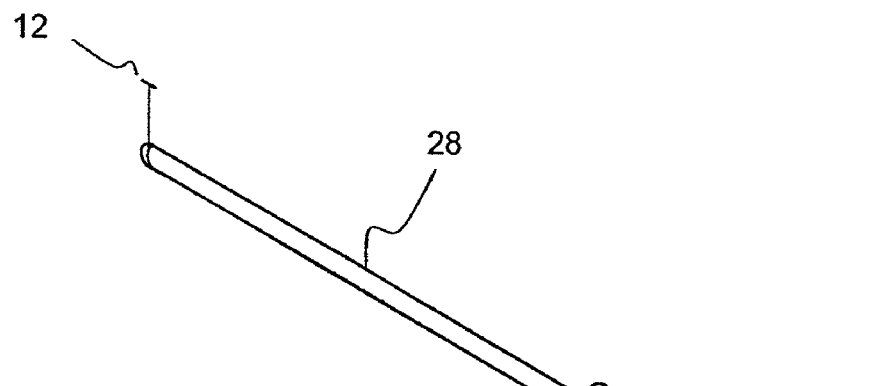
Figure 5:
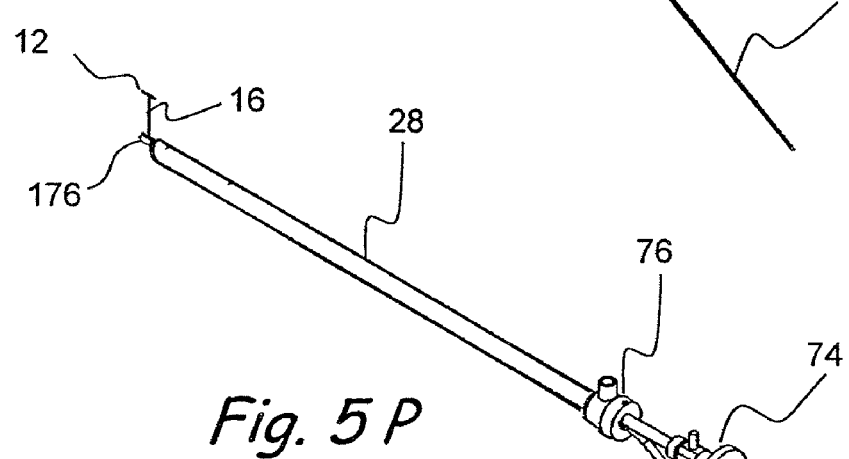
Figure 5:
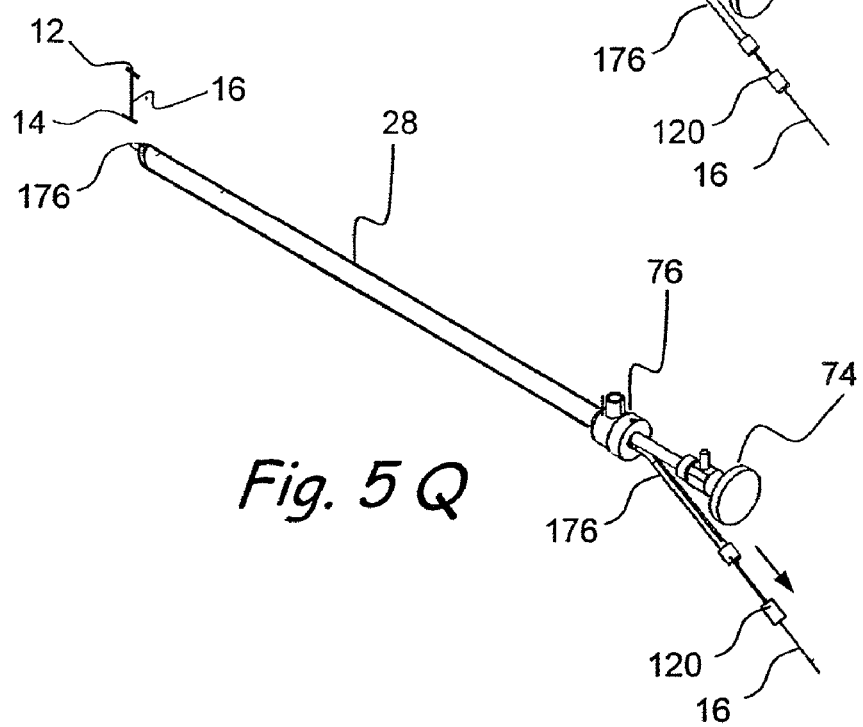
Figure 5:
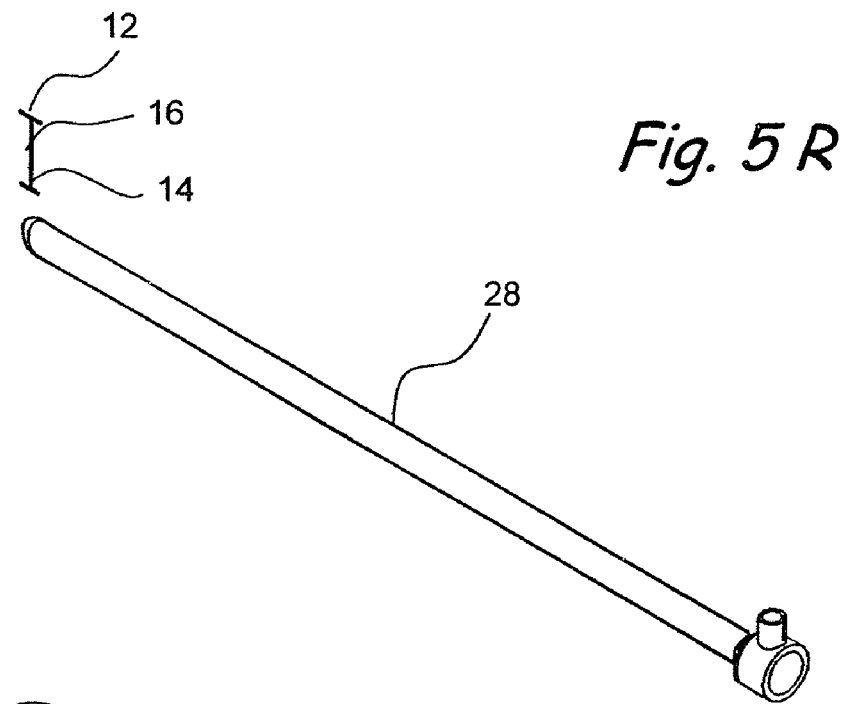
Figure 5:
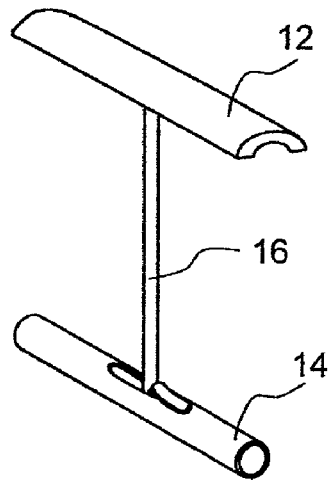
Figure 5:
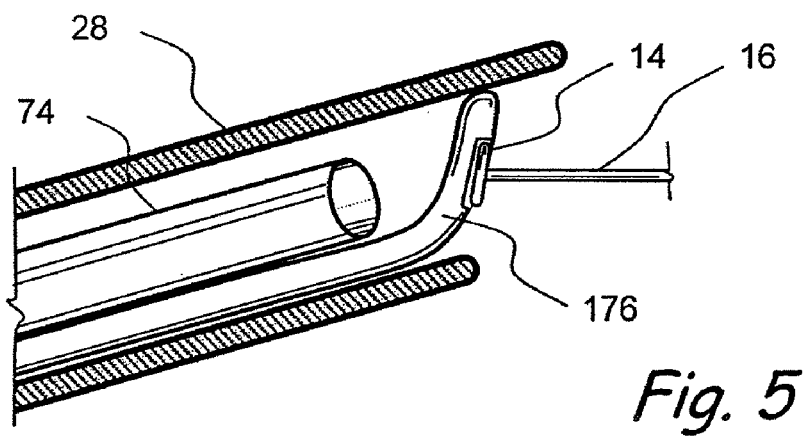
Figure 5:
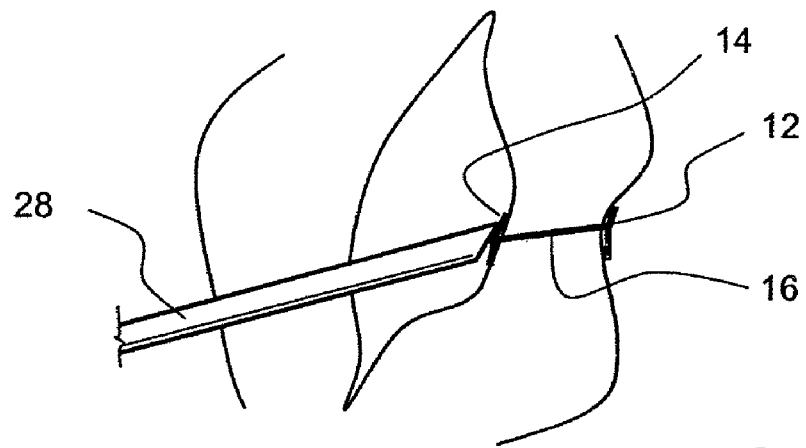
Figure 5:
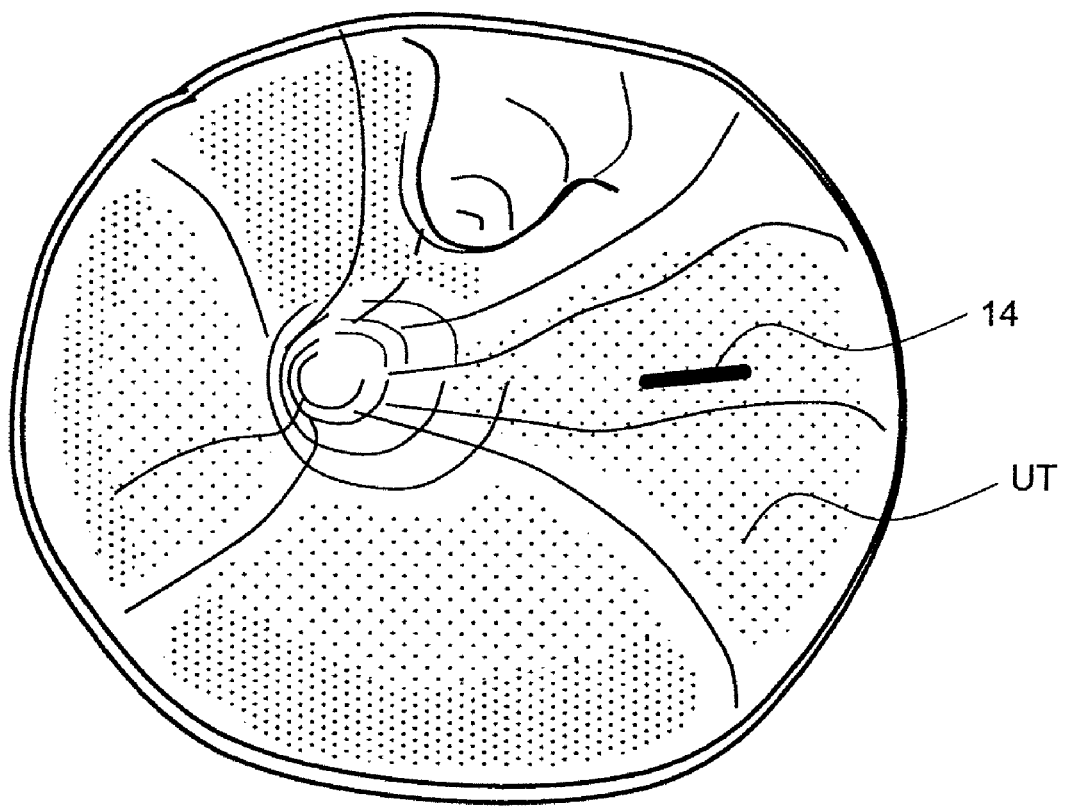

FIG. 5N shows a side view of a second embodiment of a proximal anchor delivery device 34. Proximal anchor delivery device 34 comprises an endoscope introducing tube 48. The proximal end of endoscope introducing tube 48 may comprise an endoscope hub 50 to lock an endoscope 74 to endoscope introducing tube 48. Endoscope introducing tube 48 encloses a lumen through which a suitable endoscope 74 may be introduced into the anatomy. Proximal anchor delivery device 34 comprises an anchor tube 176. The distal end of the anchor tube 176 comprises first anchor tube opening 194 and second anchor tube opening 196 such as shown in FIG. 5B. The lumen of anchor tube 176 encloses a proximal anchor 14 held by an actuator 120. Actuator 120 is used to deploy proximal anchor 14 out of the distal region of anchor tube 176 and into the anatomy by a method similar to the method shown in FIGS. 5B-5D. Deployment of proximal anchor 14 in the anatomy is visualized by an endoscope 74 that is introduced through endoscope introducing tube 48 such that the distal end of anchor tube 176 is located near the distal end of endoscope 74. The distal end of anchor tube 176 may comprise a curved, bent or tapered region. Anchor tube 176 is attached to endoscope introducing tube 48 by a coupling element 76. Proximal anchor delivery device 34 may be introduced into the anatomy through a suitable sheath. Such as sheath may comprise a flushing or aspiration port. The flushing or aspiration port may be in fluid communication with the lumen of the sheath to allow a user to introduce fluids into or remove fluids from an anatomical region.

The embodiment of proximal anchor delivery device 34 shown in FIG. 5N may be used to introduce a proximal anchor 14 over a connector 16 into the anatomy. Proximal anchor 14 is attached to connector 16 and the excess length of connector is trimmed. For example, FIGS. 5O through 5S show the steps of an embodiment of a method of deploying an anchor in an anatomical region using proximal anchor delivery device 34 of FIG. 5N. In the step shown in FIG. 5O, a distal anchor 12 attached to a connector 16 has been anchored in the anatomy. In one method embodiment, distal anchor 12 is anchored transurethrally near the prostate gland capsule by the method shown in FIGS. 3M through 3T. In this embodiment, distal anchor 12 is anchored by one or more devices inserted through a sheath 28 inserted in the urethra. After performing this step, the one or more devices are removed leaving sheath 28 in the urethra.

In the step shown in FIG. 5P, connector 16 is inserted into an opening in the distal region of anchor tube 176. Connector 16 is passed through proximal anchor 14 enclosed by anchor tube 176. Connector 16 is removed from the proximal region of anchor tube 176. Proximal anchor delivery device 34 is inserted in sheath 28 over connector 16 such that the distal end of anchor tube 176 emerges out of the distal end of sheath 28.

In the step shown in FIG. 5Q, proximal anchor 14 is attached to connector 16. Also, the excess length of connector 16 is trimmed. This may be done for example, by a mechanism similar to the mechanism shown in FIGS. 5B through 5D. Thus, proximal anchor 14 is released from anchor tube 168 and is deployed in the anatomy as shown in FIG. 5Q. In one method embodiment, proximal anchor 14 is deployed in the region of the urethra enclosed by the prostate gland.

In the step shown in FIG. 5R, proximal anchor delivery device 34 and endoscope 74 are removed from sheath 28.

In the step shown in FIG. 5S, sheath 28 is removed from the anatomy leaving behind proximal anchor 14 and distal anchor 12 connected by connector 16.

The distal ends of the various proximal anchor delivery devices 34 may be bent, curved, angled, or shaped to deliver a proximal anchor 14 at an angle to the axis of proximal anchor delivery device 34. For example, FIG. 5T shows the distal end of an embodiment of a proximal anchor delivery device comprising an anchor tube with a bent, curved or angled distal end. Proximal anchor delivery device 34 in FIG. 5T is introduced in the anatomy through a sheath 28. Proximal anchor delivery device 34 comprises anchor tube 176 with a bent, curved or angled distal end. The bent, curved or angled distal end of anchor tube 176 enables a user to deploy a proximal anchor 14 in the anatomy at an angle to the axis of proximal anchor delivery device 34.

FIG. 5U shows the step of deploying a proximal anchor in an anatomical region by the proximal anchor delivery device of FIG. 5T. In the step shown in FIG. 5U, proximal anchor 14 is being deployed in the anatomy at an angle to the axis of proximal anchor delivery device 34.

The various mechanisms of deploying proximal or distal anchor disclosed herein may be used to design various embodiments of proximal and distal anchor delivery devices. For example, mechanisms of deploying a distal anchor similar to the mechanism shown in FIGS. 3D through 3K may be used to design several embodiments of distal anchor deploying devices. Similarly, mechanisms of deploying a proximal anchor similar to the mechanism shown in FIGS. 5B through 5D may be used to design several embodiments of proximal anchor deploying devices.

Pre-Clinical Testing:

Pre-clinical testing of an embodiment of a method of compressing a region of the prostate gland was done to evaluate the safety aspects of the method. The devices shown in FIGS. 3A and 5A were used to deploy the retractor 10 shown in FIG. 1C in the prostate gland of the dogs. Six mongrel dogs of 27 to 35 kg underwent a transurethral procedure for luminal restoration of the urethral region enclosed by the prostate gland. In each animal a single retractor 10 was deployed. All procedures were successful with no adverse events. The total procedure time from the time sheath 28 was introduced transurethrally until the time the sheath 28 was removed ranged from 27 to 55 minutes. All the animals were followed up cystoscopically. Typical acute results are shown in FIG. 5V. FIG. 5V shows a cystoscopic view of a region of canine urethra enclosed by the prostate gland that has been treated by a procedure similar to the procedure shown in FIGS. 1D through 1J. FIG. 5V shows a proximal anchor 14 of a retractor 10 shown in FIG. 1C. Retractor 10 is used to compress a region of the prostate gland.

Figure 6:
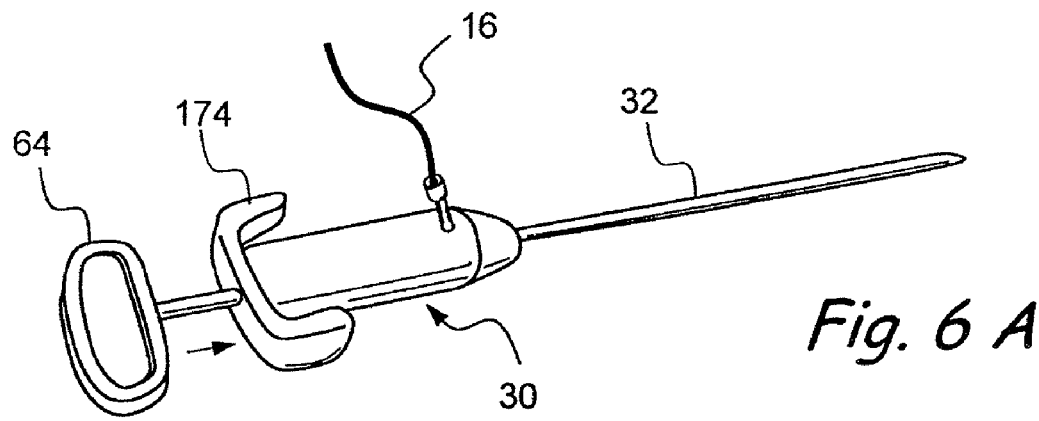
FIG. 6A shows a side view of an embodiment of a distal anchor delivery device.
FIG. 6B shows an enlarged view of the distal region of the distal anchor delivery device of FIG. 6A showing the step of deploying a distal anchor by the distal anchor delivery device.
FIG. 6C shows a side view of an embodiment of a proximal anchor delivery device.
FIG. 6D shows an enlarged view of the distal region of the proximal anchor delivery device of FIG. 6C.
FIG. 6E shows the distal region of an embodiment of a proximal anchor delivery device comprising a curved penetrating distal tip.
FIG. 6F shows an embodiment of a retractor comprising a proximal anchor buried within an anatomical tissue by the proximal anchor delivery device of FIG. 6E.
FIG. 6G shows the distal region of an embodiment of a proximal anchor delivery device comprising a straight penetrating distal tip.
FIG. 6H shows an embodiment of a retractor comprising a proximal anchor buried within an anatomical tissue by the proximal anchor delivery device of FIG. 6G.
FIG. 6I shows a section through the distal tip of a first embodiment of a combined device that can deliver a distal anchor connected to a proximal anchor by a connector.
FIG. 6J shows a side view of a second embodiment of a combined device that can deliver a distal anchor and a proximal anchor connected to each other by a connector.
FIG. 6K shows another view of the embodiment of the combined device shown in FIG. 6J that can deliver a distal anchor and a proximal anchor connected to each other by a connector.
FIGS. 6L through 6Q show the steps of a method of compressing an anatomical tissue by a combined device that delivers a proximal anchor and a distal anchor in the anatomy.
FIGS. 6R through 6W show the distal region of an embodiment of a combined device showing the steps of a method of delivering a retractor comprising a proximal anchor and a distal anchor, wherein the distal anchor is delivered through the proximal anchor.
Figure 6:
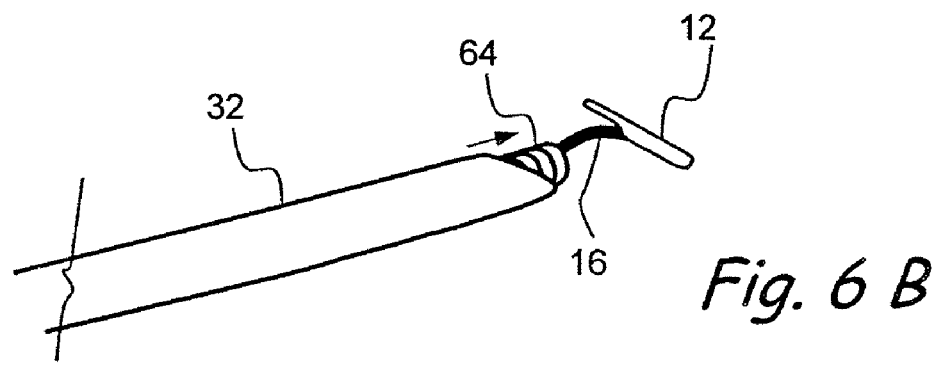
Figure 6:
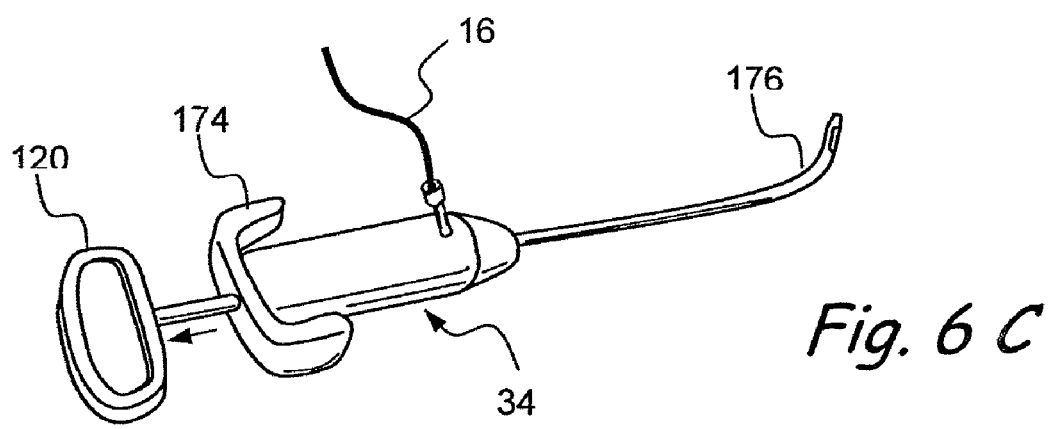
Figure 6:
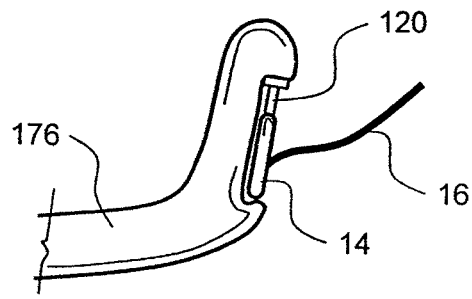
Figure 6:
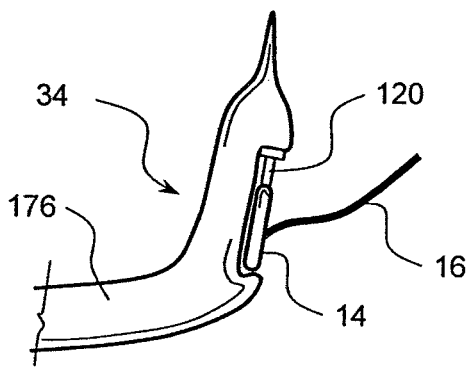
Figure 6:
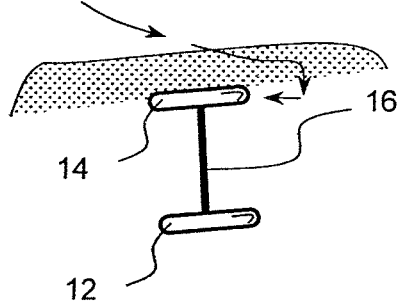
Figure 6:
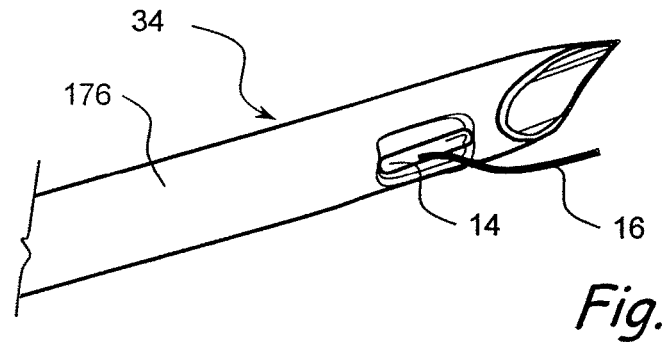
Figure 6:
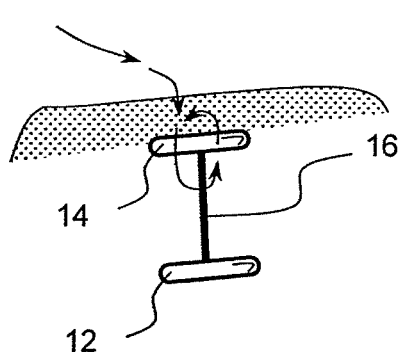
Figure 6:
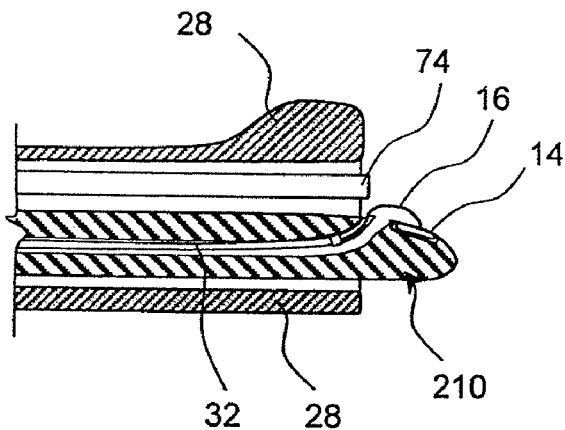
Figure 6:
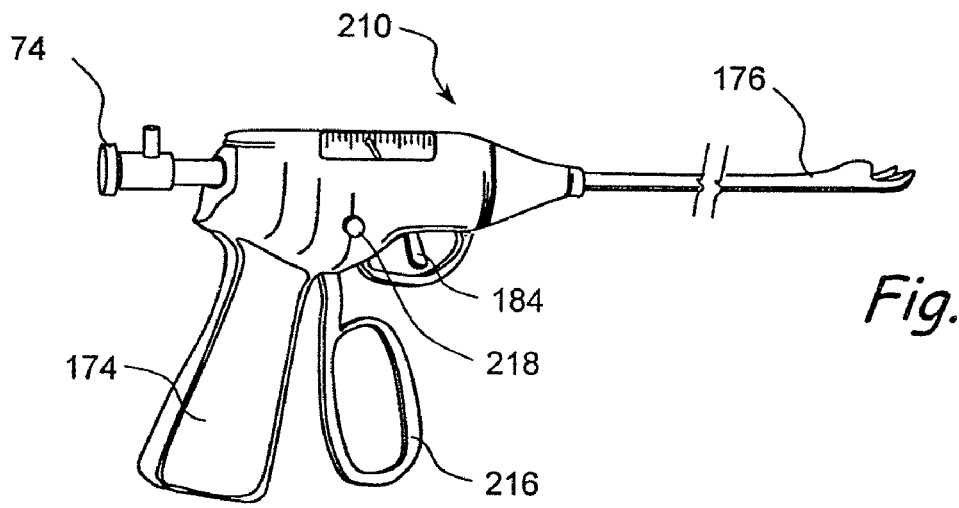
Figure 6:
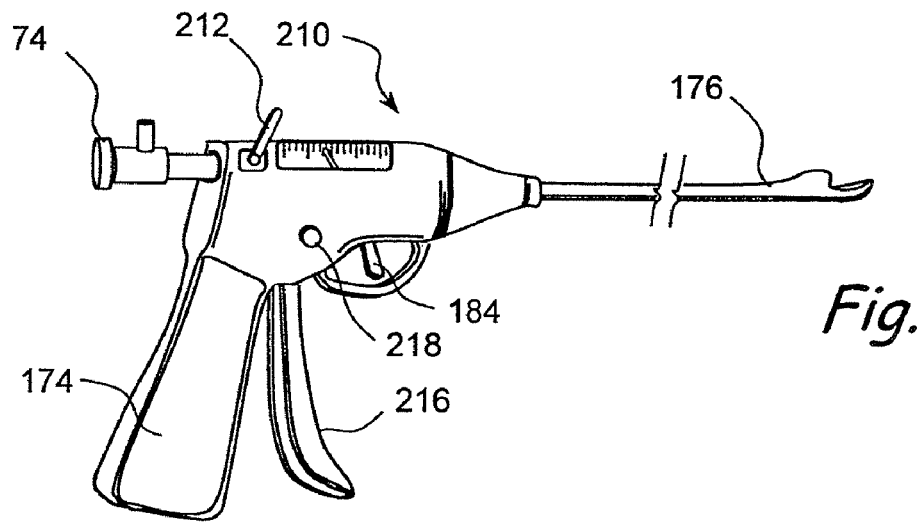
Figure 6:
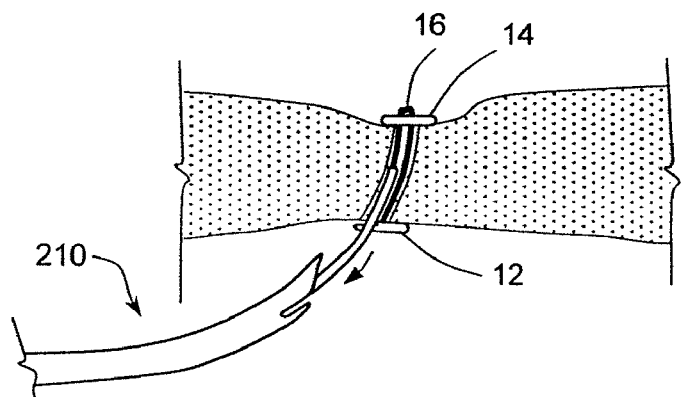
Figure 6:
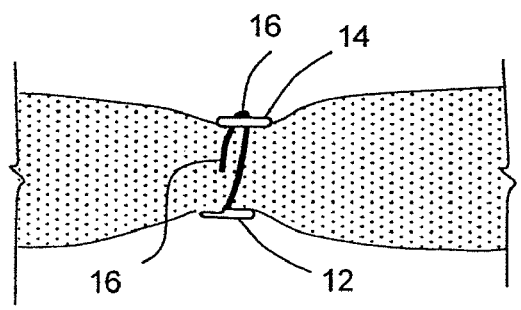
Figure 6:
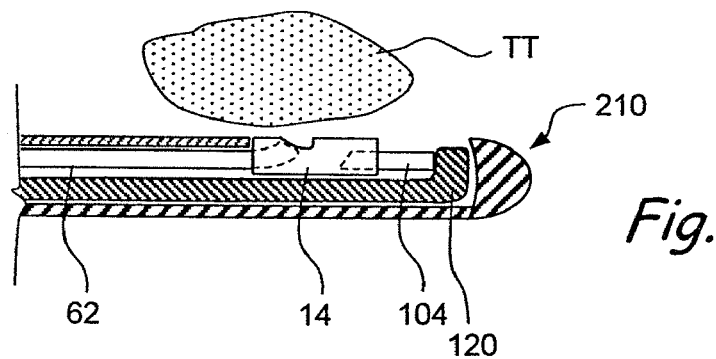
Figure 6:
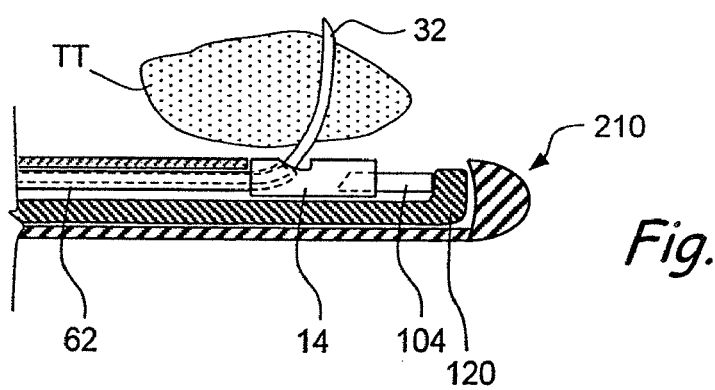
Figure 6:
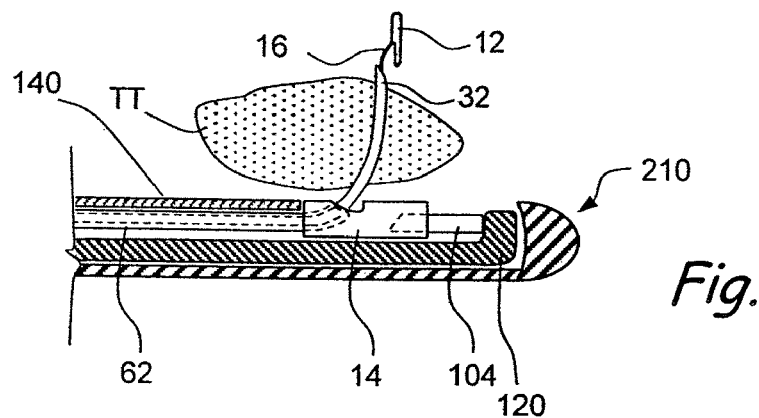
Figure 6:
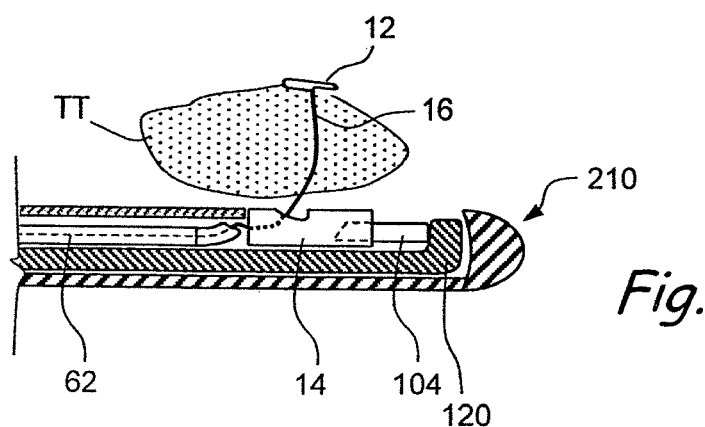
Figure 6:
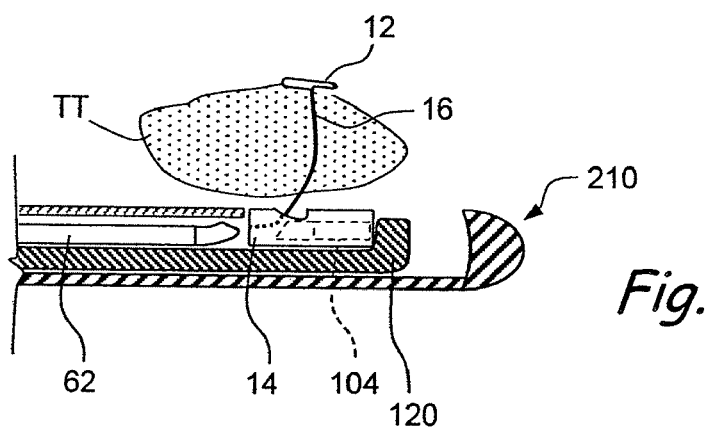
Figure 6:
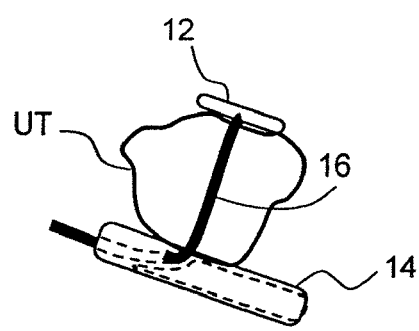

FIG. 6A shows a side view of an embodiment of a distal anchor delivery device. In the embodiment shown in FIG. 6A, distal anchor delivery device 30 comprises an elongate puncturing element e.g. a needle 32 that comprises a lumen. The proximal end of needle 32 is connected to a handle 174. In the embodiment shown in FIG. 6A, handle 174 comprises a curved handpiece that can be gripped by a user with one hand. An elongate pusher 64 slides through the lumen of needle 32. The proximal end of pusher 64 may be enlarged to allow the user to push pusher 64 with the other hand. When pusher 64 is pushed by the user, a distal anchor 12 attached to a connector 16 is pushed out of the distal end of needle 32.

FIG. 6B shows an enlarged view of the distal region of the distal anchor delivery device of FIG. 6A showing the step of deploying a distal anchor by the distal anchor delivery device. In one method embodiment of deploying a distal anchor 12, distal anchor delivery device 30 is pushed into the anatomy until the distal tip of needle 32 is in a desired location. Pusher 64 is pushed by a user. This causes the distal tip of pusher 64 to push a distal anchor 12 attached to a connector 16 out of the distal end of needle 32. Distal anchor delivery device 30 is removed from the anatomy by sliding distal anchor delivery device 30 over connector 16. A desired tension may be generated in connector 16 and a proximal anchor 14 attached to connector 16 to hold and/or compress an anatomical region between proximal anchor 14 and distal anchor 12.

FIG. 6C shows a side view of an embodiment of a proximal anchor delivery device. The embodiment of proximal anchor delivery device 34 shown in FIG. 6C may be used to generate a desired tension in connector 16 and attach a proximal anchor 14 to connector 16 after the step shown in FIG. 6B. In the embodiment shown in FIG. 6C, proximal anchor delivery device 34 comprises an elongate anchor tube 176 that comprises a lumen. In the embodiment shown, the distal tip of anchor tube 176 comprises a bent, curved or angled region. The proximal end of anchor tube 176 is connected to a handle 174. In the embodiment shown in FIG. 6C, handle 174 comprises a curved handpiece that can be gripped by a user with one hand. An elongate actuator 120 slides through the lumen of anchor tube 176. The proximal end of actuator 120 may be enlarged to allow the user to pull actuator 120 with the other hand. When actuator 120 is pulled by the user, a proximal anchor 14 is attached to a connector 16. Also, when actuator 120 is pulled by the user, the excess length of connector 16 may be cut or trimmed by a mechanism similar to the mechanism shown in FIGS. 5B through 5D.

FIG. 6D shows an enlarged view of the distal region of the proximal anchor delivery device of FIG. 6C. In one embodiment of a method of deploying a proximal anchor 14, proximal anchor delivery device 34 of FIG. 6C is inserted in the anatomy over connector 16. This is done such that connector 16 passes through a proximal anchor 14 located in anchor tube 176. Proximal anchor delivery device 34 is advanced in the anatomy until the distal tip of anchor tube 176 is in a desired location. Connector 16 is pulled by a user to introduce a desired tension in connector 16. Actuator 120 is pulled by a user. This attaches proximal anchor 14 to connector 16 by a mechanism similar to the mechanism shown in FIGS. 5B through 5D. Also, the excess length of connector 16 may be cut or trimmed by a mechanism similar to the mechanism shown in FIGS. 5B through 5D. Distal anchor delivery device 30 is removed from the anatomy. This step leaves behind proximal anchor 14 and distal anchor 12 connected to each other by connector 16.

The anchor delivery devices disclosed herein may be used to bury an anchor within an anatomical tissue. For example, FIG. 6E shows the distal region of an embodiment of a proximal anchor delivery device comprising a curved penetrating distal tip. In the embodiment shown in FIG. 6E, proximal anchor delivery device 34 comprises an anchor tube 176 with a curved penetrating distal tip. The penetrating distal tip is used to penetrate an anatomical tissue. A proximal anchor 14 is deployed within the anatomical tissue, thereby burying proximal anchor 14 within the anatomical tissue.

FIG. 6F shows an embodiment of a retractor comprising a proximal anchor buried within an anatomical tissue by the proximal anchor delivery device of FIG. 6E. In one method embodiment, a distal anchor 12 attached to a connector 16 is deployed in the anatomy. Proximal anchor delivery device 34 is inserted in the anatomy over connector 16. This is done such that connector 16 passes through a proximal anchor 14 located in anchor tube 176. Proximal anchor delivery device 34 is advanced in the anatomy such that the curved distal tip of anchor tube 176 tangentially penetrates a wall of an anatomical tissue. Proximal anchor delivery device 34 is advanced until the curved distal tip of anchor tube 176 is in a desired location. Connector 16 is pulled by a user to introduce a desired tension in connector 16. Proximal anchor 14 is attached to connector 16. This may be done by a mechanism on proximal anchor delivery device 34 similar to the mechanism shown in FIGS. 5B through 5D. Also, the excess length of connector 16 may be cut or trimmed. This may be done by a mechanism on proximal anchor delivery device 34 similar to the mechanism shown in FIGS. 5B through 5D. Distal anchor delivery device 30 is removed from the anatomy. This step leaves behind proximal anchor 14 buried within the anatomical tissue connected to distal anchor 12 by connector 16.

FIG. 6G shows the distal region of an embodiment of a proximal anchor delivery device comprising a straight penetrating distal tip. In the embodiment shown in FIG. 6G, proximal anchor delivery device 34 comprises an anchor tube 176 with a straight penetrating distal tip. The penetrating tip is used to penetrate an anatomical tissue. A proximal anchor 14 is deployed within the anatomical tissue, thereby burying proximal anchor 14 within the anatomical tissue.

FIG. 6H shows an embodiment of a retractor comprising a proximal anchor buried within an anatomical tissue by the proximal anchor delivery device of FIG. 6G. In one method embodiment, a distal anchor 12 attached to a connector 16 is deployed in the anatomy. Proximal anchor delivery device 34 is inserted in the anatomy over connector 16. This is done such that connector 16 passes through a proximal anchor 14 located in anchor tube 176. Proximal anchor delivery device 34 is advanced in the anatomy such that the straight distal tip of anchor tube 176 penetrates a wall of an anatomical tissue roughly perpendicular to the wall of an anatomical tissue. Proximal anchor delivery device 34 is advanced until the straight distal tip of anchor tube 176 is in a desired location. Connector 16 is pulled by a user to introduce a desired tension in connector 16. Proximal anchor 14 is attached to connector 16. This may be done by a mechanism on proximal anchor delivery device 34 similar to the mechanism shown in FIGS. 5B through 5D. Also, the excess length of connector 16 may be cut or trimmed. This may be done by a mechanism on proximal anchor delivery device 34 similar to the mechanism shown in FIGS. 5B through 5D. Distal anchor delivery device 30 is removed from the anatomy. This step leaves behind proximal anchor 14 buried within the anatomical tissue connected to distal anchor 12 by connector 16. The tension in connector 16 may cause proximal anchor 14 to flip and orient perpendicularly to connector 16.

Various embodiments of distal anchor delivery device 30 and various embodiments of proximal anchor delivery device 34 may be combined into a single device that delivers both distal anchor 12 and proximal anchor 14. For example, FIG. 6I shows a section through the distal tip of a first embodiment of a combined device that can deliver a distal anchor connected to a proximal anchor by a connector. In FIG. 6I, a combined device 210 is introduced in the anatomy through an elongate sheath 28. The distal tip of combined device 210 comprises an arrangement to hold a proximal anchor 14. Proximal anchor 14 may be controllably delivered from combined device 210 by a user into the anatomy by a releasing mechanism. Proximal anchor 14 is connected to a connector 16. Connector 16 is further connected to a distal anchor 12. Distal anchor 12 is attached to a distal region of combined device 210 by an arrangement to hold distal anchor 12. Distal anchor 12 may be controllably delivered from combined device 210 by the user into the anatomy by a releasing mechanism. The step of delivering proximal anchor 14 and/or the step of delivering distal anchor 12 may be visualized by an endoscope 74.

FIG. 6J shows a side view of a second embodiment of a combined device that can deliver a distal anchor and a proximal anchor connected to each other by a connector. In FIG. 6J, combined device 210 comprises an elongate anchor tube 176 through which proximal anchor 14 and distal anchor 12 are delivered. Combined device 210 further comprises an arrangement for introducing an endoscope 74. The step of delivering proximal anchor 14 and/or the step of delivering distal anchor 12 may be visualized by endoscope 74. Combined device 210 further comprises a handle 174 to enable a user to hold combined device 210. Proximal anchor 14 and distal anchor 12 are delivered in the anatomy by moving an anchor delivery trigger 216 connected to handle 174. In a distal anchor delivery mode, anchor delivery trigger 216 is used to deliver distal anchor 12. In a proximal anchor delivery mode, anchor delivery trigger 216 is used to deliver proximal anchor 14. In one embodiment, movement of anchor delivery trigger 216 causes movement of a needle in the distal anchor delivery mode. A distal anchor 12 is delivered through the needle in the anatomy. In one embodiment, movement of anchor delivery trigger 216 locks a proximal anchor 14 connector 106. Also, movement of anchor delivery trigger 216 cuts excess length of a connector 16 attached to proximal anchor 14. This delivers proximal anchor 14 in the anatomy. Anchor delivery trigger 216 is switched between distal anchor delivery mode and proximal anchor delivery mode by a mode selecting switch 218.

FIG. 6K shows a side view of a third embodiment of a combined device that can deliver a distal anchor and a proximal anchor connected to each other by a connector. In this embodiment, combined device 210 further comprises a deflecting lever 212 that can be used to controllably bend or deflect the distal region of combined device 210.

In one method embodiment, a combined device is used to deliver a first anchor to a region distal to a tissue and deliver a second anchor to a region proximal to the tissue. In another method embodiment, a combined device is used to deliver a first anchor to a region proximal to a tissue and deliver a second anchor to a region distal to the tissue. For example, FIGS. 6L through 6Q show the steps of a method of compressing an anatomical tissue by a combined device that delivers proximal anchor 14 and distal anchor 12 in the anatomy. In the step shown in FIG. 6L, a combined device 210 is introduced in the anatomy. Combined device 210 comprises a sharp distal end to penetrate anatomical tissue. Combined device 210 is advanced through the anatomy until the distal tip of combined device 210 is located in a desired location proximal to a tissue. Distal anchor 12 is delivered by combined device 210 to the desired location proximal to a tissue. In the step shown in FIG. 6M, combined device 210 is advanced such that the sharp distal tip of combined device 210 penetrates through the tissue. Combined device 210 is advanced through the tissue until the distal tip of combined device 210 is located in a desired location distal to the tissue. In the step shown in FIG. 6N, a proximal anchor 14 is delivered by combined device 210 to the desired location distal to the tissue. Proximal anchor 14 is connected to distal anchor 12 by a connector 16 that is attached to distal anchor 12 and passes through proximal anchor 14. Proximal anchor 14 comprises a unidirectional mechanism to allow the motion of connector 16 through proximal anchor 14 only in one direction. The unidirectional mechanism prevents the motion of connector 16 through proximal anchor 14 in the opposite direction. In the step shown in FIG. 6O, combined device 210 is pulled in the proximal direction to partially withdraw combined device 210 from the tissue. In the step shown in FIG. 6P, connector 16 is pulled with a sufficient force to move connector 16 through proximal anchor 14. This step pulls distal anchor 12 towards proximal anchor 14 thereby compressing the tissue between proximal anchor 14 and distal anchor 12. In the step shown in FIG. 6Q, connector 16 is cut. This step may be performed by a cutting mechanism in combined device 210 or by a separate cutter device disclosed elsewhere in this patent application or in the documents incorporated herein by reference. After connector 16 is cut, the unidirectional mechanism on proximal anchor 14 prevents motion of connector 16 through proximal anchor 14. This in turn maintains the tension in connector 16 between proximal anchor 14 and distal anchor 12.

FIGS. 6R through 6W show the distal region of an embodiment of a combined device showing the steps of a method of delivering a retractor comprising a proximal anchor and a distal anchor, wherein the distal anchor is delivered through the proximal anchor. In the step shown in FIG. 6R, a combined device 210 is introduced in the anatomy. In one method embodiment, combined device 210 is inserted trans-urethrally into the region of the urethra enclosed by the prostate gland. In other alternate method embodiments, combined device 210 may be introduced into anatomical regions including, but not limited to large intestines, stomach, esophagus, trachea, a bronchus, bronchial passageways, veins, arteries, lymph vessels, a ureter, bladder, cardiac atria or ventricles, etc. In the embodiment shown in FIG. 6R, the distal region of combined device 210 encloses an elongate actuator 120. A surface of actuator 120 can be used to drive a lock pin 104 into a proximal anchor 14. The movement of proximal anchor 14 along the proximal direction is restricted by a stopper 140. A needle 32 passes through proximal anchor 14. In the embodiment shown in FIG. 6R, needle 32 enters proximal anchor 14 through the proximal end of proximal anchor 14. Needle 32 exits proximal anchor 14 through a side opening in proximal anchor 14. In the step shown in FIG. 6S, needle 32 is advanced through proximal anchor 14 such that the distal tip of needle 32 exits combined device 210. Needle 32 is advanced further such that needle 32 penetrates through a target tissue TT. In the step shown in FIG. 6T, a distal anchor 12 is delivered through needle 32. Distal anchor 12 is connected to a connector 16 that passes through needle 32. In the step shown in FIG. 6U, needle 32 is withdrawn from combined device 210. This step leaves behind distal anchor 12 connected to connector 16. Connector 16 is pulled in the proximal direction. This step orients distal anchor 12 perpendicular to connector 16. Also, this step causes a region of the target tissue to be compressed between combined device 210 and distal anchor 12. In the step shown in FIG. 6V, actuator 120 is pulled in the proximal direction by a user. This causes actuator 120 to drive lock pin 104 into proximal anchor 14. Lock pin 104 compresses a region of connector 16 between a surface of proximal anchor 14 and lock pin 104. This locks proximal anchor 14 to connector 16. Combined device 210 may further comprise a mechanism to cut or trim the excess length of connector 16. In one embodiment, the mechanism is similar to the cutting mechanism shown in FIGS. 5B-5D. In the step shown in FIG. 6W, combined device 210 is withdrawn from the anatomy. This step leaves behind retractor 10 comprising distal anchor 12 connected to proximal anchor 14 by connector 16.

The various devices and methods disclosed herein or modifications thereof may be used to retract, lift, support, reposition or compress a region of a tubular anatomical organ such as the urethra. Such methods may also be used, for example, to reduce the cross sectional area of the lumen of a tubular anatomical organ. For example, the various devices and methods disclosed herein or modifications thereof may be used to reduce the cross sectional area of the lumen of the urethra to treat incontinence, especially urinary stress incontinence. This may be done by various devices that may be introduced in the urethra through a variety of approaches. Some examples of such approaches include, but are not limited to transurethral approach, transvaginal approach, transperineal approach, etc.

FIGS. 7A through 7H show a longitudinal section of a tubular organ showing the steps of a method of reducing the cross sectional area of the lumen of the tubular organ. In the step shown in FIG. 7A, an elongate distal anchor delivery device 30 is introduced in the tubular organ such as the urethra. In one particular embodiment, distal anchor delivery device 30 is introduced transurethrally into the urethra. A needle 32 is introduced through distal anchor delivery device 30. The distal region of needle 32 may comprise a curved region. Needle 32 may exit distal anchor delivery device 30 at an exit angle ranging from 0 degrees to 180 degrees to the axis of distal anchor delivery device 30. Needle 32 is advanced through the tubular organ such that needle 32 penetrates through a wall of the tubular organ. In the step shown in FIG. 7B, distal anchor delivery device 30 is rotated. This causes needle 32 to pull the tissue surrounding the wall of the tubular organ along the direction of rotation of distal anchor delivery device 30. In the step shown in FIG. 7C, distal anchor delivery device 30 is rotated further. This causes a region of the tissue surrounding the tubular organ to fold around the tubular organ as shown in FIG. 7C. In the step shown in FIG. 7D, a distal anchor 12 is delivered in the anatomy through needle 32. In the step shown in FIG. 7E, needle 32 is withdrawn from the anatomy through distal anchor delivery device 30. As shown in FIG. 7E, distal anchor 12 is attached to an elongate connector 16 that passes through distal anchor delivery device 30. In the step shown in FIG. 7F, distal anchor delivery device 30 is removed from the tubular organ over connector 16. An elongate proximal anchor delivery device 34 is introduced in the tubular organ over connector 16. This is done such that connector 16 passes through a proximal anchor 14 located on proximal anchor delivery device 34. Proximal anchor delivery device 34 is advanced through the tubular organ such that the distal tip of proximal anchor delivery device 34 is located near the site where needle 32 punctured the wall of the tubular organ. In the step shown in FIG. 7G, connector 16 is pulled by a user to introduce a desired tension in connector 16. In the step shown in FIG. 7H, proximal anchor 14 is attached to connector 16. This may be done by a mechanism on proximal anchor delivery device 34 similar to the mechanism shown in FIGS. 5B through 5D. Also, the excess length of connector 16 may be cut or trimmed. This may be done by a mechanism on proximal anchor delivery device 34 similar to the mechanism shown in FIGS. 5B through 5D. Distal anchor delivery device 30 is removed from the anatomy. This step leaves behind proximal anchor 14 connected to distal anchor 12 by connector 16. The tension in connector 16 causes the tissue between proximal anchor 14 and distal anchor 12 to fold as shown in FIG. 7H. This in turn reduces the cross sectional area of the lumen of the tubular organ.

FIG. 7I shows a schematic diagram of a tubular organ showing the configuration of the tubular organ before performing the method shown in FIGS. 7A through 7H. Examples of tubular organs that may be treated by the method shown in FIGS. 7A through 7H include, but are not limited to urethra, bowel, stomach, esophagus, trachea, bronchii, bronchial passageways, veins, arteries, lymphatic vessels, ureters, bladder, cardiac atria or ventricles, uterus, fallopian tubes, etc. FIG. 7J shows a schematic diagram of the tubular organ of FIG. 7I showing a possible configuration obtained after performing the method shown in FIGS. 7A through 7H. In FIG. 7J, the tension in connector 16 causes the tissue between proximal anchor 14 and distal anchor 12 to twist. This in turn reduces the cross sectional area of the lumen of the tubular organ.

The method shown in FIGS. 7A through 7H may also be performed using a distal anchor delivery device comprising a helical needle. For example, FIG. 7K shows an embodiment of a distal anchor delivery device 30 comprising a helical needle 32. In one method embodiment, distal anchor delivery device 30 is inserted into a tubular organ. Helical needle 32 is advanced through distal anchor delivery device 30 such that the distal region on needle 32 emerges out of distal anchor delivery device 30. Needle 32 emerges out of distal anchor delivery device 30 and penetrates the wall of the tubular organ. In one embodiment, the tubular organ is the urethra UT comprising a urethral wall UW. The helical shape of needle 32 causes at least a portion of helical needle 32 to curve around the lumen of the tubular organ. Also, the helical shape of needle 32 causes the distal tip of needle 32 to be axially spaced apart from the site where needle 32 penetrates into the wall of the tubular organ. A distal anchor 12 may be delivered into the anatomy from the distal tip of needle 32. Thus, distal anchor 12 may be delivered at a location that is axially spaced apart from the penetration site of needle 32. A proximal anchor 14 may be attached to connector 16 by a method similar to the method shown in FIGS. 7F-7H.

Figures 7L, 7M, 7N:
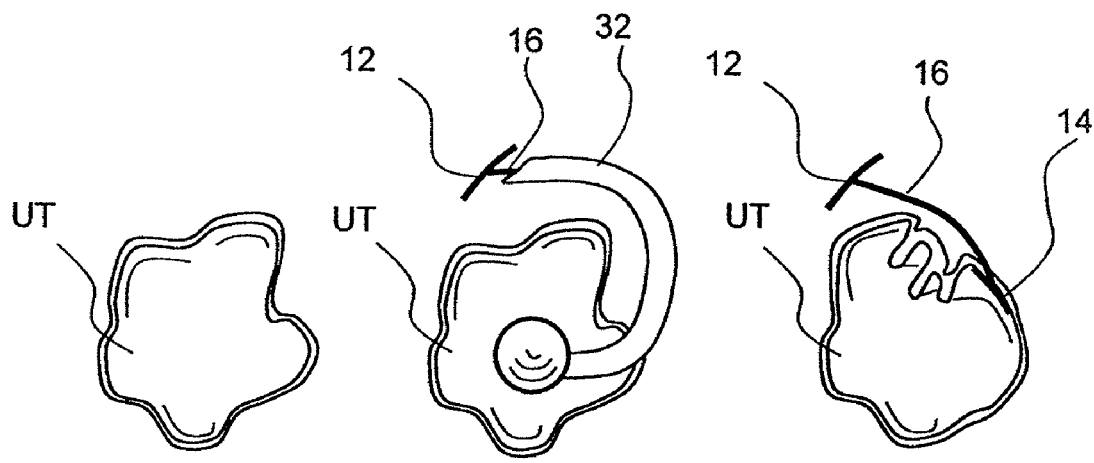
FIGS. 7L through 7N show a cross section of a tubular organ showing the steps of a method of reducing the cross sectional area of the lumen of the tubular organ by creating one or more folds or pleats in the walls of the tubular organ along the circumference of the lumen.

FIGS. 7L through 7N show a cross section of a tubular organ showing the steps of a method of reducing the cross sectional area of the lumen of the tubular organ by creating one or more folds or pleats in the walls of the tubular organ along the circumference of the lumen. FIG. 7L shows a cross section of a tubular organ. Examples of tubular organs that may be treated by the method shown in FIGS. 7L through 7N include, but are not limited to urethra UT, bowel, stomach, esophagus, trachea, bronchii, bronchial passageways, veins, arteries, lymphatic vessels, ureters, bladder, cardiac atria or ventricles, uterus, fallopian tubes, etc. In the step shown in FIG. 7M, an anchor delivery device comprising a curved needle 32 is introduced in the lumen of the tubular organ. Needle 32 is advanced through the anchor delivery device such that the distal tip of needle 32 penetrates the wall of the tubular organ. Distal anchor 12 is advanced through needle 32 and is delivered through the distal tip of needle 32 into the surrounding tissue. A desired tension is created in connector 16 attached to distal anchor 12. A proximal anchor 14 is attached to a desired location on connector 16 to compress the tissue between proximal anchor 14 and distal anchor 12 as shown in FIG. 7N. This compression creates one or more folds or pleats in the walls of the tubular organ as shown in FIG. 7N. This in turn reduces the cross sectional area of the lumen of the tubular organ. In one embodiment, distal anchor delivery device 30 comprising a curved needle 32 is introduced trans-urethrally in the urethra of a patient suffering from urinary incontinence. Distal anchor 12 is deployed in the tissue surrounding the urethra by distal anchor delivery device 30. Distal anchor delivery device 30 is removed from the urethra. Proximal anchor delivery device 34 is introduced trans-urethrally in the urethra over connector 16. Proximal anchor 14 is attached to connector 16 by proximal anchor delivery device 34 such that proximal anchor 14 is located in the lumen of the urethra. Throughout this document wherever an anchor is said to be placed within a body lumen, it is to be understood that such anchor could be positioned within the lumen itself or at some sub-luminal or peri-luminal location, unless specified otherwise. A suitable tension in connector 16 causes proximal anchor 14 and distal anchor 12 to compress the tissue between them. This compression creates one or more folds or pleats in the walls of the urethra as shown in FIG. 7N. The one or more folds or pleats are preferably created in the region of the urethra adjacent to a urinary sphincter. This enables the urinary sphincter to close more efficiently. This in turn reduces the undesired leakage of urine through the urethra of the patient, thereby reducing the severity of incontinence.

Figures 7O, 7P:
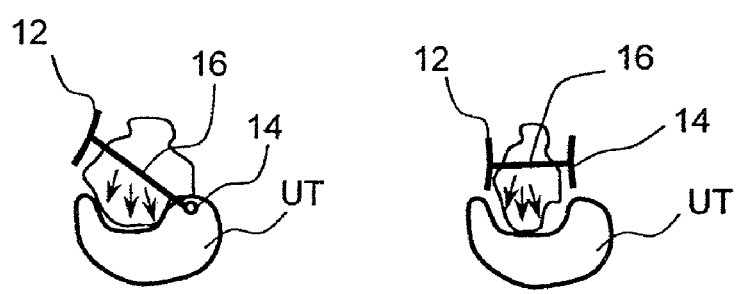
FIG. 7O shows a cross section of a tubular organ showing a first embodiment of a method of compressing a tissue adjacent to a tubular organ to cause one or more regions of the tissue to displace the walls of the tubular organ thereby reducing the cross sectional area of the lumen of the tubular organ.
FIG. 7P shows a cross section of a tubular organ showing a second embodiment of a method of compressing a tissue adjacent to a tubular organ to cause one or more regions of the tissue to displace the walls of the tubular organ thereby reducing the cross sectional area of the lumen of the tubular organ.
Figure 7Q:
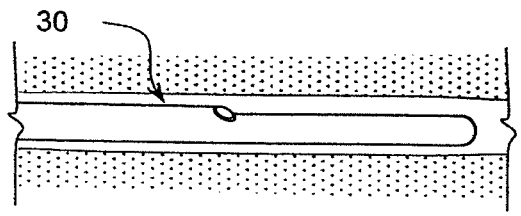
FIGS. 7Q through 7V show longitudinal sections of a tubular organ showing the steps of a method of reducing the cross sectional area of the lumen of the tubular organ by creating one or more folds or bulges in the walls of the tubular organ along the axis of the tubular organ.
Figure 7R:
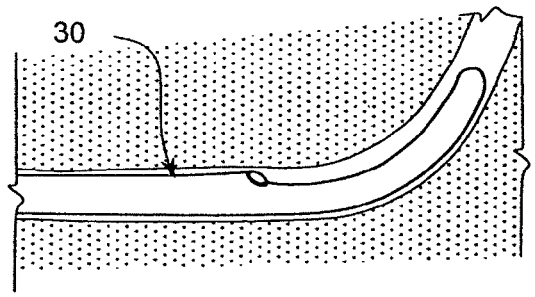

FIG. 7O shows a cross section of a tubular organ showing a first embodiment of a method of compressing a tissue adjacent to a tubular organ to cause one or more regions of the tissue to displace the walls of the tubular organ thereby reducing the cross sectional area of the lumen of the tubular organ. In FIG. 7O, the urethra is used as an example of a tubular organ that may be treated using the method. Other examples of tubular organs that may be treated by the method shown in FIG. 7O include, but are not limited to bowel, stomach, esophagus, trachea, bronchii, bronchial passageways, veins, arteries, lymphatic vessels, ureters, bladder, cardiac atria or ventricles, uterus, fallopian tubes, etc. In the method shown in FIG. 7O, proximal anchor 14 is located in a lumen of a tubular organ. Proximal anchor 14 is connected to one end of a connector 16 that is under a desired tension. The other end of connector 16 is connected to a distal anchor 12. Distal anchor 12 is implanted outside the lumen of the tubular organ. In one embodiment, distal anchor 12 is implanted within a tissue located adjacent to the tubular organ. In another embodiment, distal anchor 12 is implanted beyond a tissue located adjacent to the tubular organ. The tension in connector 16 causes proximal anchor 14 and distal anchor 12 to compress a region of the tissue located adjacent to the tubular organ. This causes one or more regions of the tissue located adjacent to the tubular organ to bulge and displace one or more regions of the wall of the tubular organ. This in turn reduces the cross sectional area of the lumen of the tubular organ.

FIG. 7P shows a cross section of a tubular organ showing a second embodiment of a method of compressing a tissue adjacent to a tubular organ to cause one or more regions of the tissue to displace the walls of the tubular organ thereby reducing the cross sectional area of the lumen of the tubular organ. In FIG. 7P, the urethra is used as an example of a tubular organ that may be treated using the method. Other examples of tubular organs that may be treated by the method shown in FIG. 7P include, but are not limited to bowel, stomach, esophagus, trachea, bronchii, bronchial passageways, veins, arteries, lymphatic vessels, ureters, bladder, cardiac atria or ventricles, uterus, fallopian tubes, etc. In the method shown in FIG. 7P, proximal anchor 14 is located on one side of a tissue located adjacent to the tubular organ. Proximal anchor 14 is connected to one end of a connector 16 that is under a desired tension. The other end of connector 16 is connected to a distal anchor 12. Distal anchor 12 is implanted on the opposite side of the tissue located adjacent to the tubular organ. The tension in connector 16 causes proximal anchor 14 and distal anchor 12 to compress a region of the tissue. This in turn causes one or more regions of the tissue located adjacent to the tubular organ to bulge and displace one or more regions of the wall of the tubular organ as shown in FIG. 7P. This in turn reduces the cross sectional area of the lumen of the tubular organ.

Figure 7S:
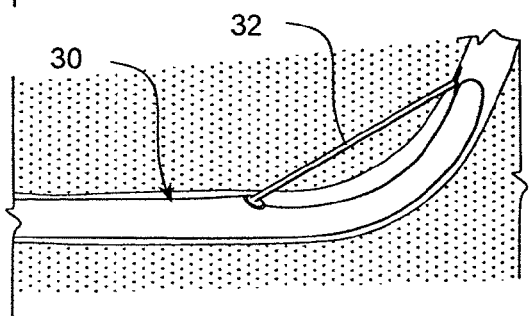
Figure 7T:
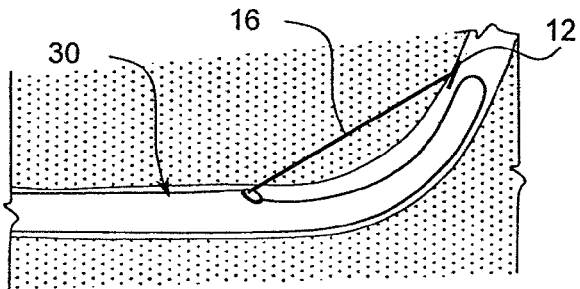
Figure 7U:
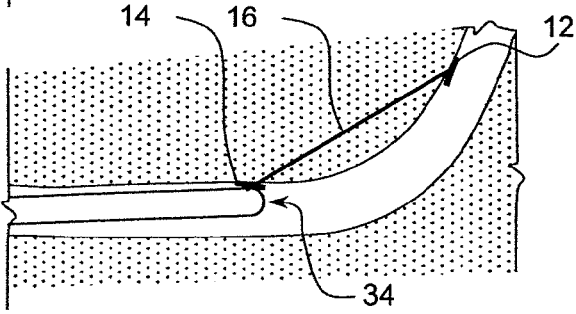
Figure 7V:
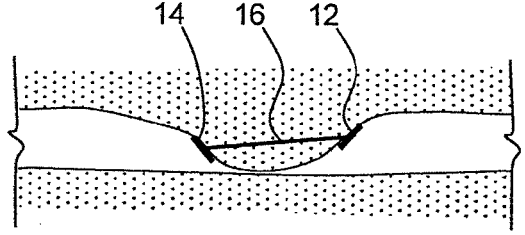

FIGS. 7Q through 7V show longitudinal sections of a tubular organ showing the steps of a method of reducing the cross sectional area of the lumen of the tubular organ by creating one or more folds or bulges in the walls of the tubular organ along the axis of the tubular organ. In the step shown in FIG. 7Q, a distal anchor delivery device 30 is introduced in a tubular organ. In FIGS. 7Q-7V, the urethra is used as an example of a tubular organ that may be treated using the method. Other examples of tubular organs that may be treated by the method shown in FIGS. 7Q to 7V include, but are not limited to bowel, stomach, esophagus, trachea, bronchii, bronchial passageways, veins, arteries, lymphatic vessels, ureters, bladder, cardiac atria or ventricles, uterus, fallopian tubes, etc. Distal anchor delivery device 30 comprises a bendable distal tip. The bendable distal tip can be controllably bent by a user. Distal anchor delivery device 30 is advanced through the tubular organ and positioned in a desired location. In the step shown in FIG. 7R, the distal tip of distal anchor delivery device 30 is controllably bent by the user. In the step shown in FIG. 7S, a needle 32 is advanced through distal anchor delivery device 30. Needle 32 emerges out of distal anchor delivery device 30 at an angle to the axis of distal anchor delivery device 30 as shown in FIG. 7S. Needle 32 is advanced such that it penetrates through a region of the wall of the tubular organ at a penetration site. Needle 32 is further advanced such that it reenters the lumen of the tubular organ. This step may be visualized by an endoscope located in the lumen of the tubular organ. In the step shown in FIG. 7T, a distal anchor 12 is deployed through the distal tip of needle 32. Distal anchor delivery device 30 is withdrawn from the tubular organ leaving distal anchor 12 connected to a connector 16. In the step shown in FIG. 7U, a proximal anchor delivery device 34 is advanced over connector 16. Proximal anchor delivery device 34 is advanced until the distal region of proximal anchor delivery device 34 is adjacent to the penetration site of needle 32. Connector 16 is pulled to create a desired tension in connector 16. Proximal anchor 14 is attached to connector 16 in the lumen of the tubular organ. The tension in connector 16 causes proximal anchor 14 and distal anchor 12 to compress the region of the wall of the tubular organ located between proximal anchor 14 and distal anchor 12. This in turn causes one or more regions of the wall of the tubular organ to fold or bulge into the lumen of the tubular organ as shown in FIG. 7V. This in turn creates one or more folds or bulges in the walls of the tubular organ along the axis of the tubular organ. The one or more folds or bulges reduce the cross sectional area of the lumen of the tubular organ. This method can be repeated to compress multiple regions of the wall of the tubular organ to create multiple bulges in the wall of the tubular organ. In one method embodiment, the one or more folds or bulges are preferably created in the region of the urethra adjacent to a urinary sphincter of a patient suffering from incontinence. This enables the urinary sphincter to close more efficiently. This in turn reduces the undesired leakage of urine through the urethra of the patient, thereby reducing the severity of incontinence.

FIGS. 7W through 7Y shows cross sections of a tubular organ showing the steps of a first embodiment of a method of reducing the cross sectional area of the lumen of the tubular organ by implanting a device that pinches the walls of the tubular organ to create a recess. In FIGS. 7W-7Y, the urethra is used as an example of a tubular organ that may be treated using this method. Other examples of tubular organs that may be treated by the method shown in FIGS. 7W-7Y include, but are not limited to urethra, blood vessels, bowel, stomach, esophagus, trachea, bronchii, bronchial passageways, veins, arteries, lymphatic vessels, ureters, bladder, cardiac atria or ventricles, uterus, fallopian tubes, etc. A distal anchor delivery device is introduced in the anatomy. The distal anchor delivery device is used to penetrate through the lumen of a tubular organ and deploy a distal anchor 12 in the walls of the tubular organ or in the surrounding anatomy as shown in FIG. 7W. Distal anchor 12 is connected to a connector 16 that passes through the lumen of the tubular organ. In the step shown in FIG. 7X, a proximal anchor 14 is advanced over connector 16. Proximal anchor 14 is advanced over connector 16 such that proximal anchor 14 is proximal to the lumen of the tubular organ. Proximal anchor 14 may be located in the walls of the tubular organ or in the surrounding anatomy. Connector 16 is pulled to create a desired tension in connector 16. The tension in connector 16 causes proximal anchor 14 and distal anchor 12 to pinch a region of the tubular organ located between them. This in turn creates a recess or fold in the wall of the tubular organ as shown in FIG. 7Y. Proximal anchor 14 is attached to connector 16 in the lumen of the tubular organ. The excess length of connector 16 may be cut or trimmed. The recess or fold in the wall of the tubular organ reduces the cross sectional area of the lumen of the tubular organ. The steps shown in FIGS. 7W-7Y may be repeated to create multiple recesses or folds in the walls of the tubular organ. Such a method may be used to treat a variety of diseases including, but not limited to incontinence, emphysema, obesity, vaginal prolapse, aneurysms, diverticuli, etc.

FIGS. 7Z through 7AD show cross sections of a tubular organ showing the steps of a second embodiment of a method of reducing the cross sectional area of the lumen of the tubular organ by implanting a device that pinches the walls of the tubular organ to create a recess. In FIGS. 7Z-7AD, the urethra is used as an example of a tubular organ that may be treated using this method. Other examples of organs that may be treated by the method shown in FIGS. 7Z-7AD include, but are not limited to bowel, stomach, esophagus, trachea, bronchii, bronchial passageways, veins, arteries, lymphatic vessels, ureters, bladder, cardiac atria or ventricles, uterus, fallopian tubes, etc. A distal anchor delivery device is introduced in the anatomy. The distal anchor delivery device may be introduced, for example, transluminally through the lumen of the tubular organ. The distal anchor delivery device is used to penetrate through a wall of the tubular organ. The distal anchor delivery device is used to deploy a distal anchor 12 in the wall of the tubular organ or in the surrounding anatomy as shown in FIG. 7Z. Distal anchor 12 is connected to a connector 16 that passes through the lumen of the tubular organ. Similarly, in the step shown in FIG. 7AA, a second distal anchor 12 is deployed in the wall of the tubular organ or in the surrounding anatomy. The second distal anchor 12 is also connected to a second connector 16 that passes through the lumen of the tubular organ. In the step shown in FIG. 7AB, a connecting device 214 is introduced in the lumen of the tubular organ over the two connectors 106. Connecting device 214 may be introduced, for example, transluminally through the lumen of the tubular organ. The two connectors 106 are pulled to create a desired tension in the two connectors 106. The tensions in the two connectors 106 cause the two distal anchors 102 to pinch a region of the tubular organ located between them. This in turn creates a recess or fold in the wall of the tubular organ as shown in FIG. 7AC. A desired region of the first connector is connected to a desired region of the second connector 16 by connecting device 214. This connection is created in the lumen of the tubular organ as shown in FIG. 7AD. The excess length of connectors 106 may be cut or trimmed. The recess or fold in the wall of the tubular organ reduces the cross sectional area of the lumen of the tubular organ. The steps shown in FIGS. 7Z-7AD may be repeated to create multiple recesses or folds in the walls of the tubular organ. Such a method may be used to treat a variety of diseases including, but not limited to incontinence, emphysema, obesity, vaginal prolapse, aneurysms, diverticuli, etc.

The methods and devices disclosed herein may be used to create multiple folds, bulges or recesses in the walls of a tubular organ to reduce the cross sectional area of the lumen of the tubular organ. For example, FIG. 7AE shows a cross section of a tubular organ showing a first embodiment of a method of reducing the cross sectional area of the lumen of the tubular organ by implanting devices that pinch the walls of the tubular organ to create two recesses. In FIG. 7AE, a first anchoring system comprising a proximal anchor 14 and a distal anchor 12 connected by a connector 16 is deployed as shown. The tension in connector 16 causes distal anchor 12 and proximal anchor 14 to pinch a region of the tubular organ located between them. This in turn creates a first recess or fold in the wall of the tubular organ as shown. Proximal anchor 14, distal anchor 12 and connector 16 may be deployed in the anatomy, for example, by the method shown in FIGS. 7W-7Y. Alternatively, proximal anchor 14, distal anchor 12 and connector 16 may be deployed in the anatomy by the method shown in FIGS. 7Z-7AD. A second anchoring system comprising a proximal anchor 14 and a distal anchor 12 connected by a connector 16 is also deployed as shown. The second anchoring system creates a second recess or fold in the wall of the tubular organ as shown. In the embodiment shown in FIG. 7AE, the second recess or fold is created at a location that is roughly diametrically opposite to the first recess or fold.

FIG. 7AF shows a cross section of a tubular organ showing a second embodiment of a method of reducing the cross sectional area of the lumen of the tubular organ by implanting devices that pinch the walls of the tubular organ to create two recesses. In FIG. 7AF, a first anchoring system comprising a proximal anchor 14 and a distal anchor 12 connected by a connector 16 is deployed as shown. The tension in connector 16 causes distal anchor 12 and proximal anchor 14 to pinch a region of the tubular organ located between them. This in turn creates a first recess or fold in the wall of the tubular organ as shown. Proximal anchor 14, distal anchor 12 and connector 16 may be deployed in the anatomy, for example, by the method shown in FIGS. 7W-7Y. Alternatively, proximal anchor 14, distal anchor 12 and connector 16 may be deployed in the anatomy by the method shown in FIGS. 7Z-7AD. A second anchoring system comprising a proximal anchor 14 and a distal anchor 12 connected by a connector 16 is also deployed as shown. The second anchoring system creates a second recess or fold in the wall of the tubular organ as shown. In the embodiment shown in FIG. 7AF, the second recess or fold is created at a location that is not diametrically opposite to the first recess or fold.

The methods and devices disclosed herein may be used to reinforce a fold, bulge or recess in the walls of a tubular organ to further reduce the cross sectional area of the lumen of the tubular organ. For example, FIG. 7AG shows a cross section of a tubular organ showing a method of reducing the cross sectional area of the lumen of the tubular organ by creating a recess in the walls of the tubular organ and reinforcing the recessed region. In FIG. 7AG, a first anchoring system comprising a proximal anchor 14 and a distal anchor 12 connected by a connector 16 is deployed in a tubular organ. The tension in connector 16 causes distal anchor 12 and proximal anchor 14 to pinch a region of the tubular organ located between them. This in turn creates a recess or fold in the wall of the tubular organ as shown. Proximal anchor 14, distal anchor 12 and connector 16 may be deployed in the anatomy, for example, by the method shown in FIGS. 7W-7Y. Alternatively, proximal anchor 14, distal anchor 12 and connector 16 may be deployed in the anatomy by the method shown in FIGS. 7Z-7AD. A second anchoring system comprising a proximal anchor 14 and a distal anchor 12 connected by a connector 16 is also deployed as shown. The second anchoring system is deployed in the recess or fold created by the first anchoring system in the wall of the tubular organ. The second anchoring system reinforces the recess or fold created by the first anchoring system. The second anchoring system may also increase the size of the recess or fold created by the first anchoring system. This in turn may further reduce the cross sectional area of the lumen of the tubular organ. It should also be understood that variations in the procedure may be usable to subtly alter the shape of the lumen of the tubular organ or may be usable to remove deformities or pockets in the lumen, for example, closing or compressing diverticuli or aneurysmic morphologies.

Figure 8:
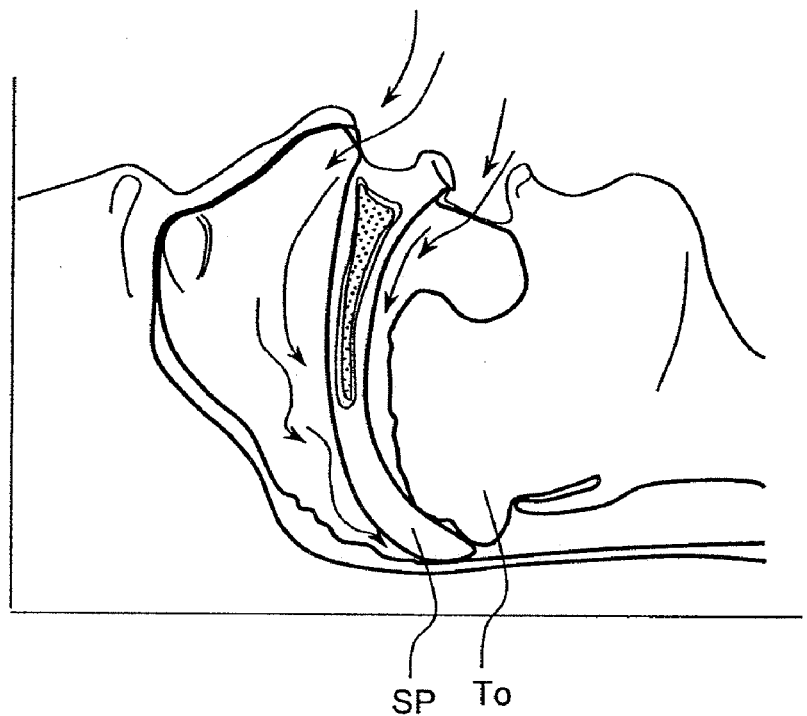
Figure 8:
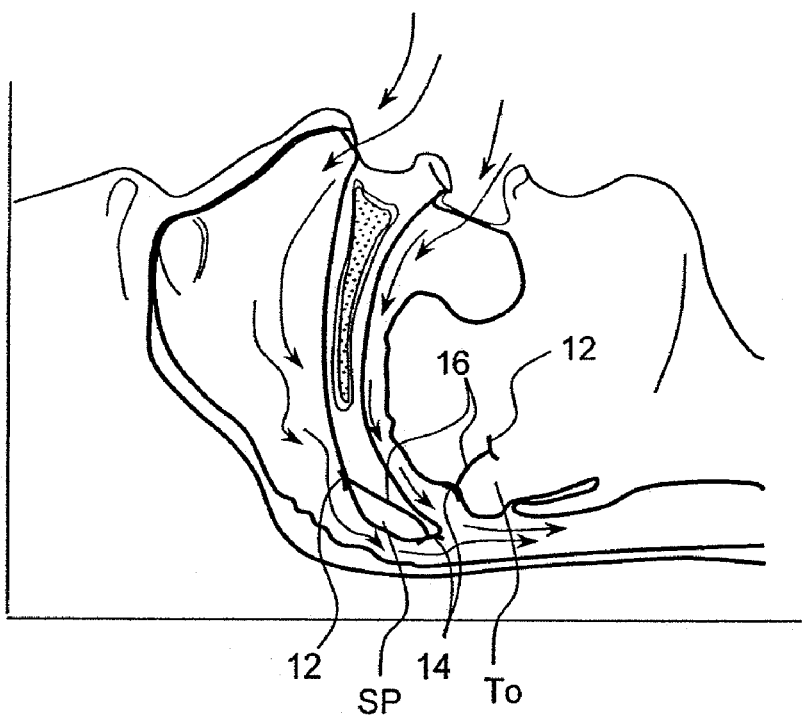
Figure 8:
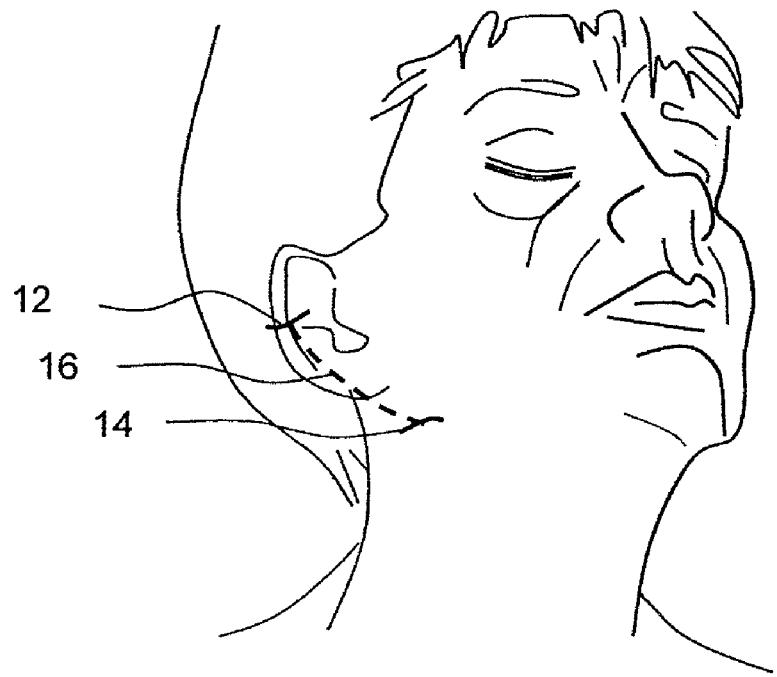
Figure 8:
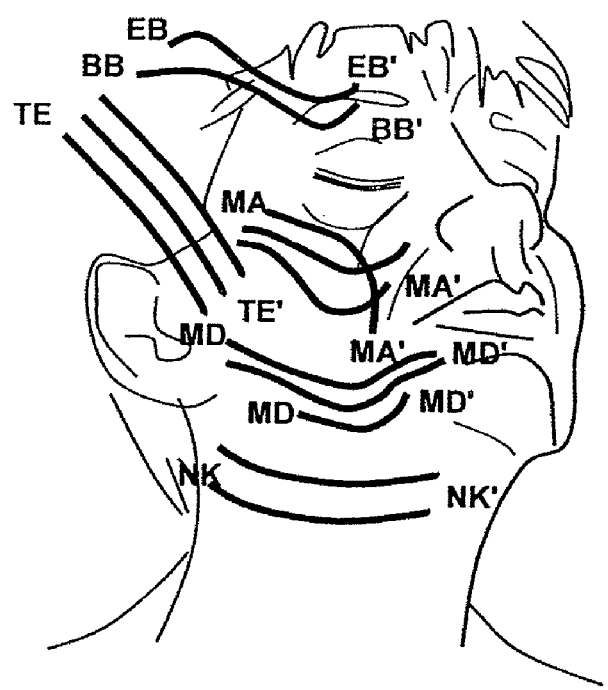

The various devices and methods disclosed herein may be used to prevent or treat a variety of diseases or disorders of a variety of anatomical systems. Examples of such anatomical systems include, but are not limited to the musculoskeletal system, the gastrointestinal system, the urinary system, etc. For example, FIG. 8A shows an anchoring system implanted in a stomach to reduce the volume of the stomach to treat obesity. The anchoring system comprises a proximal anchor 14 connected to a distal anchor 12 by a connector 16. Proximal anchor 14 is located on the outer surface or within the wall of the stomach of an obese patient. Similarly, distal anchor 12 is located on the outer surface or within the wall of the stomach of the obese patient. Connector 16 passes through the lumen of the stomach. The tension in connector 16 causes proximal anchor 14 and distal anchor 12 to compress a region of stomach located between them. This in turn reduces the volume of the stomach. This in turn restricts the volume of intake of food by the patient, thereby causing weight loss.

FIG. 8B shows a cross sectional view of a stomach before implanting an anchoring system to reduce the volume of the stomach. FIG. 8C shows a cross sectional view of the stomach of FIG. 8B after implanting an anchoring system to reduce the volume of the stomach. In FIG. 8C, the volume of the stomach is reduced by implanting an anchoring system. The anchoring system comprises a proximal anchor 14 connected to a distal anchor 12 by a connector 16.

The various devices and methods disclosed herein may be used to close or repair wounds. For example, FIG. 8D shows a section through wound edges closed by an anchoring system in a first configuration. In FIG. 8D, a wound comprising two wound edges is closed by an anchoring system comprising a proximal anchor 14 connected to a distal anchor 12 by a connector 16. The tension in connector 16 causes proximal anchor 14 and distal anchor 12 to compress the wound edges. This in turn brings the wound edges close to each other, thereby closing the wound. In the embodiment shown in FIG. 8D, the wound edges are closed in a side-to-side configuration. The anchoring system shown in FIG. 8D may be deployed, for example, by distal anchor delivery device 30 and proximal anchor delivery device 34 of FIGS. 6A and 6C respectively. Connector 16 may be fully or partially biodegradable or bioabsorbable.

FIG. 8E shows a section through wound edges closed by an anchoring system in a second configuration. In FIG. 8E, a wound comprising two wound edges is closed by an anchoring system comprising a proximal anchor 14 connected to a distal anchor 12 by a connector 16. The tension in connector 16 causes proximal anchor 14 and distal anchor 12 to compress the wound edges. This in turn brings the wound edges close to each other, thereby closing the wound. In the embodiment shown in FIG. 8D, the wound edges are closed in an end-to-end configuration. The anchoring system shown in FIG. 8D may be deployed, for example, by distal anchor delivery device 30 and proximal anchor delivery device 34 of FIGS. 6A and 6C respectively. Distal anchor delivery device 30 may comprise a curved distal tip. Connector 16 may be fully or partially biodegradable or bioabsorbable.

FIG. 8F shows an anchoring device used to reconnect torn tissues of the musculoskeletal system. In FIG. 8F, an anchoring system is used to reconnect a torn ligament Li. In the normal anatomy, one piece of the ligament Li is connected to bone Bo, and the other piece of ligament Li is connected to a muscle. The anchoring system comprises a proximal anchor 14 connected to a distal anchor 12 by a connector 16. The tension in connector 16 causes proximal anchor 14 and distal anchor 12 to compress the ends of the two pieces of ligament Li. This in turn brings the two pieces of ligament Li close to each other, thereby joining the torn ligament Li as shown in FIG. 8F. Similarly, other torn tissues of the musculoskeletal system such as torn muscles may be reconnected by an anchoring system.

FIG. 8G shows a sagittal section through the head of a patient suffering from sleep apnea. In FIG. 8G, the soft palate SP of the patient is blocking the flow of air from the nostrils to the lungs. Also, in FIG. 8G, the tongue TO of the patient is obstructing the fluid path from the mouth to the pharynx. Thus, the patient is unable to breathe normally.

FIG. 8H shows a sagittal section through the head of a patient suffering from sleep apnea who has been treated with two anchoring devices that displace the obstructing portions of the soft palate SP and the tongue To. In FIG. 8H, an anchoring system comprising a proximal anchor 14 connected to a distal anchor 12 by a connector 16 is implanted in the posterior region of the soft palate SP. The tension in connector 16 causes proximal anchor 14 and distal anchor 12 to compress a region of the soft palate SP. This in turn displaces the obstructing region of the soft palate SP as shown. Thus, the flow of air from the nostrils to the lungs is not blocked by the soft palate SP. In addition, or alternatively, a region of the tongue TO may also be displaced by an anchoring system. In FIG. 8F, the anchoring system comprises a proximal anchor 14 connected to a distal anchor 12 by a connector 16. The tension in connector 16 causes proximal anchor 14 and distal anchor 12 to compress a posterior region of the tongue TO. This in turn displaces the obstructing region of the tongue TO as shown. Thus, the fluid path from the mouth to the lungs is not blocked by the tongue TO. Multiple anchoring systems may be used to displace obstructing regions of the soft palate SP and/or obstructing regions of the tongue TO.

The devices and systems disclosed herein may be used for a variety of cosmetic procedures. For example, FIG. 8I shows an anchoring system that is implanted to lift loose skin in the face of a human. Such an anchoring system may be used, for example, to lift wrinkled skin to smoothen wrinkles. In FIG. 8I, an anchoring system comprising a proximal anchor 14 connected to a distal anchor 12 by a connector 16 is implanted in the tissues of the face as shown. In the embodiment shown in FIG. 8I, distal anchor is implanted behind an ear of the patient. Proximal anchor 14 is implanted in a region of the cheek of the patient having wrinkled facial skin. The tension in connector 16 causes proximal anchor 14 and distal anchor 12 to displace the region of the cheek having wrinkled facial skin. This in turn stretches the wrinkled facial skin to improve the cosmetic appearance of the human. Similar methods may be used to lift sagging facial skin to improve the cosmetic appearance of a human.

Various regions of the face may be treated by methods similar to the method shown in FIG. 8J. For example, FIG. 8J shows a view of a human face showing facial regions that may be treated by a method similar to the method shown in FIG. 8I to improve the cosmetic appearance of the human. One example of a facial region that can be treated by a method similar to the method shown in FIG. 8I is the eyebrow zone. A proximal anchor 14 may be implanted in the region EB and a distal anchor 12 may be implanted in a region EB'. Proximal anchor 14 is connected to distal anchor 12 by a connector 16 that passes through the line joining region EB to region EB'. In an alternate embodiment, proximal anchor 14 may be implanted in the region EB' and a distal anchor 12 may be implanted in a region EB. Another example of a facial region that can be treated by a method similar to the method shown in FIG. 8I is the temporal zone. A proximal anchor 14 may be implanted in the region TE and a distal anchor 12 may be implanted in a region TE'. Proximal anchor 14 is connected to distal anchor 12 by a connector 16 that passes through the line joining region TE to region TE'. In an alternate embodiment, proximal anchor 14 may be implanted in the region TE' and a distal anchor 12 may be implanted in a region TE. Another example of a facial region that can be treated by a method similar to the method shown in FIG. 8I is the malar zone. A proximal anchor 14 may be implanted in the region MA and a distal anchor 12 may be implanted in a region MA'. Proximal anchor 14 is connected to distal anchor 12 by a connector 16 that passes through the line joining region MA to region MA'. In an alternate embodiment, proximal anchor 14 may be implanted in the region MA' and a distal anchor 12 may be implanted in a region MA. Another example of a facial region that can be treated by a method similar to the method shown in FIG. 8I is the mandibular zone. A proximal anchor 14 may be implanted in the region MD and a distal anchor 12 may be implanted in a region MD'. Proximal anchor 14 is connected to distal anchor 12 by a connector 16 that passes through the line joining region MD to region MD'. In an alternate embodiment, proximal anchor 14 may be implanted in the region MD' and a distal anchor 12 may be implanted in a region MD. Another example of a facial region that can be treated by a method similar to the method shown in FIG. 8I is the neckerchief zone. A proximal anchor 14 may be implanted in the region NK and a distal anchor 12 may be implanted in a region NK'. Proximal anchor 14 is connected to distal anchor 12 by a connector 16 that passes through the line joining region NK to region NK'. In an alternate embodiment, proximal anchor 14 may be implanted in the region NK' and a distal anchor 12 may be implanted in a region NK. The facial regions shown in FIG. 8J may be treated, for example, to improve the cosmetic appearance of a human with wrinkled or sagging facial skin.

FIG. 8K shows a sagittal section through the lower abdomen of a human female showing an embodiment of a method of treating female urinary incontinence by a sling attached to the anatomy by anchoring devices. FIG. 8K shows the lower abdomen of a human female showing the urinary bladder UB, uterus U and rectum R. The method shown in FIG. 8K is especially suited to treat stress incontinence caused due to physical changes because of pregnancy, childbirth, menopause, etc. The physical changes prevent the urethral sphincter from closing tightly. This in turn causes urine to leak during moments of physical stress. The method shown in FIG. 8K is similar to the Tension-Free Vaginal Tape (TVT) Procedure. In the method shown in FIG. 8K, a sling 220 is inserted around the urethra UT. Sling 220 may be inserted around the urethra UT by a retropubic or transvaginal approach. Sling 220 is made of suitable biocompatible materials. Examples of such materials include, autologous graft tissue such as muscles, ligaments, tendons, etc.; animal graft tissue from animals such as pigs, etc.; synthetic biodegradable or non-biodegradable polymers, etc. The two ends of sling 220 are anchored to surrounding anatomical regions such as the pubic bone, periostial membrane of the pubic bone, Cooper's ligament, abdominal wall, lateral pelvic wall, outer bladder wall, pelvic fascia by anchoring devices. In the embodiment shown in FIG. 8K, the two ends of sling 220 are attached to the surrounding anatomical structures by two anchoring devices. Each anchoring device comprises a proximal anchor 14 and a distal anchor 12 connected to proximal anchor 14 by a connector. Connector 16 passes through an end of sling 220 such that proximal anchor 14 is anchored in the material of sling 220. Distal anchor 12 anchors into the surrounding anatomical structures, thereby attaching the end of sling 220 to the surrounding anatomical structures. Sling 220 supports the urethra UT and partially compresses the urethra UT. Sling 220 cause a sufficient compression of the urethra UT to enable urethral sphincter to close tightly. It should be noted that the intent of these procedures is not in all cases to create compression on the urethra but in other situations is used to support surrounding structures or prevent the movement of certain structures under certain conditions, such as in the case of hypermobility. In this circumstance, the devices would normally be "tension-free" and would only be brought into tension when there is movement of the tissue with respect to the anchor/tensioning-member assembly.

FIG. 8L shows a cross section of a normal urethra UT. FIG. 8M shows a cross section of the urethra UT in a human female suffering from stress urinary incontinence. In FIG. 8M, the urethra UT has reduced support from surrounding anatomical structures. This prevents the urethral sphincter from closing tightly causing incontinence. FIG. 8N shows a cross section of the urethra UT in a human female suffering from stress urinary incontinence where the urethra UT has been supported with a sling. In FIG. 8N, sling 220 supports the urethra UT and partially compresses the urethra UT. Sling 220 causes a sufficient compression of the urethra UT to enable urethral sphincter to close tightly. This in turn reduces the severity of the incontinence.

FIG. 8O shows a coronal section through the lower abdomen of a human female suffering from stress urinary incontinence. Two anchoring devices have been implanted in order to tether together separate tissue planes. The tethering of these planes reduces their relative movement; thus reducing hypermobility. Each anchoring device comprises a proximal anchor 14 and a distal anchor 12 connected to proximal anchor 14 by a connector that passes through separate tissue planes. Tissue planes supports the urethra UT and may partially compresses the urethra UT. With this supportive tissue plane now fixed in place, forces which would otherwise have caused the involuntary descent of the bladder resulting in incontinence are now apposed.

One or more anchoring or tensioning devices disclosed herein may be used to anchor a first anatomical region to a second anatomical region. For example, one or more anchoring or tensioning devices disclosed herein may be used to perform various embodiments or modifications of colposuspension procedures. In the standard colposuspension procedure (Burch colposuspension) a surgeon sutures a region of the vaginal wall to the Cooper's ligament. This is performed by placing two non-absorbable sutures on each side of the urethra, partially through the segment of the vaginal wall located under the junction where the bladder joins the urethra. The two sutures on each side (four total) are then attached to the Cooper's ligament. A key difficulty in performing this procedure is the step of tying a knot, especially when the procedure is performed laparoscopically. The need to synch and tie sutures sequentially through a laparoscope is very time consuming using standard techniques and it is often difficult to achieve the desired suture tension. For example, FIG. 8P shows a section through the lower abdomen showing an embodiment of a colposuspension procedure wherein one or more regions of the vaginal wall of a patient suffering from incontinence are suspended to the Cooper's ligament by one or more anchoring devices. In the embodiment shown in FIG. 8P, one or more distal anchors 102 are deployed in a desired region of the Cooper's ligament by a device introduced through the vagina V. The one or more distal anchors 102 may be deployed through a needle that emerges through the device introduced through the vagina and penetrate through the vaginal wall to reach the desired location. The one or more distal anchors 102 are deployed on each side of the urethra as shown in FIG. 8P. Each distal anchor 12 is connected to a connector 16. A proximal anchor 106 is attached to a desired region of each connector 16 located in the vagina. Each proximal anchor 14 anchors one end of each connector 16 to the vaginal wall. The tension in connector 16 causes the vaginal wall to be suspended by Cooper's ligament. The suspension of the vaginal wall to the Cooper's ligament reduces the severity of the incontinence. The abovementioned method may be visualized by a laparoscope inserted in the pelvic area.

In an alternate embodiment, the devices for deploying proximal anchor 14 and/or distal anchor 12 are inserted laparoscopically into the pelvic area. A laparoscope may be used to visualize the instruments. In one embodiment, the laparoscope is introduced through the navel. The devices for deploying proximal anchor 14 and/or distal anchor 12 are introduced through two other incisions in the lower abdomen.

One or more devices or methods disclosed herein may be used to attach a plugging element to a tubular organ to seal an opening or a puncture site of the tubular organ. For example, FIG. 8Q shows an anchoring device used to attach a seal to a puncture site on a blood vessel BV to seal the puncture site. In FIG. 8Q, the puncture site on the blood vessel is plugged by a seal 222. Seal 222 is made of suitable biocompatible materials. Examples of such materials include, but are not limited to collagen, gelfoam, other bioabsorbable polymer matrices, etc. Seal 222 is attached to the puncture site by an anchoring device that passes through seal 222. The anchoring device comprises a distal anchor 12, a proximal anchor 14 and a connector 16 that connects distal anchor 12 to proximal anchor 14. Distal anchor 12 is located in the lumen of the blood vessel. Proximal anchor 14 is located outside the blood vessel, such that connector 16 passes through the puncture site. A sufficient tension is created in connector 16 such that distal anchor 12 and proximal anchor 14 compress the edges of the puncture site to seal 222. This in turn securely attaches seal 222 to the edges of the puncture site, thereby sealing the puncture site.

One or more anchoring or tensioning devices disclosed herein may be used to suspend a first anatomical region to a second anatomical region. For example, one or more anchoring or tensioning devices disclosed herein may be used to suspend a breast region to an anatomical region superior anatomical region such as a muscle, subcutaneous fatty tissue, a ligament, etc. This may be used to achieve cosmetic modification of the breasts. In a particular embodiment, a subcutaneous fatty tissue of a breast is suspended to an anatomical region superior to the fatty tissue such as a muscle, a subcutaneous fatty tissue, a ligament, etc. In another particular embodiment, a breast tissue is suspended to an anatomical region superior to the breast tissue such as a muscle, a subcutaneous fatty tissue, a ligament, etc. The anchor delivery devices may be introduced in the anatomy through a cannula. Alternatively the anchor delivery device may comprise a sharp distal tip to penetrate through tissue. For example, FIG. 8R shows a view of the pectoral region of a human female. A region of a breast may be suspended to an anatomical region superior to the region of the breast using the anchoring devices disclosed herein. This may be used, for example, for cosmetic mastopexy. The anchoring devices may be deployed such that the connectors of the anchoring devices pass through the dashed lines shown in FIG. 8R. FIG. 8S shows the pectoral region of a human female wherein mastopexy has been performed on one or more regions of the breasts using the anchoring devices disclosed herein.

Any of the anchors disclosed herein may be made of suitable elastic or non-elastic biocompatible materials. Examples of such materials include, but are not limited to metals such as stainless steel 304, stainless steel 316, nickel-Titanium alloys, titanium, etc. and polymers such as Pebax, Polyimide, braided Polyimide, Polyurethane, Nylon, PVC, Hytrel, HDPE, PEEK, PTFE, PFA, FEP, EPTFE, shape memory polymers, etc.

Connector 16 described herein may be made from several biocompatible materials. For example, connector 16 may be made from synthetic fibers e.g. various grades of Nylon, polyethylene, polypropylene, polyester, Aramid, shape memory polymers, etc.; metals e.g. various grades of stainless steel, titanium, nickel-titanium alloys, cobalt-chromium alloys, tantalum etc.; natural fibers e.g. cotton, silk etc.; rubber materials e.g. various grades of silicone rubber, etc. In a particular embodiment, connector is made of elastic suture materials. Connector 16 may comprise one or more serrations or notches. The serrations or notches may be aligned in a particular direction to allow relatively easy movement of an outer body along connector 16 in one direction and offer significant resistance to movement of the outer body along the connector 16 in the opposite direction. Connector 16 may comprise a single filament or multiple filaments of one or more materials. For example, connector 16 may comprise a composite braided structure in a plastic/metal or plastic/plastic configuration to reduce profile and increase strength. Such composite materials could have preset levels of elasticity. Connector 16 may be coated with a coating. Examples of such coatings include, but are not limited to lubricious coatings, antibiotic coatings, etc.

One or more of the devices disclosed herein may comprise a variety of markers. In one embodiment, the markers are visual markers located on the surface of the one or more devices. Such markers may enable a user to determine the absolute of relative location of the one or more devices visually or by an instrument such as a cystoscope. In another embodiment the markers may be radiographic markers. Similarly, one or more of the devices disclosed herein may comprise a variety of electromagnetic or ultrasonic or MRI or multimodality markers.

A suitable urinary catheter may be inserted into the urethra for a desired period of time after completion of one or more of the procedures described herein. The urinary catheter may be used, for example, if the patient is at risk of bleeding or acute urethral obstruction.

The one or more anchoring devices disclosed herein may be designed to allow a user to reverse the anatomical changes caused by the anchoring devices if needed. In one method embodiment the anatomical changes may be reversed by cutting connector 16 near proximal anchor 14. In another method embodiment the anatomical changes may be reversed by cutting connector 16 near distal anchor 12.

One or more components such as distal anchor 12, proximal anchor 14, connector 16, etc. of the one or more anchoring devices disclosed herein may be designed to be completely or partially biodegradable or biofragmentable.

The devices and methods disclosed herein may be used to treat a variety of pathologies in a variety of tubular organs or organs comprising a cavity or a wall. Examples of such organs include, but are not limited to urethra, bowel, stomach, esophagus, trachea, bronchii, bronchial passageways, veins (e.g. for treating varicose veins or valvular insufficiency), arteries, lymphatic vessels, ureters, bladder, cardiac atria or ventricles, uterus, fallopian tubes, etc.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unpatentable or unsuitable for its intended use. Also, for example, where the steps of a method are described or listed in a particular order, the order of such steps may be changed unless to do so would render the method unpatentable or unsuitable for its intended use. All reasonable additions, deletions, modifications and alterations are to be considered equivalents of the described examples and embodiments and are to be included within the scope of the following claims.

What is claimed is:

1. A device for stenting a lumen or cavity in the body of a human or animal subject, said device comprising:
    an endoscope having a distal end and defining an endoscope longitudinal axis;
    an elongate endoscope channel for receiving the endoscope therein;
    an elongate channel substantially parallel to the endoscope channel, the elongate channel houses at least one support member prior to deployment;
    an elongate structure configured to project laterally from the elongate channel, the elongate structure retaining a counteractive element;
    wherein the at least one support member is positioned within the lumen or cavity or in tissue adjacent to the lumen or cavity and generally parallel to the endoscope longitudinal axis after deployment from the elongate channel, the at least one support member having a length greater than a width and including a plurality of spaced arms extending along the length; and
    at least one tensioning member attached to the at least one support member at a first end and the counteractive elements at a second end, said at least one tensioning member being under sufficient tension to cause the at least one support member to stent the lumen and being generally perpendicular to the endoscope longitudinal axis after deployment;
    wherein the at least one tensioning member is defined by inelastic material and the plurality of spaced arms compress the at least one tensioning member;
    wherein the distal end of the endoscope is positioned to view deployment of the at least one support member.

2. A device according claim 1, wherein the at least one support member comprises an anchor that becomes anchored in or against tissue.

3. A system for altering the shape of a lumen in the body of a human comprising:
    an endoscope having a distal end and defining an endoscope longitudinal axis;
    an elongate endoscope channel for receiving the endoscope therein;
    an elongate channel substantially parallel to the elongate endoscope channel, the elongate channel houses at least one luminal communicating element prior to deployment;
    an elongate structure configured to project laterally from the elongate channel, the elongate structure retaining at least one counteractive element;
    wherein the at least one luminal communicating element directly or indirectly communicates force to at least one region of the lumen and is generally parallel to the endoscope longitudinal axis after deployment from the elongate channel, the luminal communicating element having a length greater than its width and including a plurality of spaced arms extending along the length;
    the at least one counteractive element placed outside the lumen which is retained at one or more pre-determined locations outside the lumen; and
    at least one force communicating element transmitting force between the luminal communicating element and the at least one counteractive element and being generally perpendicular to the endoscope longitudinal axis after deployment, whereby the presence of at least one of each luminal communicating element, counteractive element, and force communicating element together results in a change in the shape of the lumen;
    wherein the at least one force communicating element is defined by inelastic material, the plurality of spaced arms compress the at least one force communicating element and the luminal communicating element is attached to the at least one force communicating element at or near the lumen;
    wherein the distal end of the endoscope is positioned to view deployment of the luminal communicating element.

4. The device of claim 1, wherein the at least one support member is sized and shaped to be received within an urethra.

5. The device of claim 1, wherein the at least one support member is sized and shaped to be received within a prostate.

6. The device of claim 1, wherein the at least one support member is sized and shaped to pass through a prostate and to be placed in apposition with a prostate capsule.

7. The system of claim 3, wherein the at least one luminal communicating element is sized and shaped to be received within an urethra.

8. The system of claim 3, wherein the at least one counteractive element is sized and shaped to be retained within a prostate.

9. The system of claim 3, wherein the at least one counteractive element is sized and shaped to pass through a prostate and be placed in apposition with a prostate capsule.

10. The device of claim 1, further comprising:
a tensioning member elongate channel substantially parallel to the elongate endoscope channel, wherein the at least one tensioning member passes through the tensioning member elongate channel.

11. The device of claim 1, wherein the elongate channel has a support member opening in its side wall in a distal portion.

12. The device of claim 10, further comprising:
an actuator, wherein movement of the actuator in a proximal direction substantially parallel to the elongate channel shears the at least one tensioning member below a bottom surface of the at least one support member.

13. The device of claim 10, wherein, prior to deployment of the at least one support member and the at least one tensioning member from the device, the length of the at least one support member is substantially parallel to the elongate channel in which it is housed and the length of the at least one support member is transverse to the tensioning member.

14. The system of claim 3, further comprising:
a force communicating element elongate channel substantially parallel to the endoscope channel, wherein the at least one force communicating element passes through the force communicating element elongate channel.

15. The system of claim 3, wherein the elongate channel has a luminal communicating element opening in its side wall in a distal portion.

16. The system of claim 14, further comprising:
an actuator, wherein movement of the actuator in a proximal direction substantially parallel to the elongate channel shears the at least one force communicating element below a bottom surface of the at least one luminal communicating element.

17. The system of claim 14, wherein, prior to deployment of the at least one luminal communicating element and at least one force communicating element from the device, the length of the at least one luminal communicating element is substantially parallel to the elongate channel in which it is housed and the length of the at least one luminal communicating element is transverse to the force communicating element.

* * * * *

UNITED STATES PATENT AND TRADEMARK OFFICE
CERTIFICATE OF CORRECTION

| | | |
|---|---|---|
| PATENT NO. | : 7,951,158 B2 | Page 1 of 1 |
| APPLICATION NO. | : 11/833710 | |
| DATED | : May 31, 2011 | |
| INVENTOR(S) | : Joseph Cantanese, III et al. | |

It is certified that error appears in the above-identified patent and that said Letters Patent is hereby corrected as shown below:

Title page - Item 57, Abstract, after "treating" remove "a"

Column 1 - In line 22, after "treating" remove "a"

Column 3 - In line 36, after "incisions" remove "are"

Column 5 - In line 27, after "(3%)" insert --.--

Column 11 - In line 4, change "4M" to --4AA--

Column 21 - In line 53, change "allow" to --alloy--

Column 23 - In line 12, after "may" insert --be--

Column 23 - In line 63 change "as" to --a--

Column 40 - In line 41, remove "EXAMPLES"

Column 51 - In line 7, change "shows" to --show--

Column 57 - In line 2, change "supports" to --support--

Column 57 - In line 3, change "compresses" to --compress--

Signed and Sealed this

Thirteenth Day of March, 2012

David J. Kappos
*Director of the United States Patent and Trademark Office*